US008691539B2

(12) United States Patent
Jantama et al.

(10) Patent No.: US 8,691,539 B2
(45) Date of Patent: Apr. 8, 2014

(54) MATERIALS AND METHODS FOR EFFICIENT SUCCINATE AND MALATE PRODUCTION

(75) Inventors: Kaemwich Jantama, Gainesville, FL (US); Mark John Haupt, Pace, FL (US); Xueli Zhang, Gainesville, FL (US); Jonathan C. Moore, Gainesville, FL (US); Keelnatham T. Shanmugam, Gainesville, FL (US); Lonnie O'Neal Ingram, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 408 days.

(21) Appl. No.: 12/529,826

(22) PCT Filed: Mar. 19, 2008

(86) PCT No.: PCT/US2008/057439
§ 371 (c)(1),
(2), (4) Date: Mar. 24, 2010

(87) PCT Pub. No.: WO2008/115958
PCT Pub. Date: Sep. 25, 2008

(65) Prior Publication Data
US 2010/0184171 A1 Jul. 22, 2010

Related U.S. Application Data

(60) Provisional application No. 60/895,806, filed on Mar. 20, 2007.

(51) Int. Cl.
*C12P 7/46* (2006.01)
*C12N 9/00* (2006.01)
*C12N 1/22* (2006.01)
*C12N 15/00* (2006.01)
*C07H 21/04* (2006.01)

(52) U.S. Cl.
USPC ..... 435/145; 435/183; 435/252.3; 435/320.1; 536/23.2

(58) Field of Classification Search
None
See application file for complete search history.

(56) References Cited

U.S. PATENT DOCUMENTS

| | | | |
|---|---|---|---|
| 5,583,278 A | 12/1996 | Alt et al. | |
| 5,723,322 A | 3/1998 | Guettler et al. | |
| 5,869,301 A | 2/1999 | Nghiem et al. | |
| 6,159,738 A | 12/2000 | Donnelly et al. | |
| 6,607,885 B1 | 8/2003 | Larossa et al. | |
| 6,911,329 B2 | 6/2005 | Dusch et al. | |
| 7,098,009 B2 | 8/2006 | Shanmugam et al. | |
| 7,145,058 B2 | 12/2006 | Sandal et al. | |
| 7,223,567 B2 | 5/2007 | Ka-Yiu et al. | |
| 2004/0152159 A1 | 8/2004 | Causey et al. | |
| 2005/0170482 A1 | 8/2005 | San et al. | |
| 2007/0037265 A1 | 2/2007 | Zhou et al. | |
| 2007/0072279 A1 | 3/2007 | Meynial-Salles et al. | |
| 2007/0072280 A1 | 3/2007 | Cirino et al. | |
| 2009/0148914 A1 | 6/2009 | Ingram et al. | |
| 2010/0159544 A1 | 6/2010 | Lee et al. | |

FOREIGN PATENT DOCUMENTS

| | | |
|---|---|---|
| WO | WO 2004/043881 | 5/2004 |
| WO | WO 2005/073364 | 8/2005 |
| WO | WO 2008/119009 | 10/2008 |

OTHER PUBLICATIONS

Christian et al. Biotechnology Progress, vol. 23, No. 2, Jan. 25, 2007, pp. 381-388.*
Sanchez et al. Metab Eng. May 2005;7(3):229-39.*
Zhou et al. Appl Environ Microbiol. Apr. 2003;69(4):2237-44.*
Lee et al. Appl Environ Microbiol. Dec. 2005;71(12):7880-7.*
Lin et al. Metab Eng. Mar. 2005;7(2):116-27.*
Cox et al. Metab Eng. Jan. 2006;8(1):46-57. Epub Nov. 2, 2005.*
Meyer, M. et al. "In Vitro Binding of the Response Regulator CitB and of its Carboxy-terminal Domain to A + T-rich DNA Target Sequences in the Control Region of the Divergent *citC* and *citS* Operons of *Klebsiella pneumoniae*" *J. Mol. Biol.*, Jul. 27, 1997, pp. 719-731, vol. 269, No. 5 XP-004453842.
Kim, Y. et al. "Construction of an *Escherichia coli* K-12 Mutant for Homoethanologenic Fermentation of Glucose or Xylose without Foreign Genes" *Applied and Environmental Microbiology*, Mar. 1, 2007, pp. 1766-1771, vol. 73, No. 6, XP-008102027.
Jantama, K. et al. "Eliminating Side Products and Increasing Succinate Yields in Engineered Strains of *Escherichia coli* C" *Biotechnology and Bioengineering*, Jun. 4, 2008, pp. 881-892, vol. 101, No. 5, XP-002551943.
Iverson, T. M. et al. "Crystallographic Studies of the *Escherichia coli* Quinol-Fumarate Reductase with Inhibitors Bound to the Quinol-binding Site" *The Journal of Biological Chemistry*, May 3, 2002, pp. 16124-16130, vol. 277, No. 18.
Jantama, K. et al. "Combining Metabolic Engineering and Metabolic Evolution to Develop Nonrecombinant Strains of *Escherichia coli* C That Produce Succinate and Malate" *Biotechnology and Bioengineering*, Apr. 1, 2008, pp. 1140-1153, vol. 99, No. 5.
Jarboe, L. R. et al. "Determination of the *Escherichia coli* S-Nitrosoglutathione Response Network Using Integrated Biochemical and Systems Analysis" *The Journal of Biological Chemistry*, Feb. 22, 2008, pp. 5148-5157, vol. 283, No. 8.
Andersson, C. et al. "Effect of Different Carbon Sources on the Production of Succinic Acid Using Metabolically Engineered *Escherichia coli*" *Biotechnology and Bioengineering*, Jul. 20, 1997, pp. 328-338, vol. 55, No. 2.

(Continued)

*Primary Examiner* — Christian Fronda
(74) *Attorney, Agent, or Firm* — Saliwanchik, Lloyd & Eisenschenk

(57) ABSTRACT

Genetically engineered microorganisms have been constructed to produce succinate and malate in mineral salt media in pH-controlled batch fermentations without the addition of plasmids or foreign genes. The subject invention also provides methods of producing succinate and malate comprising the culture of genetically modified microorganisms.

54 Claims, 20 Drawing Sheets

(56) References Cited

OTHER PUBLICATIONS

Ajl, S. J. et al. "Enzymatic Fixation of Carbon Dioxide in α-KETO-Glutaric Acid" *Proceedings of the National Academy of Sciences*, Nov. 15, 1948, pp. 491-498, vol. 34, No. 11.

Asghari, A. et al. "Ethanol production from hemicellulose hydrolysates of agricultural residues using genetically engineered *Escherichia coli* strain KO11" *Journal of Industrial Microbiology*, 1996, pp. 42-47, vol. 16.

Kao, K. C. et al. "A Global Regulatory Role of Gluconeogenic Genes in *Escherichia coli* Revealed by Transcriptome Network Analysis" *The Journal of Biological Chemistry*, Oct. 28, 2005, pp. 36079-36087, vol. 280, No. 43.

Delbaere, L.T.J. et al. "Structure/function studies of phosphoryl transfer by phosphoenolpyruvate carboxykinase" *Biochimica et Biophysica ACTA 1697*, 2004, pp. 271-278.

De Graef, M. R. et al. "The Steady-State Internal Redox State (NADH/NAD) Reflects the External Redox State and Is Correlated with Catabolic Adapation in *Escherichia coli*" *Journal of Bacteriology*, Apr. 1999, pp. 2351-2357, vol. 181, No. 8.

Chao, Y. et al. "Alteration of Growth Yield by Overexpression of Phosphoenolpyruvate Carboxylase and Phosphoenolpyruvate Carboxykinase in *Escherichia coli*" *Applied and Environmental Microbiology*, Dec. 1993, pp. 4261-4265, vol. 59, No. 12.

Cox, S. J. et al. "Development of a metabolic network design and optimization framework incorporating implementation constraints: A succinate production case study" *Metabolic Engineering*, 2006, pp. 46-57, vol. 8.

Datsenko, K. A. et al. "One-step inactivation of chromosomal genes in *Escherichia coli* K-12 using PCR products" *PNAS*, Jun. 6, 2000, pp. 6640-6645, vol. 97, No. 12.

Chatterjee, R. et al. "Mutation of the *pts*G Gene Results in Increased Production of Succinate in Fermentation of Glucose by *Escherichia coli*" *Applied and Environmental Microbiology*, Jan. 2001, pp. 148-154, vol. 67, No. 1.

Canovas, J. L. et al. "Phosphoenolpyruvate Carboxylase from *Escherichia coli*" *Methods in Enzymology*, 1969, pp. 288-292, vol. 13.

Chang, Y. et al. "Conversion of *Escherichia coli* pyruvate oxidase to an 'α-ketobutyrate oxidase'" *Biochem. J.*, 2000, pp. 717-724, vol. 352.

Causey, T. B. et al. "Engineering *Escherichia coli* for efficient conversion of glucose to pyruvate" *PNAS*, Feb. 24, 2004, pp. 2235-2240, vol. 101, No. 8.

Hopper, D. J. et al. "The Regulation of *Escherichia coli* Methylglyoxal Synthase; A New Control Site in Glycolysis?" *FEBS Letters*, Mar. 1971, pp. 213-216, vol. 13, No. 4.

Goldie, A. H. et al. "Allosteric Control by Calcium and Mechanism of Desensitization of Phosphoenolpyruvate Carboxykinase of *Escherichia coli*" *The Journal of Biological Chemistry*, Feb. 25, 1980, pp. 1399-1405, vol. 255, No. 4.

Grabar, T. B. et al. "Methylglyoxal bypass identified as source of chiral contamination in L(+) and D(−)-lactate fermentations by recombinant *Escherichia coli*" *Biotechnol Lett*, 2006, pp. 1527-1535, vol. 28.

Gokarn, R. R. et al. "Metabolic Analysis of *Escherichia coli* in the Presence and Absence of the Carboxylating Enzymes Phosphoenolpyruvate Carboxylase and Pyruvate Carboxylase" *Applied and Environmental Microbiology*, May 2000, pp. 1844-1850, vol. 66, No. 5.

Farmer, W. R. et al. "Reduction of Aerobic Acetate Production by *Escherichia coli*" *Applied and Environmental Microbiology*, Aug. 1997, pp. 3205-3210, vol. 63, No. 8.

Goldie, A. H. et al. "Genetic and Physiological Characterization of *Escherichia coli* Mutants Deficient in Phosphoenolpyruvate Carboxykinase Activity" *Journal of Bacteriology*, Mar. 1980, pp. 1115-1121, vol. 141, No. 3.

Heßlinger, C. et al. "Novel keto acid formate-lyase and propionate kinase enzymes are components of an anaerobic pathway in *Escherichia coli* that degrades L-threonine to propionate" *Molecular Microbiology*, 1998, pp. 477-492, vol. 27, No. 2.

Fraenkel, D. G. (1996) Section A, Class I Reactions: Generation of Precursor Metabolites and Energy, Glycolysis, Chapter 14, Böck, R. Curtiss III, J. B. Kaper, F. C. Neidhardt, T. Nyström, K. E. Rudd, and C. L. Squires (ed.), EcoSal—*Escherichia coli* and *Salmonella*: Cellular and Molecular Biology. [Online.] http://www.ecosal.org. ASM Press, Washington, D.C.

Egyud, L. G. et al. "On the Regulation of Cell Division" *Biochemistry*, 1966, pp. 203-207, vol. 56.

Du, C. et al. "Succinic acid production from wheat using a biorefining strategy" *Appl Microbiol Biotechnol*, 2007, pp. 1263-1270, vol. 76.

Laivenieks, M. et al. "Cloning, Sequencing, and Overexpression of the *Anaerobiospirillum succiniciproducens* Phosphoenolpyruvate Carboxykinase (*pck*A) Gene" *Applied and Environmental Microbiology*, Jun. 1997, pp. 2273-2280, vol. 63, No. 6.

Kim, P. et al. "Effect of Overexpression of *Actinobacillus succinogenes* Phosphoenolpyruvate Carboxykinase on Succinate Production in *Escherichia coli*" *Applied and Environmental Microbiology*, Feb. 2004, pp. 1238-1241, vol. 70, No. 2.

Kulla, H. et al. "Energy-Dependent Inactiviation of Citrate Lyase in *Enterobacter aerogenes*" *Journal of Bacteriology*, Dec. 1977, pp. 764-770, vol. 132, No. 3.

Kessler, D. et al. "Anaerobic dissimilation of pyruvate" Neidhardt FC, Curtiss III R, Ingraham JL, Lin ECC, Low KB, Magasanik B, Reznikoff WS, Riley M, Schaechter M, Umbarger HE, editors. *Escherichia coli* and *Salmonella*: Cellular and Molecular Biology. ASM Press, Washington, D.C., 1996, pp. 199-205.

Lee, S. Y. et al. "Fermentative Production of Chemicals That Can Be Used for Polymer Synthesis" *Macromolecular Bioscience*, 2004, pp. 157-164, vol. 4.

Lee, S. J. et al. "Metabolic Engineering of *Escherichia coli* for Enhanced Production of Succinic Acid, Based on Genome Comparison and In Silico Gene Knockout Simulation" *Applied and Environmental Microbiology*, Dec. 2005, pp. 7880-7887, vol. 71, No. 12.

Lee, S. J. et al. "Genome-Based Metabolic Engineering of *Mannheimia succiniciproducens* for Succinic Acid Production" *Applied and Environmental Microbiology*, Mar. 2006, pp. 1939-1948, vol. 72, No. 3.

Lin, H. et al. "Metabolic engineering of aerobic succinate production systems in *Escherichia coli* to improve process productivity and achieve the maximum theoretical succinate yield" *Metabolic Engineering*, 2005, pp. 116-127, vol. 7.

Lee, E. et al. "A Highly Efficient *Escherichia coli*-Based Chromosome Engineering System Adapted for Recombinogenic Targeting and Subcloning of BAC DNA" *Genomics*, 2001, pp. 56-65, vol. 73.

Lin, H. et al. "Chemostat culture characterization of *Escherichia coli* mutant strains metabolically engineered for aerobic succinate production: A study of the modified metabolic network based on metabolite profile, enzyme activity, and gene expression profile" *Metabolic Engineering*, 2005, pp. 337-352, vol. 7.

Nilekani, S. et al. "Purification and Properties of Citrate Lyase from *Escherichia coli*" *Biochemistry*, 1983, pp. 4657-4663, vol. 22.

Martinez, A. et al. "Low salt medium for lactate and ethanol production by recombinant *Escherichia coli* B" *Biotechnol Lett*, 2007, pp. 397-404, vol. 29.

Meynial-Salles, I. et al. "A New Process for the Continuous Production of Succinic Acid from Glucose at High Yield, Titer, and Productivity" *Biotechnology and Bioengineering*, Jan. 1, 2008, pp. 129-135, vol. 99, No. 1.

McKinlay, J. B. et al. "Prospects for a bio-based succinate industry" *Applied Microbiol Biotechnol*, 2007, pp. 1-14.

Oh, M.-K. et al. "Global Expression Profiling of Acetate-grown *Escherichia coli*" *The Journal of Biological Chemistry*, Apr. 12, 2002, pp. 13175-13183, vol. 277, No. 15.

Millard, C. S. et al. "Enhanced Production of Succinic Acid by Overexpression of Phosphoenolpyruvate Carboxylase in *Escherichia coli*" *Applied and Environmental Microbiology*, May 1996, pp. 1808-1810, vol. 62, No. 5.

(56) References Cited

OTHER PUBLICATIONS

Lin, H. et al. "Effect of carbon sources differing in oxidation state and transport route on succinate production in metabolically engineered *Escherichia coli*" *J. Ind. Microbiol Biotechnol*, 2005, pp. 87-93, vol. 32.

McKinlay, J. B. et al. "$^{13}$C-metabolic flux analysis of *Actinobacillus succinogenes* fermentative metabolism at different NaHCO$_3$ and H$_2$ concentrations" *Metabolic Engineering*, 2008, pp. 55-68, vol. 10.

Martinez-Morales, F. et al. "Chromosomal Integration of Heterologous DNA in *Escherichia coli* with Precise Removal of Markers and Replicons Used during Construction" *Journal of Bacteriology*, Nov. 1999, pp. 7143-7148, vol. 181, No. 22.

Moniruzzaman, M. et al. "Extracellular Melibiose and Fructose Are Intermediates in Raffinose Catabolism during Fermentation to Ethanol by Engineered Enteric Bacteria" *Journal of Bacteriology*, Mar. 1997, pp. 1880-1886, vol. 179, No. 6.

McKinlay, J. B. et al. "Insights into *Actinobacillus succinogenes* Fermentative Metabolism in a Chemically Defined Growth Medium" *Applied and Environmental Microbiology*, Nov. 2005, pp. 6651-6656, vol. 71, No. 11.

Posfai, G. et al. "Versatile Insertion Plasmids for Targeted Genome Manipulations in Bacteria: Isolation, Deletion, and Rescue of the Pathogenicity Island LEE of the *Escherichia coli* O157:H7 Genome" *Journal of Bacteriology*, Jul. 1997, pp. 4426-4428, vol. 179, No. 13.

Quentmeier, A. et al. "Reevaluation of citrate lyase from *Escherichia coli*" *Biochimica et Biophysica Acta*, 1987, pp. 60-65, vol. 913.

Reed, J. L. et al. "An expanded genome-scale model of *Escherichia coli* K-12 (iJR904GSM/GPR)" *Genome Biology*, 2003, pp. R54-R54.12, vol. 4, Issue 9, Article R54.

Keseler, I. M. et al. "EcoCyc: a comprehensive database resource for *Escherichia coli*" *Nucleic Acids Research*, 2005, pp. D334-D337, vol. 33.

Okino, S. et al. "Production of organic acids by *Corynebacterium glutamicum* under oxygen deprivation" *Appl Microbiol Biotechnol*, 2005, pp. 475-480, vol. 68.

Stols, L. et al. "Production of Succinic Acid through Overexpression of NAD$^+$—Dependent Malic Enzyme in an *Escherichia coli* Mutant" *Applied and Environmental Microbiology*, Jul. 1997, pp. 2695-2701, vol. 63, No. 7.

Zeikus, J. G. et al. "Biotechnology of succinic acid production and markets for derived industrial products" *Appl Microbiol Biotechnol*, 1999, pp. 545-552, vol. 51.

Zhou, S. et al. "Betaine tripled the volumetric productivity of D(−)-lactate by *Escherichia coli* strain SZ132 in mineral salts medium" *Biotechnology Letters*, 2006, pp. 671-676, vol. 28.

Underwood, S. A. et al. "Genetic Changes to Optimize Carbon Partitioning between Ethanol and Biosynthesis in Ethanologenic *Escherichia coli*" *Applied and Environmental Microbiology*, Dec. 2002, pp. 6263-6272, vol. 68, No. 12.

Zhang, X. et al. "Production of L-alanine by metabolically engineered *Escherichia coli*" *Appl Microbiol Biotechnol*, 2007, pp. 1-12.

Reitzer, L. Chapter 3.6.1.3, Biosynthesis of Glutamate, Aspartate, Asparagine, L-Alanine, and D-Alanine, A. Böck, R. Curtiss III, J. B. Kaper, F. C. Neidhardt, T. Nyström, K. E. Rudd, and C. L. Squires (ed.), EcoSal—*Escherichia coli* and *Salmonella*: Cellular and Molecular Biology. [Online.] http://www.ecosal.org. ASM Press, Washington, D.C., Jul. 6, 2004, posting date.

Unden, G. et al. "C$_4$-Dicarboxylate Degradation in Aerobic and Anaerobic Growth" *EcoSal Module 3.4.5*, 2006, pp. 1-15, ASM Press.

Sawers, G. et al. "Anaerobic Regulation of Pyruvate Formate-Lyase from *Escherichia coli* K-12" *Journal of Bacteriology*, Nov. 1988, pp. 5330-5336, vol. 170, No. 11.

Sanwal, B. D. "Regulatory Mechanisms Involving Nicotinamide Adenine Nucleotides as Allosteric Effectors" *The Journal of Biological Chemistry*, Apr. 10, 1969, pp. 1831-1837, vol. 244, No. 7.

Storici, F. et al. "A 2-µm DNA-Based Marker Recycling System for Multiple Gene Disruption in the Yeast *Saccharomyces cerevisiae*" *Yeast*, 1999, pp. 271-283, vol. 15.

Sanwal, B. D. "Regulatory Characteristics of the Diphosphopyridine Nucleotide-specific Malic Enzyme of *Escherichia coli*" *The Journal of Biological Chemistry*, Mar. 10, 1970, pp. 1212-1216, vol. 245, No. 5.

Sanwal, B. D. "Allosteric Controls of Amphibolic Pathways in Bacteria" *Bacteriological Reviews*, Mar. 1970, pp. 20-39, vol. 34, No. 1.

Sanwal, B. D. et al. "Malic Enzyme of *Escherichia coli*: Diversity of the Effectors Controlling Enzyme Activity" *The Journal of Biological Chemistry*, Apr. 10, 1969, pp. 1817-1823, vol. 244, No. 7.

Sanchez, A. M. et al. "Batch culture characterization and metabolic flux analysis of succinate-producing *Escherichia coli* strains" *Metabolic Engineering*, 2006, pp. 209-226, vol. 8.

Sanchez, A. M. et al. "Novel pathway engineering design of the anaerobic central metabolic pathway in *Escherichia coli* to increase succinate yield and productivity" *Metabolic Engineering*, 2005, pp. 229-239, vol. 7.

Sanchez, A. M. et al. "Efficient Succinic Acid Production from Glucose through Overexpression of Pyruvate Carboxylase in an *Escherichia coli* Alcohol Dehydrogenase and Lactate Dehydrogenase Mutant" *Biotechnol. Prog.*, 2005, pp. 358-365, vol. 21.

Samuelov, N. S. et al. "Influence of $CO_2$—$HCO_3$ Levels and pH on Growth, Succinate Production, and Enzyme Activities of *Anaerobiospirillum succiniciproducens*" *Applied and Environmental Microbiology*, Oct. 1991, pp. 3013-3019, vol. 57, No. 10.

Yun, N.-R. et al. "Enhancement of lactate and succinate formation in *adhE* or *pta-ackA* mutants of NADH dehydrogenase-deficient *Escherichia coli*" *Journal of Applied Microbiology*, 2005, pp. 1404-1412, vol. 99.

Wright, J. A. et al. "Regulatory Mechanisms Involving Nicotinamide Adenine Nucleotides as Allosteric Effectors" *The Journal of Biological Chemistry*, Apr. 10, 1969, pp. 1838-1845, vol. 244, No. 7.

Wood, B. E. et al. "Development of Industrial-Medium-Required Elimination of the 2,3-Butanediol Fermentation Pathway to Maintain Ethanol Yield in an Ethanologenic Strain of *Klebsiella oxytoca*" *Biotechnol. Prog.*, 2005, pp. 1366-1372, vol. 21.

Vemuri, G. N. et al. "Effects of Growth Mode and Pyruvate Carboxylase on Succinic Acid Production by Metabolically Engineered Strains of *Escherichia coli*" *Applied and Environmental Microbiology*, Apr. 2002, pp. 1715-1727, vol. 68, No. 4.

Vemuri, G. N. et al. "Succinate production in dual-phase *Escherichia coli* fermentations depends on the time of transition from aerobic to anaerobic conditions" *Journal of Industrial Microbiology & Biotechnology*, 2002, pp. 325-332, vol. 28.

Wendisch, V. F. "Metabolic engineering of *Escherichia coli* and *Corynebacterium glutamicum* for biotechnological production of organic acids and amino acids" *Current Opinion in Microbiology*, 2006, pp. 268-274, vol. 9.

Van Der Werf, M. J. "Environmental and physiological factors affecting the succinate product ratio during carbohydrate fermentation by *Actinobacillus sp. 130Z*" *Arch Microbiol*, 1997, pp. 332-342, vol. 167.

Song, H. et al. "Effects of Dissolved $CO_2$ Levels on the Growth of *Mannheimia succiniciproducens* and Succinic Acid Production" *Biotechnology and Bioengineering*, Dec. 15, 2007, pp. 1296-1304, vol. 98, No. 6.

Underwood, S. A. et al. "Lack of Protective Osmolytes Limits Final Cell Density and Volumetric Productivity of Ethanologenic *Escherichia coli* KO11 during Xylose Fermentation" *Applied and Environmental Microbiology*, May 2004, pp. 2734-2740, vol. 70, No. 5.

Thomason, L. et al. "Recombineering: Genetic Engineering in Bacteria Using Homologous Recombination" *Current Protocols in Molecular Biology*, 2007, pp. 1.16.1-1.16.24, Supplement 78.

Krebs, A. et al. "The kinetic properties of phosphoenolpyruvate carboxykinase of *Escherichia coli*" *Can. J. Biochem.*, 1979, pp. 309-318, vol. 58.

Izui, K. et al. "Regulation of *Escherichia coli* Phosphoenolpyruvate Carboxylase by Multiple Effectors In Vivo. II. Kinetic Studies with a Reaction System Containing Physiological Concentration of Ligands" *J. Biochem.*, 1981, pp. 1321-1331, vol. 90.

Gottschalk, G., Bacterial Metabolism, 1985, 2nd ed. Springer-Verlag, New York.

(56) References Cited

OTHER PUBLICATIONS

Causey, T. B. et al. "Engineering the metabolism of *Escherichia coli* W3110 for the conversion of sugar to redox-neutral and oxidized products: Homoacetate production" *PNAS*, Feb. 4, 2003, pp. 825-832, vol. 100, No. 3.

Zhou, S. et al. "Production of Optically Pure D-Lactic Acid in Mineral Salts Medium by Metabolically Engineered *Escherichia coli* W3110" *Applied and Environmental Microbiology*, Jan. 2003, pp. 399-407, vol. 69, No. 1.

Karp, P. D. et al. "Multidimensional annotation of the *Escherichia coli* K-12 genome" *Nucleic Acids Research*, 2007, pp. 7577-7590, vol. 35, No. 22.

Sanwal, B. D. et al. "Malic Enzyme of *Escherichia coli*: Possible Mechanism for Allosteric Effects" *The Journal of Biological Chemistry*, Apr. 10, 1969, pp. 1824-1830, vol. 244, No. 7.

Written Opinion in International Application No. PCT/US2008/057439, Dec. 18, 2008, pp. 1-5.

Andersson, C. et al. "Effect of Different Carbon Sources on the Production of Succinic Acid Using Metabolically Engineered *Escherichia coli*" *Biotechnol. Prog.*, 2007, pp. 381-388, vol. 23.

Bekal, S. et al. "Purification of *Leuconostoc mesenteroides* Citrate Lyase and Cloning and Characterization of the *citCDEFG* Gene Cluster" *Journal of Bacteriology*, Feb. 1998, pp. 647-654, vol. 180, No. 3.

* cited by examiner

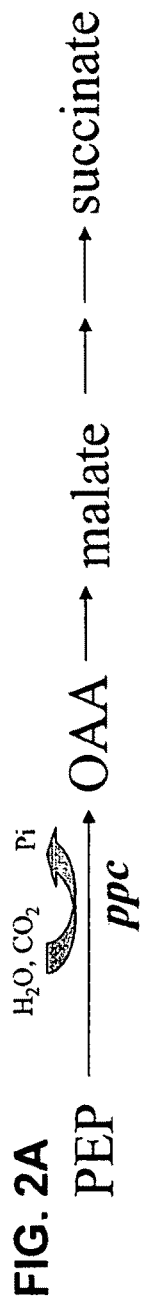
FIG. 2A  PEP →(H₂O, CO₂, Pi / ppc)→ OAA → malate → succinate
FIG. 2B  PEP →(ADP, ATP / pyk)→ pyruvate →(CO₂, NADH, NAD⁺ / sfcA)→ malate → succinate
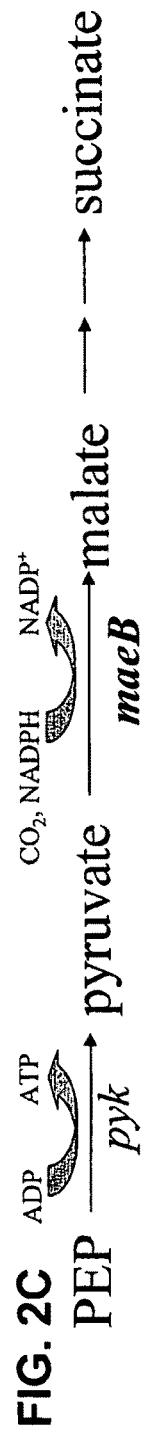
FIG. 2C  PEP →(ADP, ATP / pyk)→ pyruvate →(CO₂, NADPH, NADP⁺ / maeB)→ malate → succinate
FIG. 2D  PEP →(CO₂, ADP, ATP / pck)→ OAA → malate → succinate

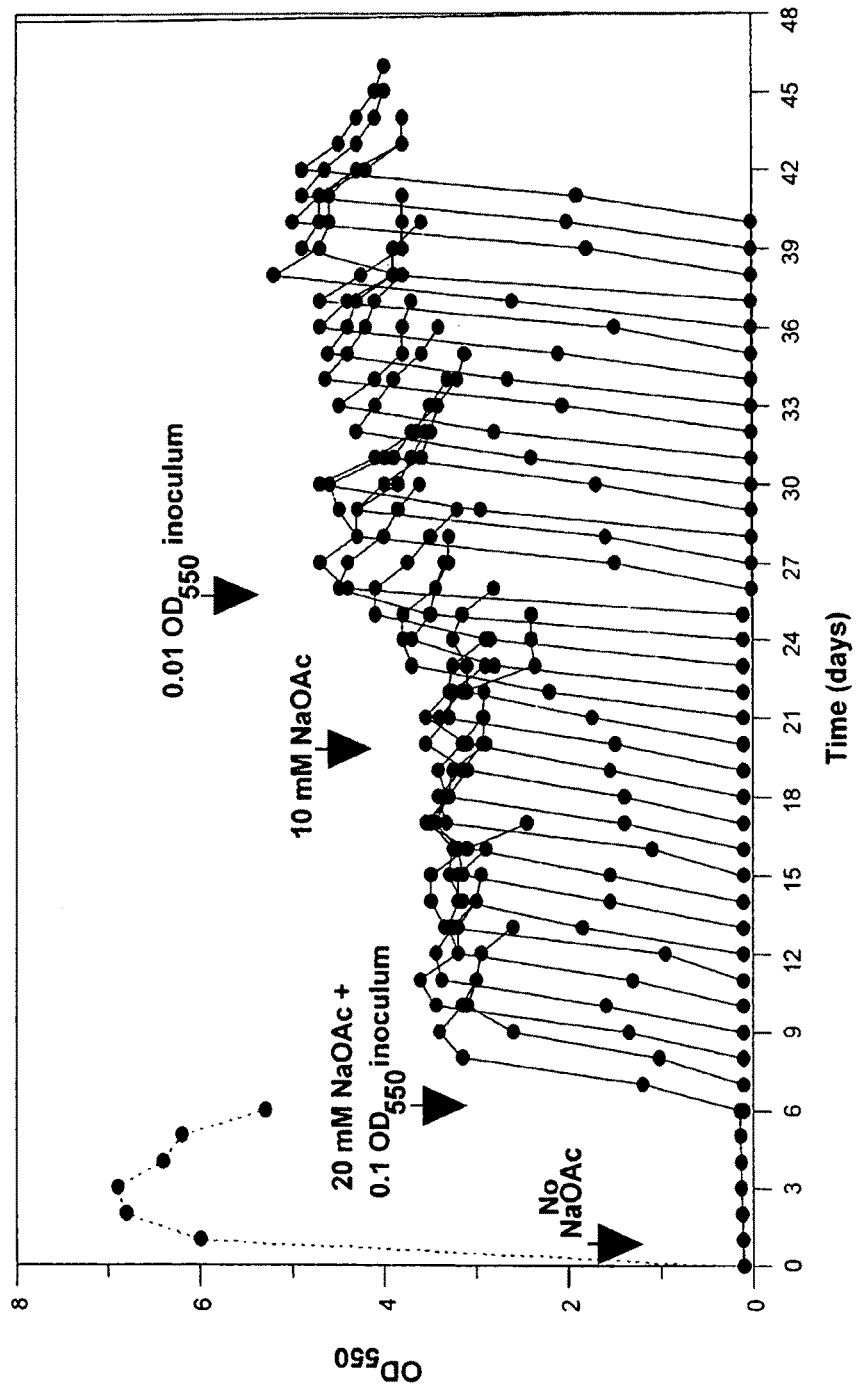

Construction of pLOI4162

SEQUENCE LISTING

```
<160> NUMBER OF SEQ ID NOS: 77

<210> SEQ ID NO 1
<211> LENGTH: 18
<212> TYPE: DNA
<213> ORGANISM: Artificial sequence
<220> FEATURE:
<223> OTHER INFORMATION: completely synthesized translational stop
      sequence

<400> SEQUENCE: 1
gcctaattaa ttaatccc                                                 18

<210> SEQ ID NO 2
<211> LENGTH: 65
<212> TYPE: DNA
<213> ORGANISM: Artificial sequence
<220> FEATURE:
<223> OTHER INFORMATION: Primer set for ldhA

<400> SEQUENCE: 2
atgaactcgc cgttttatag cacaaaacag tacgacaaga agtacgtgta ggctggagct      60
gcttc                                                                 65

<210> SEQ ID NO 3
<211> LENGTH: 65
<212> TYPE: DNA
<213> ORGANISM: Artificial sequence
<220> FEATURE:
<223> OTHER INFORMATION: Primer set for ldhA

<400> SEQUENCE: 3
ttaaaccagt tcgttcgggc aggtttcgcc tttttccaga ttgctcatat gaatatcctc      60
cttag                                                                 65

<210> SEQ ID NO 4
<211> LENGTH: 65
<212> TYPE: DNA
<213> ORGANISM: Artificial sequence
<220> FEATURE:
<223> OTHER INFORMATION: Primer set for adhE
```

-continued

```
<400> SEQUENCE: 4
atggctgtta ctaatgtcgc tgaacttaac gcactcgtag agcgtgtgta ggctggagct    60
gcttc                                                                65

<210> SEQ ID NO 5
<211> LENGTH: 65
<212> TYPE: DNA
<213> ORGANISM: Artificial sequence
<220> FEATURE:
<223> OTHER INFORMATION: Primer set for adhE

<400> SEQUENCE: 5
ttaagcggat ttttcgctt ttttctcagc tttagccgga gcagccatat gaatatcctc    60
cttag                                                                65

<210> SEQ ID NO 6
<211> LENGTH: 65
<212> TYPE: DNA
<213> ORGANISM: Artificial sequence
<220> FEATURE:
<223> OTHER INFORMATION: Primer set for ackA

<400> SEQUENCE: 6
atgtcgagta agttagtact ggttctgaac tgcggtagtt cttcagtgta ggctggagct    60
gcttc                                                                65

<210> SEQ ID NO 7
<211> LENGTH: 65
<212> TYPE: DNA
<213> ORGANISM: Artificial sequence
<220> FEATURE:
<223> OTHER INFORMATION: Primer set for ackA

<400> SEQUENCE: 7
tcaggcagtc aggcggctcg cgtcttgcgc gataaccagt tcttccatat gaatatcctc    60
cttag                                                                65

<210> SEQ ID NO 8
<211> LENGTH: 65
<212> TYPE: DNA
<213> ORGANISM: Artificial sequence
<220> FEATURE:
<223> OTHER INFORMATION: Primer set for focA-plfB

<400> SEQUENCE: 8
ttactccgta tttgcataaa aaccatgcga gttacgggcc tataagtgta ggctggagct    60
gcttc                                                                65

<210> SEQ ID NO 9
<211> LENGTH: 65
<212> TYPE: DNA
<213> ORGANISM: Artificial sequence
<220> FEATURE:
<223> OTHER INFORMATION: Primer set for focA-plfB

<400> SEQUENCE: 9
atagattgag tgaaggtacg agtaataacg tcctgctgct gttctcatat gaatatcctc    60
cttag                                                                65
```

```
<210> SEQ ID NO 10
<211> LENGTH: 30
<212> TYPE: DNA
<213> ORGANISM: Artificial sequence
<220> FEATURE:
<223> OTHER INFORMATION: Primer set for JMcatsacB

<400> SEQUENCE: 10
ttagctagca tgtgacggaa gatcacttcg                                30

<210> SEQ ID NO 11
<211> LENGTH: 31
<212> TYPE: DNA
<213> ORGANISM: Artificial sequence
<220> FEATURE:
<223> OTHER INFORMATION: Primer set for JMcatsacB

<400> SEQUENCE: 11
ccgctagcat caaagggaaa actgtccata t                              31

<210> SEQ ID NO 12
<211> LENGTH: 32
<212> TYPE: DNA
<213> ORGANISM: Artificial sequence
<220> FEATURE:
<223> OTHER INFORMATION: Primer set for cat-up2/sacB-down2

<400> SEQUENCE: 12
agagaggata tctgtgacgg aagatcactt cg                             32

<210> SEQ ID NO 13
<211> LENGTH: 32
<212> TYPE: DNA
<213> ORGANISM: Artificial sequence
<220> FEATURE:
<223> OTHER INFORMATION: Primer set for cat-up2/sacB-down2

<400> SEQUENCE: 13
agagaggata tcgaattgat ccggtggatg ac                             32

<210> SEQ ID NO 14
<211> LENGTH: 20
<212> TYPE: DNA
<213> ORGANISM: Artificial sequence
<220> FEATURE:
<223> OTHER INFORMATION: Primer set for mgsA-up/down

<400> SEQUENCE: 14
cagctcatca accaggtcaa                                           20

<210> SEQ ID NO 15
<211> LENGTH: 20
<212> TYPE: DNA
<213> ORGANISM: Artificial sequence
<220> FEATURE:
<223> OTHER INFORMATION: Primer set for mgsA-up/down

<400> SEQUENCE: 15
aaaagccgtc acgttattgg                                           20

<210> SEQ ID NO 16
<211> LENGTH: 20
<212> TYPE: DNA
<213> ORGANISM: Artificial sequence
<220> FEATURE:
<223> OTHER INFORMATION: Primer set for mgsA-1/2
```

<400> SEQUENCE: 16
agcgttatct cgcggaccgt                                           20

<210> SEQ ID NO 17
<211> LENGTH: 20
<212> TYPE: DNA
<213> ORGANISM: Artificial sequence
<220> FEATURE:
<223> OTHER INFORMATION: Primer set for mgsA-1/2

<400> SEQUENCE: 17
aagtgcgagt cgtcagttcc                                           20

<210> SEQ ID NO 18
<211> LENGTH: 20
<212> TYPE: DNA
<213> ORGANISM: Artificial sequence
<220> FEATURE:
<223> OTHER INFORMATION: Primer set for poxB-up/down

<400> SEQUENCE: 18
aagcaataac gttccggttg                                           20

<210> SEQ ID NO 19
<211> LENGTH: 20
<212> TYPE: DNA
<213> ORGANISM: Artificial sequence
<220> FEATURE:
<223> OTHER INFORMATION: Primer set for poxB-up/down

<400> SEQUENCE: 19
ccactttatc cagcggtagc                                           20

<210> SEQ ID NO 20
<211> LENGTH: 19
<212> TYPE: DNA
<213> ORGANISM: Artificial sequence
<220> FEATURE:
<223> OTHER INFORMATION: Primer set for poxB-1/2

<400> SEQUENCE: 20
gacgcggtga tgaagtgat                                            19

<210> SEQ ID NO 21
<211> LENGTH: 20
<212> TYPE: DNA
<213> ORGANISM: Artificial sequence
<220> FEATURE:
<223> OTHER INFORMATION: Primer set for poxB-1/2

<400> SEQUENCE: 21
tttggcgata taagctgcaa                                           20

<210> SEQ ID NO 22
<211> LENGTH: 29
<212> TYPE: DNA
<213> ORGANISM: Artificial sequence
<220> FEATURE:
<223> OTHER INFORMATION: Primer set for pck-F/R

<400> SEQUENCE: 22
ttggctaagg agcagtgaaa tgcgcgtta                                 29

-continued

```
<210> SEQ ID NO 23
<211> LENGTH: 25
<212> TYPE: DNA
<213> ORGANISM: Artificial sequence
<220> FEATURE:
<223> OTHER INFORMATION: Primer set for pck-F/R

<400> SEQUENCE: 23
cacgacaaaa gaagggtaaa taaac                                          25

<210> SEQ ID NO 24
<211> LENGTH: 20
<212> TYPE: DNA
<213> ORGANISM: Artificial sequence
<220> FEATURE:
<223> OTHER INFORMATION: Primer set for pck-2/3

<400> SEQUENCE: 24
ttgttaacgc gcatttcact                                                20

<210> SEQ ID NO 25
<211> LENGTH: 20
<212> TYPE: DNA
<213> ORGANISM: Artificial sequence
<220> FEATURE:
<223> OTHER INFORMATION: Primer set for pck-2/3

<400> SEQUENCE: 25
gcgatagcgg ctactgtcat                                                20

<210> SEQ ID NO 26
<211> LENGTH: 18
<212> TYPE: DNA
<213> ORGANISM: Artificial sequence
<220> FEATURE:
<223> OTHER INFORMATION: Primer set for pck (RT-PCR)

<400> SEQUENCE: 26
gacgatacca ctcgcgat                                                  18

<210> SEQ ID NO 27
<211> LENGTH: 19
<212> TYPE: DNA
<213> ORGANISM: Artificial sequence
<220> FEATURE:
<223> OTHER INFORMATION: Primer set for pck (RT-PCR)

<400> SEQUENCE: 27
gtcgacaacg aacagacgt                                                 19

<210> SEQ ID NO 28
<211> LENGTH: 17
<212> TYPE: DNA
<213> ORGANISM: Artificial sequence
<220> FEATURE:
<223> OTHER INFORMATION: Primer set for birA (RT-PCR)

<400> SEQUENCE: 28
atcgtgatgg cggaagt                                                   17

<210> SEQ ID NO 29
<211> LENGTH: 19
<212> TYPE: DNA
<213> ORGANISM: Artificial sequence
<220> FEATURE:
<223> OTHER INFORMATION: Primer set for birA (RT-PCR)
```

```
<400> SEQUENCE: 29
cttgcgatcc tgcagatag                                                 19

<210> SEQ ID NO 30
<211> LENGTH: 32
<212> TYPE: DNA
<213> ORGANISM: Artificial sequence
<220> FEATURE:
<223> OTHER INFORMATION: Primer set for JM4161 sense/comp

<400> SEQUENCE: 30
accgcatcag gcgcctaatt aattaatccc gg                                  32

<210> SEQ ID NO 31
<211> LENGTH: 32
<212> TYPE: DNA
<213> ORGANISM: Artificial sequence
<220> FEATURE:
<223> OTHER INFORMATION: Primer set for JM4161 sense/comp

<400> SEQUENCE: 31
ccgggattaa ttaattaggc gcctgatgcg gt                                  32

<210> SEQ ID NO 32
<211> LENGTH: 30
<212> TYPE: DNA
<213> ORGANISM: Artificial sequence
<220> FEATURE:
<223> OTHER INFORMATION: Primer set for JMpEL04F1/R1

<400> SEQUENCE: 32
cagcagatct aagtaaatcg cgcgggtttg                                     30

<210> SEQ ID NO 33
<211> LENGTH: 30
<212> TYPE: DNA
<213> ORGANISM: Artificial sequence
<220> FEATURE:
<223> OTHER INFORMATION: Primer set for JMpEL04F1/R1

<400> SEQUENCE: 33
cagcagatct agcggctatt taacgaccct                                     30

<210> SEQ ID NO 34
<211> LENGTH: 20
<212> TYPE: DNA
<213> ORGANISM: Artificial sequence
<220> FEATURE:
<223> OTHER INFORMATION: Primer set for JMackA-F1/R1

<400> SEQUENCE: 34
gcctgaaggc ctaagtagta                                                20

<210> SEQ ID NO 35
<211> LENGTH: 20
<212> TYPE: DNA
<213> ORGANISM: Artificial sequence
<220> FEATURE:
<223> OTHER INFORMATION: Primer set for JMackA-F1/R1

<400> SEQUENCE: 35
gcacgatagt cgtagtctga                                                20
```

```
<210> SEQ ID NO 36
<211> LENGTH: 20
<212> TYPE: DNA
<213> ORGANISM: Artificial sequence
<220> FEATURE:
<223> OTHER INFORMATION: Primer set for JMackA up1/down1

<400> SEQUENCE: 36
gttgagcgct tcgctgtgag                                               20

<210> SEQ ID NO 37
<211> LENGTH: 20
<212> TYPE: DNA
<213> ORGANISM: Artificial sequence
<220> FEATURE:
<223> OTHER INFORMATION: Primer set for JMackA up1/down1

<400> SEQUENCE: 37
gccgcaatgg ttcgtgaact                                               20

<210> SEQ ID NO 38
<211> LENGTH: 31
<212> TYPE: DNA
<213> ORGANISM: Artificial sequence
<220> FEATURE:
<223> OTHER INFORMATION: Primer set for JMcatsacB up3/down3

<400> SEQUENCE: 38
ctcacctcga gtgtgacgga agatcacttc g                                  31

<210> SEQ ID NO 39
<211> LENGTH: 34
<212> TYPE: DNA
<213> ORGANISM: Artificial sequence
<220> FEATURE:
<223> OTHER INFORMATION: Primer set for JmcatsacB up3/down3

<400> SEQUENCE: 39
gtgcaggatc catcaaaggg aaaactgtcc atat                               34

<210> SEQ ID NO 40
<211> LENGTH: 59
<212> TYPE: DNA
<213> ORGANISM: Artificial sequence
<220> FEATURE:
<223> OTHER INFORMATION: Primer set for SfPBXPS sense/comp

<400> SEQUENCE: 40
atgtaggcgc cattaattaa tggatccact atctcgagat taattaatcc cgggactat    59

<210> SEQ ID NO 41
<211> LENGTH: 59
<212> TYPE: DNA
<213> ORGANISM: Artificial sequence
<220> FEATURE:
<223> OTHER INFORMATION: Primer set for SfPBXPS sense/comp

<400> SEQUENCE: 41
atagtcccgg gattaattaa tctcgagata gtggatccat taattaatgg cgcctacat    59

<210> SEQ ID NO 42
<211> LENGTH: 65
<212> TYPE: DNA
<213> ORGANISM: Artificial sequence
<220> FEATURE:
<223> OTHER INFORMATION: Primer set for WMadhE A/C
```

-continued

<400> SEQUENCE: 42
atggctgtta ctaatgtcgc tgaacttaac gcactcgtag agcgtcggca cgtaagaggt    60
tccaa    65

<210> SEQ ID NO 43
<211> LENGTH: 65
<212> TYPE: DNA
<213> ORGANISM: Artificial sequence
<220> FEATURE:
<223> OTHER INFORMATION: Primer set for WMadhE A/C

<400> SEQUENCE: 43
ttaagcggat tttttcgctt ttttctcagc tttagccgga gcagcacact gcttccggta    60
gtcaa    65

<210> SEQ ID NO 44
<211> LENGTH: 64
<212> TYPE: DNA
<213> ORGANISM: Artificial sequence
<220> FEATURE:
<223> OTHER INFORMATION: Primer set for WMldhA A/C

<400> SEQUENCE: 44
atgaaactcg ccgtttatag cacaaaacag tacgacaaga agtacggcac gtaagaggtt    60
ccaa    64

<210> SEQ ID NO 45
<211> LENGTH: 65
<212> TYPE: DNA
<213> ORGANISM: Artificial sequence
<220> FEATURE:
<223> OTHER INFORMATION: Primer set for WMldhA A/C

<400> SEQUENCE: 45
ttaaaccagt tcgttcgggc aggtttcgcc ttttccaga ttgctacact gcttccggta    60
gtcaa    65

<210> SEQ ID NO 46
<211> LENGTH: 65
<212> TYPE: DNA
<213> ORGANISM: Artificial sequence
<220> FEATURE:
<223> OTHER INFORMATION: Primer set for WMpflB A/C

<400> SEQUENCE: 46
ttactccgta tttgcataaa aaccatgcga gttacgggcc tataacggca cgtaagaggt    60
tccaa    65

<210> SEQ ID NO 47
<211> LENGTH: 69
<212> TYPE: DNA
<213> ORGANISM: Artificial sequence
<220> FEATURE:
<223> OTHER INFORMATION: Primer set for WMpflB A/C

<400> SEQUENCE: 47
ttacatagat tgagtgaagg tacgagtaat aacgtcctgc tgctgttcta cactgcttcc    60
ggtagtcaa    69

```
<210> SEQ ID NO 48
<211> LENGTH: 20
<212> TYPE: DNA
<213> ORGANISM: Artificial sequence
<220> FEATURE:
<223> OTHER INFORMATION: Primer set for tdcDE-up/down

<400> SEQUENCE: 48
cgccgacaga gtaataggtt                                              20

<210> SEQ ID NO 49
<211> LENGTH: 20
<212> TYPE: DNA
<213> ORGANISM: Artificial sequence
<220> FEATURE:
<223> OTHER INFORMATION: Primer set for tdcDE-up/down

<400> SEQUENCE: 49
tgatgagcta cctggtatgg                                              20

<210> SEQ ID NO 50
<211> LENGTH: 20
<212> TYPE: DNA
<213> ORGANISM: Artificial sequence
<220> FEATURE:
<223> OTHER INFORMATION: Primer set for tdcDE-F7/R7

<400> SEQUENCE: 50
cgatgcggtg gccaattaag                                              20

<210> SEQ ID NO 51
<211> LENGTH: 20
<212> TYPE: DNA
<213> ORGANISM: Artificial sequence
<220> FEATURE:
<223> OTHER INFORMATION: Primer set for tdcDE-F7/R7

<400> SEQUENCE: 51
gacgacgtgc tggattacga                                              20

<210> SEQ ID NO 52
<211> LENGTH: 20
<212> TYPE: DNA
<213> ORGANISM: Artificial sequence
<220> FEATURE:
<223> OTHER INFORMATION: Primer set for citF-up2/down2

<400> SEQUENCE: 52
gggtattcag gcgttcgata                                              20

<210> SEQ ID NO 53
<211> LENGTH: 20
<212> TYPE: DNA
<213> ORGANISM: Artificial sequence
<220> FEATURE:
<223> OTHER INFORMATION: Primer set for citF-up2/down2

<400> SEQUENCE: 53
gcccgagagg atgactatgt                                              20

<210> SEQ ID NO 54
<211> LENGTH: 20
<212> TYPE: DNA
<213> ORGANISM: Artificial sequence
<220> FEATURE:
<223> OTHER INFORMATION: Primer set for citF-2/3
```

```
<400> SEQUENCE: 54
ggtgatcgat gttgtgcatc                                           20

<210> SEQ ID NO 55
<211> LENGTH: 20
<212> TYPE: DNA
<213> ORGANISM: Artificial sequence
<220> FEATURE:
<223> OTHER INFORMATION: Primer set for citF-2/3

<400> SEQUENCE: 55
cccgttcttg tcgttgagat                                           20

<210> SEQ ID NO 56
<211> LENGTH: 20
<212> TYPE: DNA
<213> ORGANISM: Artificial sequence
<220> FEATURE:
<223> OTHER INFORMATION: Primer set for IO-adhE-up/down

<400> SEQUENCE: 56
gctgctccgg ctaaagctga                                           20

<210> SEQ ID NO 57
<211> LENGTH: 20
<212> TYPE: DNA
<213> ORGANISM: Artificial sequence
<220> FEATURE:
<223> OTHER INFORMATION: Primer set for IO-adhE-up/down

<400> SEQUENCE: 57
acgctctacg agtgcgttaa                                           20

<210> SEQ ID NO 58
<211> LENGTH: 20
<212> TYPE: DNA
<213> ORGANISM: Artificial sequence
<220> FEATURE:
<223> OTHER INFORMATION: Primer set for up-focA/Mid-pflB

<400> SEQUENCE: 58
agatcgccag ccgctgcaat                                           20

<210> SEQ ID NO 59
<211> LENGTH: 20
<212> TYPE: DNA
<213> ORGANISM: Artificial sequence
<220> FEATURE:
<223> OTHER INFORMATION: Primer set for up-focA/Mid-pflB

<400> SEQUENCE: 59
aaccgttggt gtccagacag                                           20

<210> SEQ ID NO 60
<211> LENGTH: 20
<212> TYPE: DNA
<213> ORGANISM: Artificial sequence
<220> FEATURE:
<223> OTHER INFORMATION: Primer set for IO-ycaO-up/IO-midpflB-down

<400> SEQUENCE: 60
gcctacattg cgtaggctat                                           20
```

```
<210> SEQ ID NO 61
<211> LENGTH: 20
<212> TYPE: DNA
<213> ORGANISM: Artificial sequence
<220> FEATURE:
<223> OTHER INFORMATION: Primer set for IO-ycaO-up/IO-midpflB-down

<400> SEQUENCE: 61
gcagcaggac gttattactc                                               20

<210> SEQ ID NO 62
<211> LENGTH: 20
<212> TYPE: DNA
<213> ORGANISM: Artificial sequence
<220> FEATURE:
<223> OTHER INFORMATION: Primer set for ldhA-A/C

<400> SEQUENCE: 62
atgaaactcg ccgtttatag                                               20

<210> SEQ ID NO 63
<211> LENGTH: 19
<212> TYPE: DNA
<213> ORGANISM: Artificial sequence
<220> FEATURE:
<223> OTHER INFORMATION: Primer set for ldhA-A/C

<400> SEQUENCE: 63
ttaaaccagt tcgttgccc                                                19

<210> SEQ ID NO 64
<211> LENGTH: 20
<212> TYPE: DNA
<213> ORGANISM: Artificial sequence
<220> FEATURE:
<223> OTHER INFORMATION: Primer set for IO/ldhA-up/down

<400> SEQUENCE: 64
cgttcgatcc gtatccaagt                                               20

<210> SEQ ID NO 65
<211> LENGTH: 20
<212> TYPE: DNA
<213> ORGANISM: Artificial sequence
<220> FEATURE:
<223> OTHER INFORMATION: Primer set for IO-ldhA-up/down

<400> SEQUENCE: 65
aggctggaac tcggactact                                               20

<210> SEQ ID NO 66
<211> LENGTH: 20
<212> TYPE: DNA
<213> ORGANISM: Artificial sequence
<220> FEATURE:
<223> OTHER INFORMATION: Primer set for aspC-up/down

<400> SEQUENCE: 66
tccatcgctt acaccaaatc                                               20

<210> SEQ ID NO 67
<211> LENGTH: 20
<212> TYPE: DNA
<213> ORGANISM: Artificial sequence
<220> FEATURE:
<223> OTHER INFORMATION: Primer set for aspC-up/down
```

```
<400> SEQUENCE: 67
tgggggatga cgtgatattt                                               20

<210> SEQ ID NO 68
<211> LENGTH: 20
<212> TYPE: DNA
<213> ORGANISM: Artificial sequence
<220> FEATURE:
<223> OTHER INFORMATION: Primer set for aspC-1/2

<400> SEQUENCE: 68
agataacatg gctccgctgt                                               20

<210> SEQ ID NO 69
<211> LENGTH: 19
<212> TYPE: DNA
<213> ORGANISM: Artificial sequence
<220> FEATURE:
<223> OTHER INFORMATION: Primer set for aspC-1/2

<400> SEQUENCE: 69
aggagcggcg gtaatgttc                                                19

<210> SEQ ID NO 70
<211> LENGTH: 20
<212> TYPE: DNA
<213> ORGANISM: Artificial sequence
<220> FEATURE:
<223> OTHER INFORMATION: Primer set for sfcA-up/down

<400> SEQUENCE: 70
ctatgcttga tcggcaacct                                               20

<210> SEQ ID NO 71
<211> LENGTH: 20
<212> TYPE: DNA
<213> ORGANISM: Artificial sequence
<220> FEATURE:
<223> OTHER INFORMATION: Primer set for sfcA-up/down

<400> SEQUENCE: 71
acgatcgcct ggttttaatg                                               20

<210> SEQ ID NO 72
<211> LENGTH: 20
<212> TYPE: DNA
<213> ORGANISM: Artificial sequence
<220> FEATURE:
<223> OTHER INFORMATION: Primer set for sfcA-1/2

<400> SEQUENCE: 72
taccgccgta cctccatcta                                               20

<210> SEQ ID NO 73
<211> LENGTH: 22
<212> TYPE: DNA
<213> ORGANISM: Artificial sequence
<220> FEATURE:
<223> OTHER INFORMATION: Primer set for sfcA-1/2

<400> SEQUENCE: 73
cgtaagggat ataaagcgaa cg                                            22
```

```
<210> SEQ ID NO 74
<211> LENGTH: 20
<212> TYPE: DNA
<213> ORGANISM: Artificial sequence
<220> FEATURE:
<223> OTHER INFORMATION: Primer set for ackA-up/pta-down

<400> SEQUENCE: 74
cgggacaacg ttcaaaacat                                            20

<210> SEQ ID NO 75
<211> LENGTH: 20
<212> TYPE: DNA
<213> ORGANISM: Artificial sequence
<220> FEATURE:
<223> OTHER INFORMATION: Primer set for ackA-up/pta-down

<400> SEQUENCE: 75
attgcccatc ttcttgttgg                                            20

<210> SEQ ID NO 76
<211> LENGTH: 21
<212> TYPE: DNA
<213> ORGANISM: Artificial sequence
<220> FEATURE:
<223> OTHER INFORMATION: Primer set for ackA-2/pta-2

<400> SEQUENCE: 76
aactaccgca gttcagaacc a                                          21

<210> SEQ ID NO 77
<211> LENGTH: 20
<212> TYPE: DNA
<213> ORGANISM: Artificial sequence
<220> FEATURE:
<223> OTHER INFORMATION: Primer set for ackA-2/pta-2

<400> SEQUENCE: 77
tctgaacacc ggtaacacca                                            20
```

MATERIALS AND METHODS FOR EFFICIENT SUCCINATE AND MALATE PRODUCTION

CROSS-REFERENCE TO RELATED APPLICATION

This application is the U.S. national stage application of International Patent Application No. PCT/US2008/057439, filed Mar. 19, 2008, which claims the benefit of U.S. Provisional Application Ser. No. 60/895,806, filed Mar. 20, 2007, the disclosures of which are hereby incorporated by reference in their entirety, including all figures, tables and amino acid or nucleic acid sequences.

GOVERNMENT SUPPORT

This invention was made with government support under a grant awarded from the Department of Energy under grant number USDOE-DE FG02-96ER20222 and Department of Energy in conjunction with the United States Department of Agriculture under grant number USDA & DOE Biomass RDI DE FG36-04GO14019. The government has certain rights in the invention.

BACKGROUND OF THE INVENTION

The fermentative production of succinate from renewable feedstocks will become increasingly competitive as petroleum prices increase. Succinate can serve as a substrate for transformation into plastics, solvents, and other chemicals currently made from petroleum (Lee et al., 2004; Lee et al., 2005; McKinlay et al., 2007; Wendisch et al., 2006; Zeikus et al., 1999). Many bacteria have been described with the natural ability to produce succinate as a major fermentation product (U.S. Pat. No. 5,723,322; Table 1). However, complex processes, complex media and long incubation times are often required.

A variety of genetic approaches have previously been used to engineer *Escherichia coli* strains for succinate production with varying degrees of success (Table 1). In most studies, titers achieved were low and complex medium ingredients such as yeast extract or corn steep liquor were required. Strain NZN111 produced 108 mM succinate with a molar yield of 0.98 mol succinate per mol of metabolized glucose (Chatterjee et al., 2001; Millard et al., 1996; Stols and Donnelly, 1997). This strain was engineered by inactivating two genes (pflB encoding pyruvate-formatelyase and ldhA encoding lactate dehydrogenase), and over-expressing two *E. coli* genes, malate dehydrogenase (mdh) and phosphoenolpyruvate carboxylase (ppc), from multicopy plasmids. Strain HL27659k was engineered by mutating succinate dehydrogenase (sdhAB), phosphate acetyltransferase (pta), acetate kinase (ackA), pyruvate oxidase (poxB), glucose transporter (ptsG), and the isocitrate lyase repressor (iclR). This strain produced less than 100 mM succinate and required oxygen-limited fermentation conditions (Cox et al., 2006; Lin et al., 2005a, 2005b, 2005c; Yun et al., 2005). Analysis of metabolism in silico has been used to design gene knockouts to create a pathway in *E. coli* that is analogous to the native succinate pathway in *Mannheimia succiniciproducens* (Lee et al., 2005 and 2006). The resulting strain, however, produced very little succinate. Andersson et al. (2007) reported the highest levels of succinate production by an engineered *E. coli* (339 mM) containing only native genes.

Other researchers have pursued alternative approaches that express heterologous genes in *E. coli*. The *Rhizobium eteloti* pyruvate carboxylase (pyc) was over-expressed from a multicopy plasmid to direct carbon flow to succinate. (Gokarn et al., 2000; Vemuri et al., 2002a, 2002b). Strain SBS550MG was constructed by inactivating the isocitrate lyase repressor (iclR), adhE, ldhA, and ackA, and over-expressing the *Bacillus subtilis* citZ (citrate synthase) and *R. etli* pyc from a multi-copy plasmid (Sanchez et al., 2005a). With this strain, 160 mM succinate was produced from glucose with a molar yield of 1.6.

More complex processes have also been investigated for succinate production (Table 1). Many of these processes include an aerobic growth phase followed by an anaerobic production phase. The anaerobic phase is often supplied with carbon dioxide, hydrogen, or both (Andersson et al., 2007; Sanchez et al., 2005a and 2005b; Sanchez et al., 2006; U.S. Pat. No. 5,869,301; Vemuri et al., 2002a and 2002b). In a recent study with a native succinate producer, *A. succiniciproducens*, electrodialysis, sparging with $CO_2$, cell recycle, and batch feeding were combined (Meynial-Salles et al., 2007).

The subject invention provides various forms of microorganisms, such as strains of *E. coli*, that produce succinate at high titers and yields in mineral salts media during simple, pH-controlled, batch fermentations without the need for heterologous genes or plasmids. During development, an intermediate strain was characterized that produced malate as the dominant product.

BRIEF SUMMARY OF THE INVENTION

The subject invention provides novel microorganisms useful in the production of lactic acid, for example, *Escherichia coli*. Accordingly, the materials and methods of the subject invention can be used to produce succinate and malate for use in a variety of applications.

In certain embodiments, derivatives of *Escherichia coli* (also referred to herein as *E. coli*) can be used for the construction of strains producing succinate, malate and alanine. In various embodiments, *E. coli* C (e.g. ATCC 8739) can be used as can any other strain of *E. coli* that can be obtained from various depositories or commercial sources. The engineered microbes of the invention, in some embodiments, also contain only native genes (i.e., contain no genetic material from other organisms). Additional advantages of this invention will become readily apparent from the ensuing description.

BRIEF DESCRIPTION OF THE FIGURES

FIG. 1A shows the standard pathway for fermentation of glucose by *E. coli*. This pathway has been redrawn from Unden and Kleefeld (2004). Bold arrows represent central fermentative pathways. Crosses represent the gene deletions performed in this study to engineer KJ012 (ldhA, adhE, ackA). Genes and enzymes: ldhA, lactate dehydrogenase; pflB, pyruvate-formate lyase; focA, formate transporter; pta, phosphate acetyltransferase; ackA, acetate kinase; adhE, alcohol dehydrogenase; ppc, phosphoenolpyruvate carboxylase; pdh, pyruvate dehydrogenase complex; gltA, citrate synthase; mdh, malate dehydrogenase; fumA, fumB, and fumC, fumarase isozymes; frdABCD, fumarate reductase; fdh, formate dehydrogenase; icd, isocitrate dehydrogenase; acs, acetyl-CoA synthetase; mgsA, methylglyoxal synthase; poxB, pyruvate oxidase; aldA, aldehyde dehydrogenase; and aldB, aldehyde dehydrogenase. FIG. 1B shows the coupling of ATP production and growth to succinate and malate production in engineered strains of *E. coli*. Solid arrows connect NADH pools. Dotted arrows connect NAD$^+$ pools. During glycolysis under anaerobic conditions, growth is obligately coupled to the production of ATP and the oxidation of NADH.

FIGS. 2A-2D. Potential carboxylation pathways for succinate production by *E. coli*. Genes encoding key carboxylating enzymes are shown in bold. FIG. 2A shows the PEP carboxylase. No ATP is produced from phosphoenolpyruvate (PEP). This is regarded as the primary route for succinate production by *E. coli* during glucose fermentation.

FIG. 2B shows the malic enzyme (NADH). Energy is conserved during the production of ATP from ADP and PEP by pyruvate kinase (pykA or pykF). Malic enzyme (sfcA) catalyzes an NADH-linked, reductive carboxylation to produce malate. FIG. 2C shows the malic enzyme (NADPH). Energy is conserved during the production of ATP from ADP and PEP by pyruvate kinase (pykA or pykF). Malic enzyme (maeB) catalyzes an NADPH-linked, reductive carboxylation to produce malate. FIG. 2D shows the PEP carboxykinase. Energy is conserved by the production of ATP during the carboxylation of PEP to produce oxaloacetic acid.

FIGS. 3A-3C. Growth during metabolic evolution of KJ012 to produce KJ017, KJ032, and KJ060. Strain KJ012 was sequentially transferred in NBS medium containing 5% (w/v) (FIG. 3A) and 10% (w/v) (FIG. 3B) glucose, respectively to produce KJ017. After deletion of focA and pflB, the resulting strain (KJ032) was initially subcultured in medium supplemented with acetate (FIG. 3C). Acetate levels were decreased and subsequently eliminated during further transfers to produce KJ060. Broken line represents fermentation by KJ017 without acetate, added for comparison. Symbols: optical density at $OD_{550nm}$, ●.

FIG. 4A (5% w/v glucose) and FIG. 4B (10% w/v glucose), KJ012 to KJ017; FIG. 4C (5% w/v glucose) and FIG. 4D (10% w/v glucose), KJ032 to KJ060; FIG. 4E. 10% glucose, KJ070 to KJ071; FIG. 4F. 10% glucose, KJ072 to KJ073. Symbols for all: ■, succinate; □, formate; Δ, acetate; ▲, malate; ♦, lactate; and ▼, pyruvate.

FIG. 7A shows succinate production by KJ060 in AM1 medium. FIG. 7B shows succinate production by KJ073 in AM1 medium. FIG. 7C shows production of malate by KJ071 in NBS medium. Fermentations were inoculated at a level of 33 mg DCW $l^{-1}$. Symbols for all: ○, glucose; ●, succinate; ■, malate; Δ, cell mass.

DETAILED DESCRIPTION OF THE INVENTION

Figure 1A:
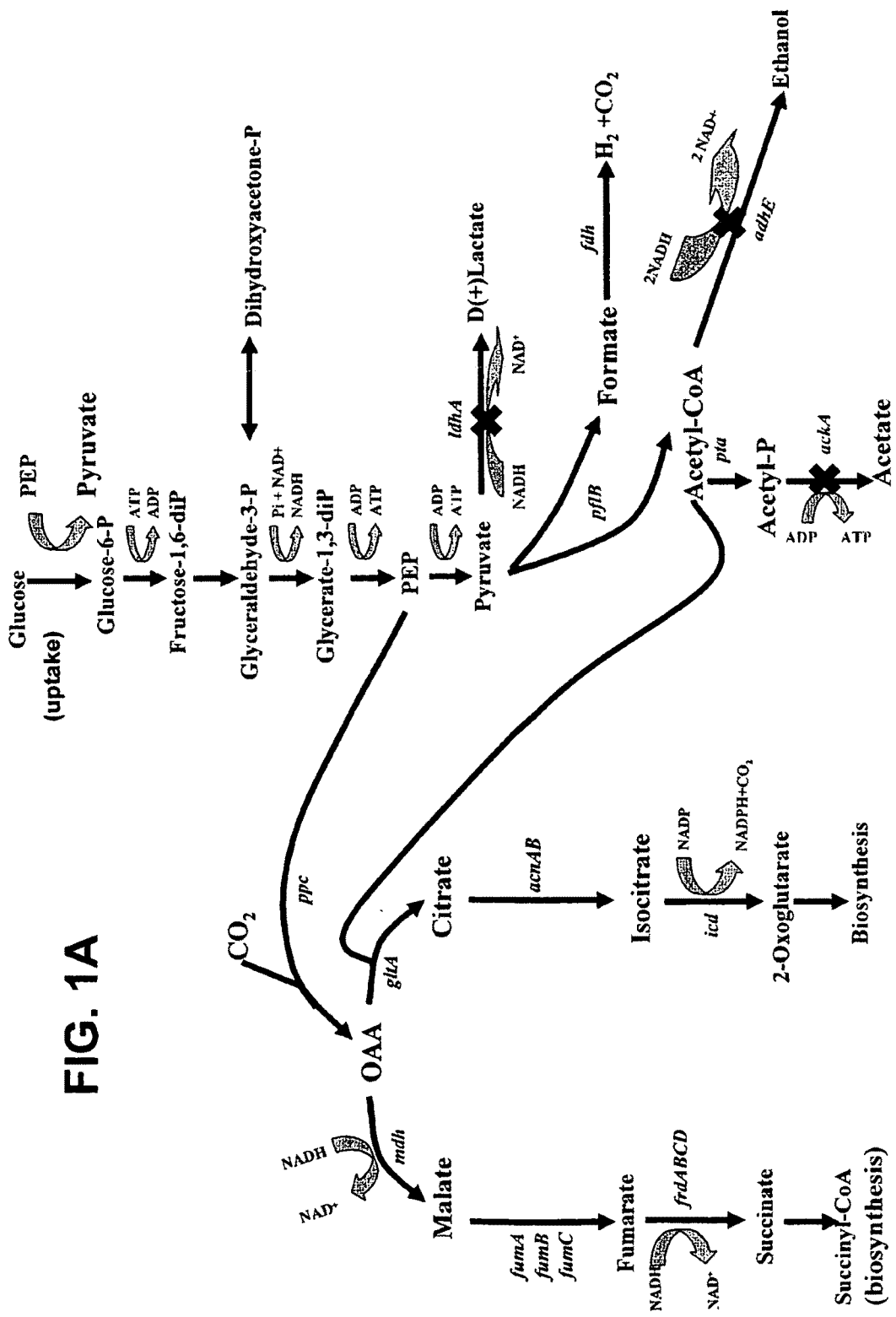
FIGS. 1A-1B. Fermentation of glucose to succinate.

The subject invention provides materials and methods wherein unique and advantageous combinations of gene mutations are used to direct carbon flow to a desired product, such as succinate and/or malate. The techniques of the subject invention can be used to obtain products from native pathways as well as from recombinant pathways. Advantageously, the subject invention provides a versatile platform for the production of these products with only mineral salts and sugar as nutrients.

A microorganism of the present invention can be obtained by modification of one or more target genes in a bacterium, such as those belonging to *Escherichia*. In some embodiments, the bacterium that is modified may be *Escherichia coli*, or a particular strain thereof, such as *E. coli* B, *E. coli* C, *E. coli* W, or the like. In some other embodiments of the invention, bacteria that can be modified according to the present invention include, but are not limited to, *Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicis, Brevibacterium ammoniagenes, divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium auraminum, Flavobacterium rhenanum, Flavobacterium sewanense, Flavobacterium breve, Flavobacterium meningosepticum, Micrococcus sp. CCM825, Morganella morganii, Nocardia opaca, Nocardia rugosa, Planococcus eucinatus, Proteus rettgeri, Propionibacterium shermanii, Pseudomonas synxantha, Pseudomonas azotoformans, Pseudomonas fluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus* sp. ATCC 15592, *Rhodococcus* sp. ATCC 19070, *Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Escherichia freundii, Microbacterium ammoniaphilum, Serratia marcescens, Salmonella typhimurium, Salmonella schottmulleri, Xanthomonas citri* and so forth.

In certain embodiments, the subject invention provides bacterial strains (such as *E. coli*) lacking plasmids, antibiotic resistance genes and/or material from other organisms that are suitable for the production of succinate or malate. Unlike other microbial systems, the microorganisms of the subject invention can be employed in a single step production process using sugars as substrates, have high rates of product production, high yields, simple nutritional requirements (e.g., mineral salts medium), and a robust metabolism permitting the bioconversion of hexoses, pentoses and many disaccharides.

Thus, microorganisms produced according to the instant disclosure can have one or more target genes inactivated by various methods known in the art. For example, target genes can be inactivated by the introduction of insertions, deletions, or random mutations into the target gene. Thus, certain aspects of the invention provide for the insertion of at least one stop codon (e.g., one to ten or more stop codons) into the target gene. Some aspects of the invention provide for the insertion or deletion of 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 or more bases in order to introduce a frameshift mutation in a target gene. Other aspects of the invention provide for the insertion or deletion of 1, 2, 4, 5, 7, 8, 10, 11, 13, 14, 16, 17, 19, 20, 22, 23, 25, 26, 28, 29 or more bases in order to introduce a frameshift mutation in a target gene. Yet other embodiments of the subject application provide for the introduction of one or more point mutations (e.g., 1 to 30 or more) within a target gene while other aspects of the invention provide for the partial, total or complete deletion of a target gene from the microorganisms of the invention. In each of these aspects of the invention, metabolic pathways are inactivated by the inactivation of the enzymatic activity of the polypeptide encoded by the target gene(s).

"Target gene(s)" as used herein, refer to gene coding acetate kinase, alcohol dehydrogenase, aspartate aminotransferase, citrate lyase, formate transporter, lactate dehydrogenase, methylglyoxal synthase, pyruvate-formate lyase, pyruvate oxidase, phosphate acetyltransferase, malic enzyme, and/or propionate kinase/α-ketobutyrate formatelyase. In certain preferred embodiments, the genes are ackA (acetate kinase), adhE (alcohol dehydrogenase), aspC (aspartate aminotransferase), citCDEF (citrate lyase), focA (formate transporter), ldhA (lactate dehydrogenase), mgsA (methylglyoxal synthase), pflB (pyruvate-formate lyase), poxB (pyruvate oxidase), pta (phosphate acetyltransferase), sfcA (malic enzyme) and/or tdcDE (propionate kinase/α-ketobutyrate formatelyase). Thus, in certain aspects of the invention, one or more of these genes are inactivated in a microorganism (any bacterial strain containing such genes, e.g., *E. coli*). The selection process for strains with improved growth and succinate or malate production is referred to as "metabolic evolution" (examples of which are provided within the disclosed examples). A "native *E. coli* gene" or "native *E. coli* genes" is/are to be understood to be a gene (or genes) that is/are naturally found in an *E. coli* microorganism as opposed to a "heterologous gene" that is introduced into an *E. coli* and which was obtained from any microorganism other than *E. coli*.

Various non-limiting embodiments of the subject invention include:

1. A genetically modified bacterial strain that comprises genetic modifications to one or more of the following target genes: a) acetate kinase, b) lactate dehydrogenase, c) alcohol dehydrogenase, d) pyruvate formatelyase, e) methylglyoxal synthase, f) pyruvate oxidase, and/or g) citrate lyase, said genetic modifications inactivating the enzymatic activity of the polypeptide produced by said target gene;

2. The genetically modified bacterial strain according to embodiment 1, wherein said genetically modified bacterial strain is *Escherichia coli, Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicis, Brevibacterium ammoniagenes, divaricatum, Brevibacterium lactofermentum, Brevibacterium flavum, Brevibacterium globosum, Brevibacterium fuscum, Brevibacterium ketoglutamicum, Brevibacterium helcolum, Brevibacterium*

*pusillum, Brevibacterium testaceum, Brevibacterium roseum, Brevibacterium immariophilium, Brevibacterium linens, Brevibacterium protopharmiae, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Micrococcus sp. CCM825, Morganella morganii, Nocardia opaca, Nocardia rugosa, Planococcus eucinatus, Proteus rettgeri, Propionibacterium shermanii, Pseudomonas synxantha, Pseudomonas azotoformans, Pseudomonas fluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus sp. ATCC 15592, Rhodococcus sp. ATCC 19070, Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Escherichia freundii, Microbacterium ammoniaphilum, Serratia marcescens, Salmonella typhimurium, Salmonella schottmulleri,* or *Xanthomonas citri;*

3. The genetically modified bacterial strain according to embodiment 1 or 2, wherein said modified bacterial strain is *E. coli* B;

4. The genetically modified bacterial strain of embodiments 1, 2 or 3, wherein the following target genes are inactivated: a) acetate kinase, b) lactate dehydrogenase, c) alcohol dehydrogenase, d) pyruvate formatelyase, and e) pyruvate oxidase;

5. The genetically modified bacterial strain of embodiment 4, wherein said bacterial strain further comprises an inactivated methylglyoxal synthase gene;

6. The genetically modified bacterial strain of embodiments 4 or 5, wherein said bacterial strain further comprises an inactivated citrate lyase gene;

7. The genetically modified bacterial strain according to embodiments 1, 2, 3, 4 or 5, wherein said genetically modified bacterial strain is metabolically evolved;

8. The genetically modified bacterial strain according to embodiments 1, 2, 3, 4, 5, 6, or 7, wherein the genes, or portions thereof, are deleted;

9. The genetically modified bacterial strain according to embodiments 1, 2, 3, 4, 5, 6, or 7, wherein the genes are inactivated with frameshift mutations, point mutations, the insertion of stop codons or combinations thereof;

10. The genetically modified bacterial strain according to embodiments 2, 3, 4, 5, 6, 7, 8, or 9, wherein said genetically modified bacterial strain is an *E. coli* strain and does not contain an exogenous gene or fragment thereof (or only contains native *E. coli* genes);

11. The genetically modified bacterial strain according to embodiments 1, 2, 3, 4, 5, 6, 7, 8, 9, or 10, with the proviso that: 1) said genetically modified bacterial strain has not had one or more of the following genes inactivated: a) fumarate reductase; b) ATP synthase; c) 2-ketoglutarate dehydrogenase (sucAB); d) succinate dehydrogenase (e.g., sdhAB), phosphate acetyltransferase (e.g., pta); e) glucose transporter (e.g., ptsG); f) isocitrate lyase repressor (e.g., iclR); and/or 2) that said genetically modified strain does not contain a plasmid or multicopy plasmid encoding and/or over-expressing genes such as malate dehydrogenase (mdh) and phosphoenolpyruvate carboxylase (ppc), pyruvate carboxylase (pyc) and/or citrate synthase (e.g., *Bacillus subtilis* citZ);

12. The genetically modified bacterial strain according to embodiments 1-11, wherein said genetically modified bacterial strain is KJ012, KJ017, KJ032, KJ044, KJ059, KJ060, KJ070, KJ071, KJ072 or KJ073;

13. A method of culturing or growing a genetically modified bacterial strain comprising inoculating a culture medium with one or more genetically modified bacterial strain according to any one of embodiments 1, 2, 3, 4, 5, 6, 7, 8, 9, 10, 11 or 12 and culturing or growing said a genetically modified bacterial strain;

14. A method of producing succinate or malate comprising culturing one or more genetically modified bacterial strain according to any one of embodiments 1, 2, 3, 4, 5, 6, 7, 8, 9, 10, 11 or 12 under conditions that allow for the production of succinate or malate;

15. The method according to embodiment 14, wherein said one or more genetically modified bacterial strain is KJ012, KJ034, KJ044, KJ059, KJ060, KJ070, KJ071, KJ072 or KJ073;

16. The method according to any one of embodiments 13, 14 or 15 wherein said genetically modified bacterial strain is cultured in a mineral salts medium;

17. The method according to embodiment 16, wherein the mineral salts medium comprises between 2% and 20% (w/v) carbohydrate;

18. The method according to embodiment 17, wherein the mineral salts medium contains 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5% or 20% (w/v) of a sugar;

19. The method according to claim 17 or 18, wherein the carbohydrate is glucose, fructose, xylose, arabinose, galactose, mannose, rhamnose, sucrose, cellobiose, hemicellulose or various combinations thereof;

20. The method according to embodiments 14, 15, 16, 17, 18 or 19 wherein succinate or malate is produced at concentrations of at least 0.20M, 0.25M, 0.30M, 0.35M, 0.40M, 0.45M, 0.50M, 0.55M, 0.60M, 0.65M, or 0.70M;

21. The method according to embodiments 14, 15, 16, 17, 18, 19 or 20 wherein the culture medium is NBS mineral salts medium or AM1 medium (see Table 4);

22. The method according to embodiments 14, 15, 16, 17, 18, 19, 20 or 21 wherein the yield of succinate or malate is at least or greater than (or greater than or equal to) 90%;

23. The method according to embodiment 22, wherein the yield is at least 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, or 99%;

24. The method according to any one of claims 13-16 or 20-23, wherein the growth medium comprises glycerol as a substrate for the production of succinate, malate or fumarate.

25. The method according to claim 17-19, wherein said medium further comprises glycerol as a substrate for the production of succinate, malate or fumarate; or 26. A composition comprising one or more genetically modified bacterial strain according to any one of embodiments 1, 2, 3, 4, 5, 6, 7, 8, 9, 10, 11 or 12 and medium.

The following additional embodiments are also provided by the subject application:

1. A genetically modified bacterial strain that comprises genetic modifications to the following target genes encoding: a) acetate kinase, b) lactate dehydrogenase, c) alcohol dehydrogenase, d) pyruvate formatelyase, e) methylglyoxal synthase, f) pyruvate oxidase, g) citrate lyase, h) aspartate aminotransferase, i) formate transporter, j) phosphate acetyltransferase, k) malic enzyme, and l) propionate kinase/α-ketobutyrate formatelyase, said genetic modifications inactivating the enzymatic activity of the polypeptide produced by said target gene;

2. The genetically modified bacterial strain according to embodiment 1, wherein said genetically modified bacterial strain is *Escherichia coli, Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Brevibacterium ammoniagenes, divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Micrococcus* sp. CCM825, *Morganella morganii, Nocardia opaca, Nocardia rugosa, Planococcus eucinatus, Proteus rettgeri, Propionibacterium shermanii, Pseudomonas synxantha, Pseudomonas azotoformans, Pseudomonas fluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus* sp. ATCC 15592, *Rhodococcus* sp. ATCC 19070, *Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Escherichia freundii, Microbacterium ammoniaphilum, Serratia marcescens, Salmonella typhimurium, Salmonella schottmulleri,* or *Xanthomonas citri*;

3. The genetically modified bacterial strain according to embodiment 2, wherein said genetically modified bacterial strain is *Escherichia coli*;

4. A genetically modified bacterial strain that comprises:
(a) genetic modification to a citrate lyase gene and one or more of the following target genes encoding: a) acetate kinase, b) lactate dehydrogenase, c) alcohol dehydrogenase, d) pyruvate formatelyase, e) methylglyoxal synthase, f) pyruvate oxidase, g) aspartate aminotransferase, h) formate transporter, i) phosphate acetyltransferase, j) malic enzyme, and/or k) propionate kinase/α-ketobutyrate formatelyase; or
(b) genetic modification to a citrate lyase gene, lactate dehydrogenase gene, alcohol dehydrogenase gene, acetate kinase gene, formate transporter gene, pyruvate formatelyase gene, methylglyoxal synthase gene, pyruvate oxidase gene, and one or more of the following target genes: a) aspartate aminotransferase, b) phosphate acetyltransferase, c) malic enzyme, and/or d) propionate kinase/α-ketobutyrate formatelyase;
said genetic modification inactivating the enzymatic activity of the polypeptide produced by said target gene;

5. The genetically modified bacterial strain according to embodiment 4, wherein said genetically modified bacterial strain is *Escherichia coli, Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Brevibacterium ammoniagenes, divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Micrococcus* sp. CCM825, *Morganella morganii, Nocardia opaca, Nocardia rugosa, Planococcus eucinatus, Proteus rettgeri, Propionibacterium shermanii, Pseudomonas synxantha, Pseudomonas azotoformans, Pseudomonas fluorescens, Pseudomonas ovalis, Pseudomonas stutzeri, Pseudomonas acidovolans, Pseudomonas mucidolens, Pseudomonas testosterone, Pseudomonas aeruginosa, Rhodococcus erythropolis, Rhodococcus rhodochrous, Rhodococcus* sp. ATCC 15592, *Rhodococcus* sp. ATCC 19070, *Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Escherichia freundii, Microbacterium ammoniaphilum, Serratia marcescens, Salmonella typhimurium, Salmonella schottmulleri,* or *Xanthomonas citri*;

6. The genetically modified bacterial strain according to embodiment 5, wherein said genetically modified bacterial strain is *Escherichia coli*;

7. The genetically modified bacterial strain according to embodiment 1, 2, 3, 4, 5 or 6, wherein said genetically modified bacterial strain is metabolically evolved;

8. The genetically modified bacterial strain according to embodiment 1, 2, 3, 4, 5 or 6, wherein the target gene, or portions thereof, or target genes, or portions thereof, are inactivated by deletion, frameshift mutations, point mutations, the insertion of stop codons or combinations thereof;

9. The genetically modified bacterial strain according to embodiment 1, 2, 3, 4, 5 or 6, wherein said genetically modified bacterial strain does not contain an exogenous gene or fragment thereof or only contains native genes;

10. The genetically modified bacterial strain according to embodiment 1, 2, 3, 4, 5 or 6, with the proviso that: 1) said genetically modified bacterial strain has not had one or more of the following enzymes inactivated: a) fumarate reductase;

b) ATP synthase; c) 2-ketoglutarate dehydrogenase; d) succinate dehydrogenase; e) glucose transporter; f) isocitrate lyase repressor; and/or 2) that said genetically modified strain does not contain a plasmid or multicopy plasmid encoding and/or over-expressing malate dehydrogenase, phosphoenolpyruvate carboxylase, pyruvate carboxylase and/or citrate synthase;

11. The genetically modified bacterial strain according to embodiment 7, 8, 9, 10 or 11, wherein said genetically modified bacterial strain is metabolically evolved;

12. The genetically modified bacterial strain according to any one of embodiments 1-10, wherein said genetically modified bacterial strain produces:
   a) succinate concentrations of at least 200 mM, 250 mM, 300 mM, 350 mM, 400 mM, 450 mM, 500 mM, 550 mM, 600 mM, 650 mM, or 700 mM;
   b) fumarate concentrations of at least 200 mM, 250 mM, 300 mM, 350 mM, 400 mM, 450 mM, 500 mM, 550 mM, 600 mM, 650 mM, or 700 mM; or
   c) malate concentrations of at least 200 mM, 250 mM, 300 mM, 350 mM, 400 mM, 450 mM or 500 mM;

13. A genetically modified bacterial strain, wherein said genetically modified bacterial strain is KJ012, KJ017, KJ032, KJ044, KJ059, KJ060, KJ070, KJ071, KJ072, KJ073, KJ076, KJ079, KJ091, KJ098, KJ104, KJ110, KJ119, KJ122, or KJ134;

14. A method of culturing or growing a genetically modified bacterial strain comprising inoculating a culture medium with one or more genetically modified bacterial strain according to any one of embodiments 1-13 and culturing or growing said a genetically modified bacterial strain;

15. A method of producing succinate, fumarate or malate comprising culturing one or more genetically modified bacterial strain one according to any one of embodiments 1-13 under conditions that allow for the production of succinate or malate or fumarate;

16. The method according to embodiment 15, wherein said one or more genetically modified bacterial strain is KJ012, KJ017, KJ032, KJ044, KJ059, KJ060, KJ070, KJ071, KJ072, KJ073, KJ076, KJ079, KJ091, KJ098, KJ104, KJ110, KJ119, KJ122, or KJ134;

17. The method according to any one of embodiments 14-16, wherein said genetically modified bacterial strain is cultured in a mineral salts medium;

18. The method according to embodiment 17, wherein the mineral salts medium comprises between 2% and 20% (w/v) carbohydrate;

19. The method according to embodiment 18, wherein the mineral salts medium contains 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5% or 20% (w/v) of a sugar;

20. The method according to embodiment 18 or 19, wherein the carbohydrate is glucose, fructose, xylose, arabinose, galactose, mannose, rhamnose, sucrose, cellobiose, hemicellulose or combinations thereof;

21. The method according to any one of embodiments 15-20, wherein the yield of succinate or malate is greater than or equal to 90%;

22. The method according to embodiment 21, wherein the yield is at least 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, or 99%;

23. The method according to any one of embodiments 15-22, wherein said genetically modified bacterial strain produces succinate concentrations of at least 200 mM, 250 mM, 300 mM, 350 mM, 400 mM, 450 mM, 500 mM, 550 mM, 600 mM, 650 mM, or 700 mM;

24. The method according to any one of embodiments 15-22, wherein said genetically modified bacterial strain produces malate concentrations of at least 200 mM, 250 mM, 300 mM, 350 mM, 400 mM, 450 mM or 500 mM;

25. The method according to any one of embodiments 15-22, wherein said genetically modified bacterial strain produces fumarate concentrations of at least 200 mM, 250 mM, 300 mM, 350 mM, 400 mM, 450 mM, 500 mM, 550 mM, 600 mM, 650 mM, or 700 mM;

26. The method according to any one of embodiments 14-17 or 21-25, wherein the growth medium comprises glycerol as a substrate for the production of succinate, malate or fumarate;

27. The method according to any one of embodiments 18-20, wherein said medium further comprises glycerol as a substrate for the production of succinate, malate or fumarate; or 28. A composition comprising one or more genetically modified bacterial strain according to embodiments 1-13 and medium.

Microorganisms were deposited as indicated in the Examples with the Agricultural Research Service Culture Collection, 1815 N. University Street, Peoria, Ill., 61604 U.S.A. These cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of the deposits docs not constitute a license to practice the subject invention in derogation of patent rights granted by governmental action.

Further, the subject culture deposits will be stored and made available to the public in accord with the provisions of the Budapest. Treaty for the Deposit of Microorganisms, i.e., they will be stored with all the care necessary to keep them viable and uncontaminated for a period of at least five years after the most recent request for the furnishing of a sample of the deposits, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

Following are examples that illustrate procedures for practicing the invention. These examples should not be construed as limiting. All percentages are by weight and all solvent mixture proportions are by volume unless otherwise noted.

EXAMPLE 1

Microorganisms were deposited with the ARS Culture Collection as follows:

| Culture | Strain Designations | Deposit Date |
|---------|--------------------|--------------| 
| KJ012   | B-50022            | Mar. 15, 2007 |
| KJ017   | B-50023            | Mar. 15, 2007 |
| KJ032   | B-50024            | Mar. 15, 2007 |
| KJ060   | B-50025            | Mar. 15, 2007 |
| KJ070   | B-50026            | Mar. 15, 2007 |
| KJ071   | B-50027            | Mar. 15, 2007 |
| KJ072   | B-50028            | Mar. 15, 2007 |
| KJ073   | B-50029            | Mar. 15, 2007 |

Materials and Methods
Strains, Media and Growth Conditions

Strains used in this study are summarized in Table 2. Derivatives of *E. coli* C (ATCC 8739) were developed for succinate production by a unique combination of gene deletions and selections for increased productivity. Cultures were grown at 37° C. in modified Luria-Bertani (LB) broth (per liter: 10 g Difco tryptone, 5 g Difco yeast extract, 5 g sodium chloride) (Miller, 1992) only during strain construction. Antibiotics were included as appropriate.

NBS mineral salts medium (Causey et al., 2004) supplemented with 100 mM KHCO$_3$, 1 mM betaine HCl, and sugar (2% to 10%) was used as a fermentation broth in most studies and for maintenance of strains. A new low salt medium, AM1 (4.2 g l$^{-1}$ total salts; Martinez et al., 2007), was developed during the latter stages of this investigation and used in fermentations with KJ060 and KJ073. This medium was supplemented with 100 mM KHCO$_3$ and sugar as indicated and includes 1 mM betaine when initial sugar concentrations are 5% or higher. No genes encoding antibiotic resistance, plasmids, or other foreign genes are present in strains developed for succinate production except as intermediates during construction.

Genetic Methods

Plasmids and primers used in this study are summarized in Table 2. Methods for chromosomal deletions, integration, and removal of antibiotic resistance genes have been previously described (Datsenko and Wanner, 2000; Grabar et al. 2006; Posfai et al., 1997; Zhou et al. 2006). Sense primers contain sequences corresponding to the N-terminus of each targeted gene (boldface type) followed by 20 by (underlined) corresponding to the FRT-kan-FRT cassette. Anti-sense primers contain sequences corresponding to the C-terminal region of each targeted gene (boldface type) followed by 20 by (underlined) corresponding to the cassette. Amplified DNA fragments were electroporated into *E. coli* strains harboring Red recombinase (pKD46). In resulting recombinants, the FRT-kan-FRT cassette replaced the deleted region of the target gene by homologous recombination (double-crossover event). The resistance gene (FRT-kan-FRT) was subsequently excised from the chromosome with FLP recombinase using plasmid pFT-A, leaving a scar region containing one FRT site. Chromosomal deletions and integrations were verified by testing for antibiotic markers, PCR analysis, and analysis of fermentation products. Generalized P1 phage transduction (Miller, 1992) was used to transfer the ΔfocA-pflB::FRT-kan-FRT mutation from strain SZ204 into strain KJ017 to produce KJ032.

Deletion of mgsA and poxB Genes

A modified method was developed to delete *E. coli* chromosomal genes using a two-step homologous recombination process (Thomason et al., 2005). With this method, no antibiotic genes or scar sequences remain on the chromosome after gene deletion. In the first recombination, part of the target gene was replaced by a DNA cassette containing a chloramphenicol resistance gene (cat) and a levansucrase gene (sacB). In the second recombination, the cat-sacB cassette was replaced with native sequences omitting the region of deletion. Cells containing the sacB gene accumulate levan during incubation with sucrose and are killed. Surviving recombinants are highly enriched for loss of the cat-sac) cassette.

A cassette was constructed to facilitate gene deletions. The cat-sacB region was amplified from pEL04 (Lee et al., 2001; Thomason et al., 2005) by PCR using the JMcatsacB primer set (Table 2), digested with NheI, and ligated into the corresponding site of pLOI3421 to produce pLOI4151. The cat-sacB cassette was amplified by PCR using pLOI4151 (template) and the cat-up2/sacB-down2 primer set (EcoRV site included in each primer), digested with EcoRV, and used in subsequent ligations.

The mgsA gene and neighboring 500 by regions (yccT'-mgsA-helD', 1435 bp) were amplified using primer set mgsA-up/down and cloned into the pCR2.1-TOPO vector (Invitrogen) to produce plasmid pLOI4228. A 1000-fold diluted preparation of this plasmid DNA served as a template for inside-out amplification using the mgsA-112 primer set (both primers within the mgsA gene and facing outward). The resulting 4958 by fragment containing the replicon was ligated to the amplified, EcoRV-digested cat-sacB cassette from pLOI4151 to produce pLOI4229. This 4958 by fragment was also used to construct a second plasmid, pLOI4230 (phosphorylation and self-ligation). In pLOI4230, the central region of mgsA is absent (yccT'-mgsA'-mgsA"-helD').

After digestion of pLOI4229 and pLOI4230 with XmnI (within the vector), each served as a template for amplification using the mgsA-up/down primer set to produce the linear DNA fragments for integration step I (yccT'-mgsA'-cat-sacB-mgsA"-helD') and step II (yccT'-mgsA'-mgsA"-helD'), respectively. After electroporation of the step I fragment into KJ060 containing pKD46 (Red recombinase) and 2 h of incubation at 30° C. to allow expression and segregation, recombinants were selected for chloramphenicol (40 mg l$^{-1}$) and ampicillin (20 mg l$^{-1}$) resistance on plates (30° C., 18 h). Three clones were chosen, grown in Luria broth with ampicillin and 5% w/v arabinose, and prepared for electroporation. After electroporation with the step II fragment, cells were incubated at 37° C. for 4 h and transferred into a 250-ml flask containing 100 ml of modified LB (100 mM MOPS buffer added and NaCl omitted) containing 10% sucrose. After overnight incubation (37° C.), clones were selected on modified LB plates (no NaCl; 100 mM MOPS added) containing 6% sucrose (39° C., 16 h). Resulting clones' were tested for loss of ampicillin and chloramphenicol resistance. Construction was further confirmed by PCR analysis. A clone lacking the mgsA gene was selected and designated KJ070.

The poxB gene was deleted from KJ071 in a manner analogous to that used to delete the mgsA gene. Additional primer sets (poxB-up/down and poxB-1/2) used to construct the poxB deletion are included in Table 2 together with the corresponding plasmids (pLOI4274, pLOI4275, and pLOI4276). The resulting strain was designated KJ072.

Enzyme Assays

Cells were grown in NBS medium with 5% or 10% glucose, and harvested during mid-log growth by centrifugation (8,000 g for 5 min at 4° C.), washed with cold 100 mM Tris-HCl (pH 7.0) buffer, and resuspended in the same buffer (5 ml). Cells were disrupted by Bead-treatment (MP Biomedicals; Solon, Ohio) with glass beads and then centrifuged at 13,000 g for 15 min to get the crude extract. Proteins were measured by the BCA method, with bovine scrum albumin as the standard (Pierce BCA Protein Assay Kit).

PEP carboxylase activity was measured as described before (Canovas and Kornberg, 1969). The reaction mixture contains 100 mM Tris-HCl buffer (pH8.0), 10 mM MgCl$_2$, 1 mM DTT, 25 mM NaHCO$_3$, 0.2 mM NADH, 20 U malate dehydrogenase, and 10 mM PEP reaction was started by addition of crude extract. PEP carboxykinase activity was measured as described before (Van der Werf, et al., 1997). The reaction mixture contains 100 mM MES buffer (pH6.6), 10 mM MgCl$_2$, 75 mM NaHCO$_3$, 5 mM MnCl$_2$, 50 mM ADP, 1 mM DTT, 0.2 mM NADH, 20 U malate dehydrogenase, and 10 mM PEP. The reaction was started by addition of crude extract.

NAD$^+$ dependent malic enzyme activity was measured at both directions as described before (Stols and Donnelly, 1997). For carboxylation direction, the reaction mixture contains 100 mM Tris-HCl buffer (pH7.5), 25 mM NaHCO$_3$, 1 mM MnCl$_2$, 1 mM DTT, 0.2 mM NADH, and 25 mM pyruvate. The reaction was started by addition of crude extract. However, this assay method cannot measure malic enzyme activity in wild type E. coli C due to the presence of lactate dehydrogenase. For decarboxylation, the reaction mixture contains 100 mM Tris-HCl buffer (pH7.5), 2.5 mM NAD$^+$, 1 mM DTT, 10 mM MgCl$_2$, 20 mM KCl and 20 mM L-malate. The reaction was started by addition crude extract.

NADP$^+$ dependent malic enzyme activity was measured in the same way for NADP$^+$ dependent malic enzyme, except NAD(H)$^+$ was replaced by NADP(H)$^+$. One unit of activity was defined as the amount of enzyme to oxidize or reduce 1 nmol of substrate per min.

Real Time RT-PCR Analysis

Real time RT-PCR was used to measure message RNA levels as described previously (Jarboe et al., 2008). Cells were grown in NBS medium with 5% or 10% glucose and harvested during mid-log growth by swirling in a dry ice/ethanol bath, following by centrifugation and storage at −80° C. in RNALater (Qiagen, Valencia Calif.) until purification. RNA purification was performed with RNeasy Mini columns (Qiagen), followed by digestion with DNaseI (Invitrogen). Reverse transcription with Superscript II (Invitrogen, Carlsbad Calif.) used 50 ng total RNA as template. Real-time PCR was performed in a Bio-Rad iCycler with SYBR Green RT-PCR mix (Bio-Rad, Hercules Calif.). RNA was checked for genomic DNA contamination by running a RT-PCR in the absence of reverse transcription. Transcript abundance was estimated using genomic DNA as a standard and expression levels were normalized by the birA gene, a transcriptional repressor (Jarboe et al., 2008). RT-PCR primers used for pck and birA are listed in Table 2.

Sequencing of pck Region

In order to know whether there was any mutation occurred in the pck gene of KJ073, the coding region and promotor region (about 800 by in front of coding region) of pck gene in both KJ012 and KJ073 were amplified by PfuUltra High Fidelity DNA Polymerase (Stratagene; Wilmington, Del.). Primer set pck-F/R was used to amplify the coding region through the transcriptional terminator. Primer set pck-2 was used to amplify the promoter region. DNA sequencing was provided by the University of Florida Interdisciplinary Center for Biotechnology Research (with Applied Biosystems autosequencers).

Fermentations

Seed cultures and fermentations were grown at 37° C., 100 rpm in NBS or AM1 mineral salts medium containing glucose, 100 mM KHCO$_3$ and 1 mM betaine HCl. These were maintained at pH 7.0 by the automatic addition of KOH during initial experiments. Subsequently, pH was maintained by adding a 1:1 mixture of 3M K$_2$CO$_3$ and 6N KOH. Fermentations were carried out in small fermentation vessels with a working volume of 350 ml. Fermentations were inoculated at either an initial OD$_{550}$ of 0.01 (3.3 mg CDW l$^{-1}$) or 0.1 (33.3 mg CDW l$^{-1}$) as indicated. No antibiotic resistance genes were present in the strains that were tested. Fermentation vessels were sealed except for a 16 gauge needle which served as a vent for sample removal. Anaerobiosis was rapidly achieved during growth with added bicarbonate serving to ensure an atmosphere of CO$_2$.

Analyses

Cell mass was estimated from the optical density at 550 nm (OD 1.0=333 mg of cell dry weight l$^{-1}$) with a Bausch & Lomb Spectronic 70 spectrophotometer. Organic acids and sugars were determined by using high performance liquid chromatography (Grabar et al., 2006).

Results and Discussion

Construction of KJ012 for Succinate Production: Deletion of ldhA, adhE, and ackA The majority by far of scientific knowledge of E. coli is derived from investigations in complex medium such as Luria broth rather than mineral salts medium using low concentrations of sugar substrates (typically 0.2% w/v; 11 mM) rather than the 5% (w/v) glucose (278 mM) and 10% w/v (555 mM) used in the studies reported herein. Large amounts of sugar are required to produce commercially significant levels of product. Previous researchers have described the construction of many E. coli derivatives for succinate production in complex medium (Table 1). With complex medium, rational design based on primary pathways has been reasonably successful for academic demonstrations of metabolic engineering. However, the use of complex nutrients for production of bacterial fermentation products increases the cost of materials, the cost of purification, and the cost associated with waste disposal. Use of mineral salts medium without complex media components should be much more cost-effective.

E. coli C grows well in NBS mineral salts medium containing glucose and produces a mixture of lactate, acetate, ethanol and succinate as fermentation products (FIG. 1A; Table 3). In contrast to other studies with E. coli (Table 1), the studies reported herein have focused on the development of strains that are able to convert high level of sugars into succinate using mineral salts medium to minimize the costs of materials, succinate purification, and waste disposal. By inspection of FIG. 1 illustrating the generally accepted standard fermentation pathways for E. coli, a rational design for the metabolic engineering of a succinate-producing strain was devised in which deletions were made in genes encoding the terminal steps for all alternative products: lactate (ldhA), ethanol (adhE) and acetate (ackA). Results from this metabolic engineering by rational design were completely unexpected. The resulting strain (KJ012) grew very poorly under anaerobic conditions in mineral salts medium containing 5% glucose (278 mM) and produced acetate instead of succinate as the primary fermentation product. Counter to expectations from rational design, succinate remained as a minor product. Molar yields of succinate based on metabolized glucose were unchanged as a result of these mutations, 0.2 mol succinate per mol glucose for the parent and KJ012 during fermentation in NBS mineral salts medium containing 5% glucose. We confirmed that NBS mineral salts medium contains all mineral nutrients needed for the growth of KJ012 by incubating under aerobic conditions (aerobic shaken flask; 5% glucose). In aerobic shaken flasks, cell yields for KJ012 were 5-fold higher than during anaerobic growth and 75% that of the E. coli C (parent) during anaerobic growth. These results also confirmed that all central biosynthetic pathways remain functional in KJ012.

When complex nutrients were present (Luria broth), fermentative succinate production by KJ012 increased 20-fold as compared to KJ012 in minimal salts medium and the molar yield for succinate increased by 3.5-fold. Clearly, rational design based on primary pathways is better suited to academic demonstrations or to design processes intended for use with complex nutrients.

The basis for the poor growth, poor succinate production, and the increase in acetate production by KJ012(ΔldhA::FRT ΔadhE::FRT ΔackA::FRT) during anaerobic metabolism in mineral salts medium is unknown. These are unexpected consequences that resulted from metabolic engineering using rational design based on standard pathway charts. In minimal medium, rationale designs for metabolic engineering clearly are not predictable. The resulting strain, KJ012, was inferior to the parent in growth and no better than the parent for succinate production.

Development of KJ017 for Succinate Production by Growth-Based Selection of KJ012

KJ012(ΔldhA::FRT ΔadhE::FRT ΔackA::FRT) grew poorly in comparison to the parent E. coli C, exhibited lower rates of succinate production, and provide no better molar yields (Table 3). Despite these results, serial transfer of this strain was tried as a method to co-select improved growth and succinate production based on the following rationale. The primary pathway for the glucose fermentation into succinate (FIG. 1A and FIG. 2A.) is generally thought to use phosphoenolpyruvate carboxylase (ppc) for the carboxylation step (Unden and Kleefeld, 2004; Fraenkel 1996; Keseler et al., 2005; Millard et al., 1996; Gottschalk, 1985; Karp et al., 2007). This carboxylating enzyme does not conserve the high energy phosphate in phosphoenolpyruvate and reduces the net ATP available for growth. Alternative pathways for succinate production can be envisioned using the repertoire of known E. coli genes that could increase ATP yields and could thereby increase growth (FIG. 1A; FIGS. 2B, 2C and 2D). However, none of these alternative routes has been shown to function for succinate production during fermentation with native strains of E. coli. Key enzymes in these alternative routes are repressed by glucose and are normally active during gluconeogenesis. Typically, levels of these gluconeogenic enzymes vary inversely with the availability of glucose and other metabolites (Goldie and Sanwal, 1980a; Wright and Sanwal, 1969; Sanwal and Smando, 1969a) and function in the reverse direction, decarboxylation (Keseler et al., 2005; Oh et al., 2002; Kao et al., 2005; Stols and Donnelly, 1997; Samuelov et al., 1991; Sanwal, 1970a; Delbaere et al., 2004; Goldie and Sanwal, 1980b; Sanwal and Smando, 1969b; Sanwal 1970b).

The key enzyme for one of these, NADH-linked malic enzyme (sfcA) (FIG. 2B), has been demonstrated to be capable of increasing succinate production in E. coli but required overexpression from a plasmid to do so (Stols and Donnelly, 1997). However, none of these alternative pathways would be expected to be functional in native strains of E. coli or KJ012 during anaerobic growth with high levels of glucose. Serial transfers of KJ012 with selection for improved growth offered an opportunity to select for mutational activation of alternative routes for succinate production (FIG. 1B) that maintained redox balance and increased ATP yields.

Figure 3A:
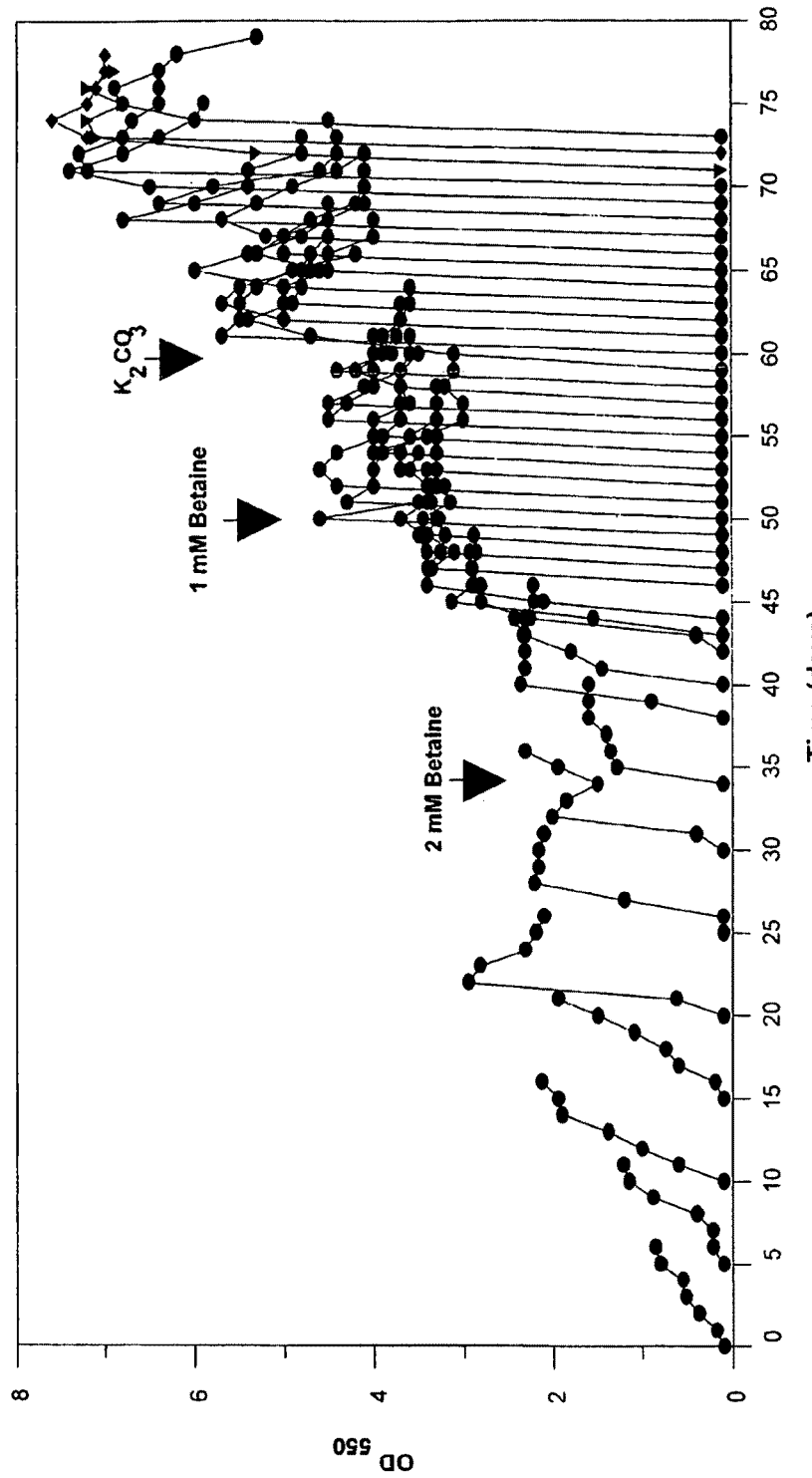
Figure 4A:
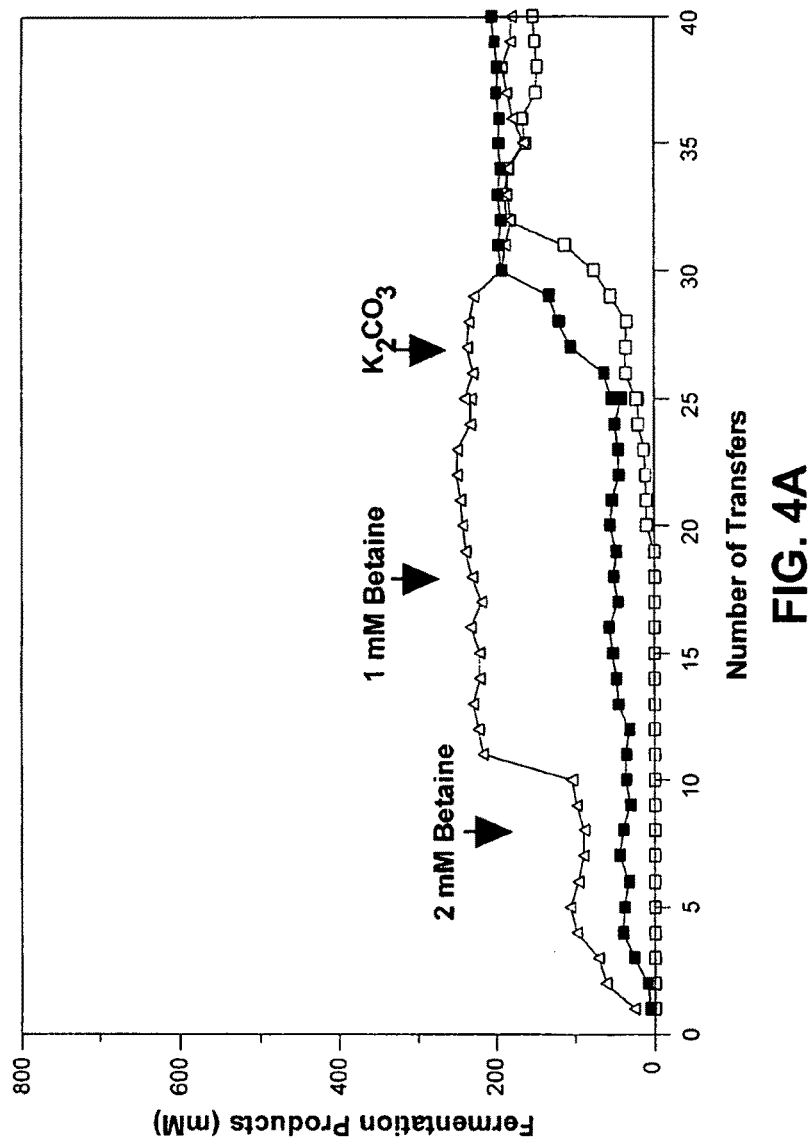
FIGS. 4A-4F. Summary of fermentation products during the metabolic evolution of strains for succinate and malate production. Cultures were supplemented with sodium acetate as indicated. Black arrows represent the transition between fermentation conditions as indicated by text. No formate and only small amounts of lactate were detected during metabolic evolution of KJ032. No formate and lactate were detected during metabolic evolution of KJ070 and KJ072.
Figure 4B:
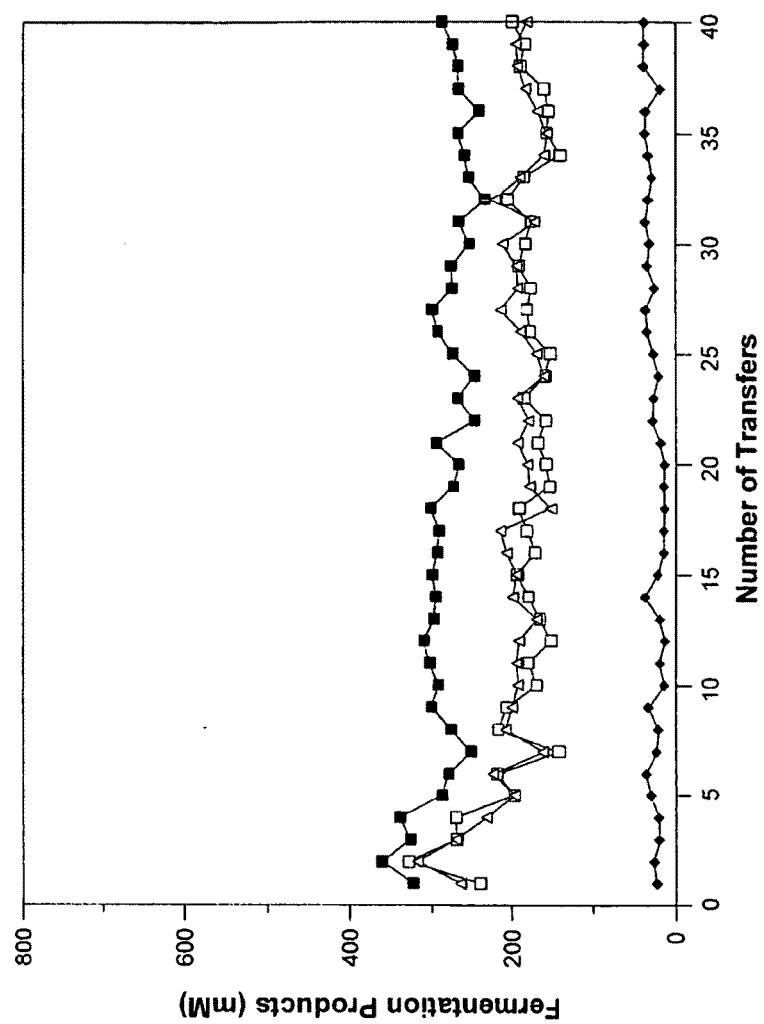
Figure 5:
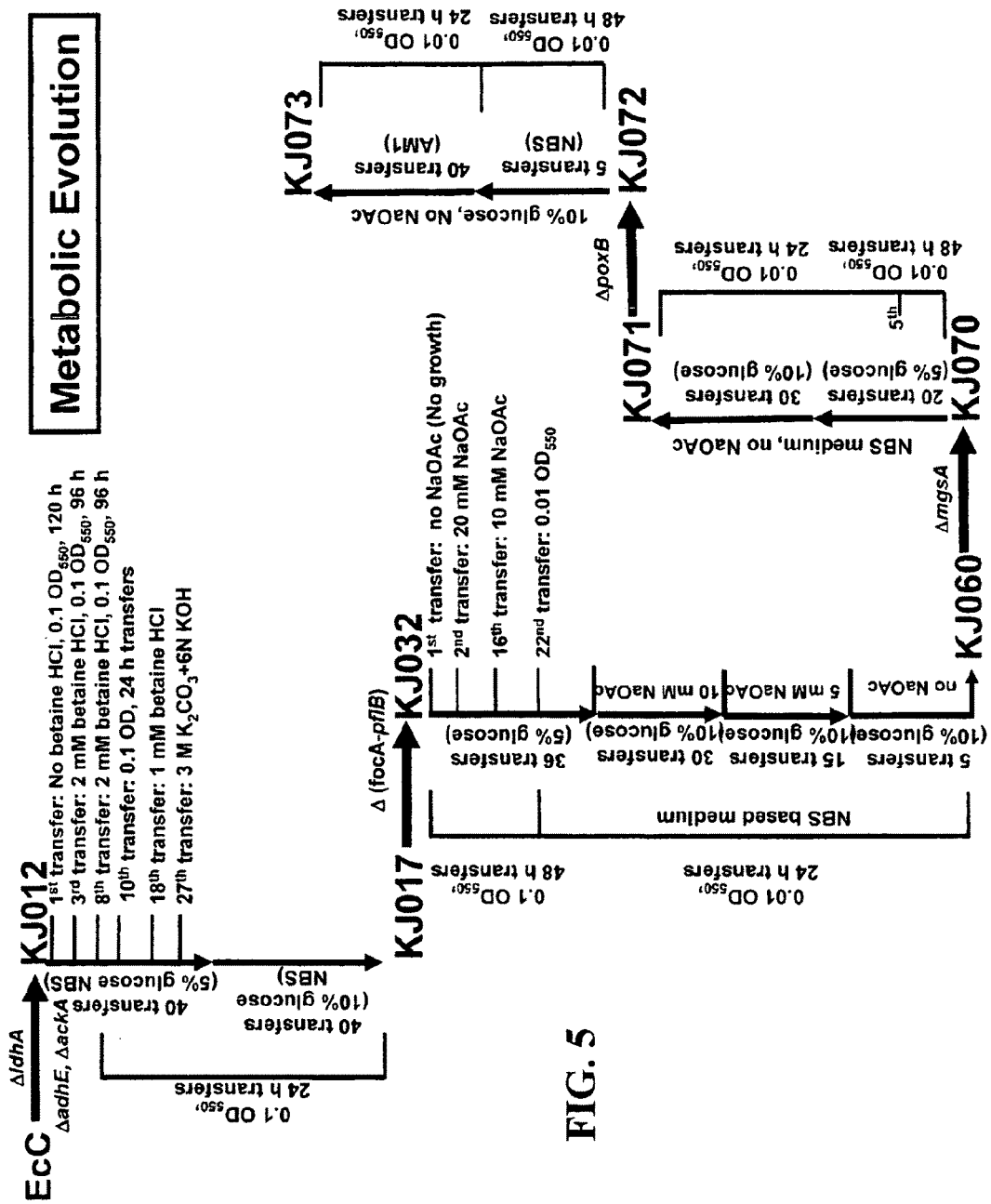
FIG. 5. Diagram summarizing steps in the genetic engineering and metabolic evolution of *E. coli* C as a biocatalyst for succinate and malate production. This process represents 261 serial transfers providing over 2000 generations of growth-based selection. Clones were isolated from the final culture of each regimen and assigned strain designations, shown in parenthesis in Table 3.

KJ012 was serially transferred in NBS glucose medium under fermentative conditions as rapidly as growth permitted (FIG. 3A; FIG. 4A; FIG. 5). Growth remained slow with 4-5 days of required incubation between the first 9 transfers, then dramatically increased allowing transfers to be made at 24 h-intervals. This event was accompanied by an increase in acetate (FIG. 4A) with little improvement in succinate production. After 27 transfer (60 days), KOH was replaced with a 1:1 mixture of 3M $K_2CO_3$ and 6N KOH to provide additional carbon dioxide (100 mM initially added to all NBS mineral salts medium). Continuing transfers led to improvements in succinate production. A total of 40 transfers were made in 5% glucose (227 mM), followed by another 40 transfers in 10% glucose (555 mM). During the transfers in 10% glucose, succinate yields remained approximately 0.7 mol per mole of glucose metabolized with lactate, acetate, and formate as co-products (Table 3). This yield was 3-fold higher than E. coli C and KJ012. A clone was isolated and designated KJ017. Selection for improvements in the growth of KJ012 to produce KJ017 co-selected for improvements in succinate production (rate, titer, and molar yield).

Physiological Basis for Increased Succinate Production by KJ017

Figure 6:
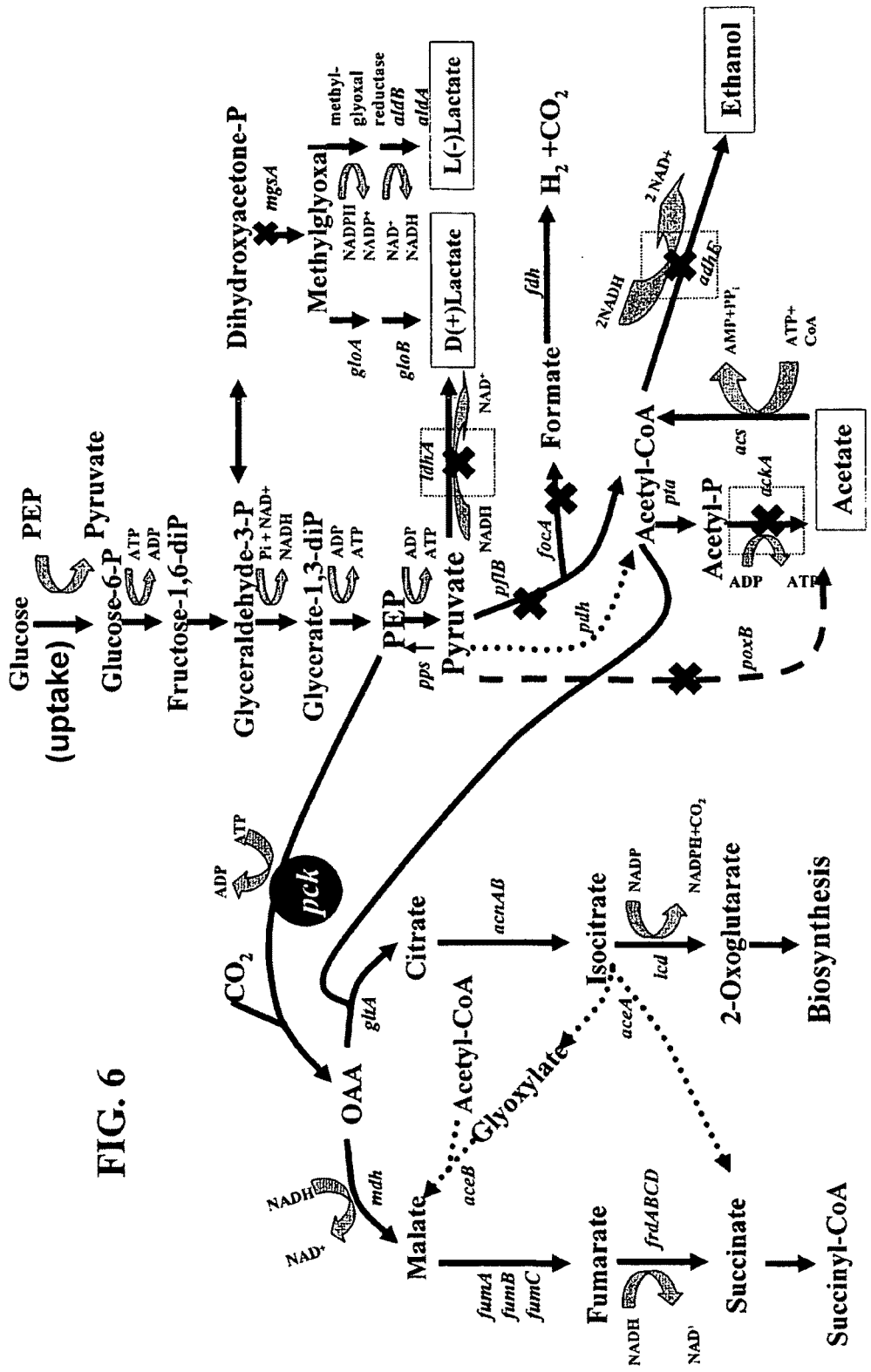
FIG. 6. Fermentation of glucose and associated pathways. Central metabolism indicating genes deleted in constructs engineered for succinate production. Solid arrows represent central fermentative pathways. Dashed arrow represents the microaerophilic pathway for pyruvate oxidation to acetate (poxB). Dotted arrows show pathways that normally function during aerobic metabolism, pyruvate dehydrogenase (pdh) and the glyoxylate bypass (aceAB). Boxed crosses represent the three initial gene deletions (ldhA, adhE, ackA) that were used to construct KJ012 and KJ017. Plain crosses mark addition genes that were deleted during the construction of KJ017 derivatives: KJ032 (ldhA, adhE, ackA, focA, pflB), and KJ070 (ldhA, adhE, ackA, focA, pflB, mgsA), and KJ072 (ldhA, adhE, ackA, focA, pflB, mgsA, poxB). Genes and enzymes: ldhA, lactate dehydrogenase; focA, formate transporter; pflB, pyruvate-formate lyase; pta, phosphate acetyltransferase; ackA, acetate kinase; adhE, alcohol dehydrogenase; ppc, phosphoenolpyruvate carboxylase; pdh, pyruvate dehydrogenase complex; gltA, citrate synthase; mdh, malate dehydrogenase; fumA, fumB, and fumC, fumarase isozymes; frdABCD, fumarate reductase; fdh, formate dehydrogenase; mgsA, methylglyoxal synthase; gloAB, glyoxylase I and II; poxB, pyruvate oxidase; aceA, isocitrate lyase; aceB, malate synthase; acnAB, aconitase; and acs, acetyl-CoA synthetase.

Succinate produced by E. coli using the pathway generally regarded as the native fermentation pathway (phosphoenolpyruvate carboxylase; ppc) waste the energy of phosphoenolpyruvate by producing inorganic phosphate. One ATP is lost per succinate produced by this pathway (FIG. 1; FIG. 6). Conserving this energy as ATP by using alternative enzyme systems represents an opportunity to increase cell growth and co-select for increased succinate production. Based on known genes in E. coli, three other enzyme routes for succinate production were envisioned that would conserve ATP and could thereby increase growth (FIG. 1; FIG. 6). However, all carboxylation steps in these alternative routes are thought to function in the reverse direction (decarboxylation) primarily for gluconeogenesis during growth on substrates such as organic acids (Keseler et al., 2005; Oh et al., 2002; Kao et al., 2005; Stols and Donnelly, 1997; Samuelov et al., 1991; Sanwal, 1970a; Delbaere et al., 2004; Goldie and Sanwal, 1980b; Sanwal and Smando, 1969b; Sanwal 1970b). To test the hypothesis that growth-based selection to develop KJ017 has indeed activated one or more of these alternative routes, specific activities of the key carboxylation steps were compared (Table 4). Three of these were similar or lower in E. coli C, KJ012, and KJ017. The energy conserving phosphoenolpyruvate carboxykinase (pck) was increased by 4-fold in KJ017 as compared to KJ012, consistent with a hypothesis that selection for improved growth would co-select for increased production of succinate through increasing ATP yields, a consequence of increasing the expression of an energy-conserving route for succinate production.

Figure 3B:
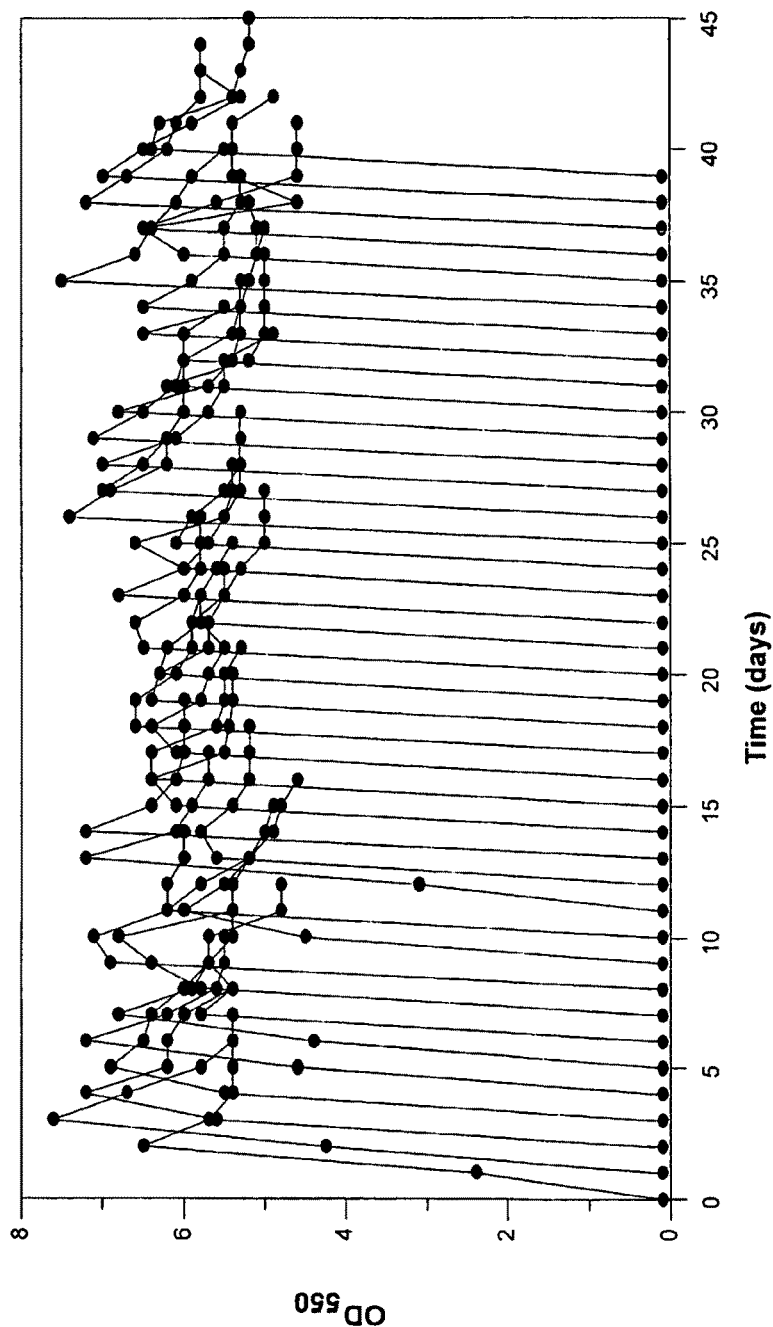

Further growth-based selections and additional gene deletions were used to construct many additional strains with further improvements in growth and succinate production (FIG. 3 and FIG. 4). Enzyme levels in one of these was also examined, KJ073. In this strain, the in vitro activity of phosphoenolpyruvate carboxykinase was further increased to 8-fold that of KJ017 while the other carboxylating enzymes remained essentially unchanged (Table 4).

The pck and surrounding regions were cloned from KJ012 and KJ073, and sequenced. No changes were found in the coding region. Absent post-translational modifications, the catalytic properties of the enzyme should be unchanged. A single mutation was detected in the pck promoter region, G to A at −64 by site relative to the translation start site. This mutation was behind the transcription start site which is −139 by site relative to the translational start site. Restoring this sequence (A to G) in KJ073 to that of E. coli C did not affect cell growth, fermentation, or succinate production indicating that this mutation is not essential (data not shown). RT-PCR confirmed that message levels were elevated in KJ073. These results are consistent with a regulatory mutation as the basis for increased expression of pck.

Previous investigators have noted that the kinetic parameters of phosphoenolpyruvate carboxylase (ppc) and phosphoenolpyruvate carboxykinase (pck) may have important effects on carboxylation and succinate production (Millard et al., 1996; Kim et al., 2004). The Km towards bicarbonate for E. coli phosphoenolpyruvate carboxylase (ppc) is 0.15 mM (Morikawa et al., 1980), 9-fold lower (13 mM) than E. coli phosphoenolpyruvate carboxykinase (pck) (Krebs and Bridger 1980). Although overexpressing pck from E. coli in multi-copy plasmid increased phosphoenolpyruvate carboxykinase activity by 50-fold, it was reported to have no effect on succinate production (Millard et al., 1996). Succinate production was also not increased when phosphoenolpyruvate carboxykinase from *Anaerobiospirillum succiniciproducens* was overexpressed in *E. coli* K 12 (Kim et al., 2004). This enzyme also has a high Km for bicarbonate (30 mM; Laivenieks et al., 1997). However, when *A. succiniciproducens* pck was overexpressed in a ppc mutant of *E. coli* K12, succinate production was increased 6.5-fold (Kim et al., 2004). In KJ017 and subsequent derivatives, phosphoenolpyruvate carboxykinase is clearly the dominant carboxylating activity even in the presence of functional native phosphoenolpyruvate carboxylase.

Results from enzyme measurements of *E. coli* C were quite surprising. The enzyme generally regarded as the dominant carboxylating activity for succinate production by native *E. coli* (phosphoenolpyruvate carboxylase; ppc) during growth (Unden and Kleefeld, 2004; Fraenkel 1996; Keseler et al., 2005; Millard et al., 1996; Gottschalk 1985; Karp et al., 2007) was not the most active enzyme in vitro for *E. coli* C. Thus the generally accepted metabolic pathways for *E. coli* (Unden and Kleefeld, 2004; Fraenkel 1996; Sanchez et al., 2006; Cox et al., 2006; Vemuri et al., 2002a; Wang et al, 2006; Sanchez et al., 2005ab; Gokarn et al., 2000; Karp et al., 2007) upon which rational design of metabolic engineering and estimates of metabolic flux are typically based may not accurately reflect metabolism in all strains. Under substrate-saturating conditions in vitro, phosphoenolpyruvate carboxykinase activity was the most active. In *E. coli* K12, activities for both phosphoenolpyruvate carboxylase and phosphoenolpyruvate carboxykinase were reported to be equal in vitro (140 nm min$^{-1}$ mg$^{-1}$ cell protein; Van der Werf et al., 1997) with the former serving as the primary route to succinate.

Previous studies showed that the overexpression of a native ppc gene in *E. coli* resulted in higher specific succinate production (Millard et al., 2000), higher specific growth rate, and lower specific acetate production due to more carboxylation of PEP to replenish TCA cycle intermediates (Farmer and Liao, 1997). However, since PEP is required for the glucose transport system, overexpressing ppc also decreases the glucose uptake rate by 15-40% without significantly increasing succinate yield (per glucose) as compared to an isogenic control (Chao and Liao, 1993; Gokarn et al., 2000). This failure of the native phosphoenolpyruvate carboxylase to increase succinate yields diverted most research attention to a new metabolic design, over expression of the PYC (pyruvate carboxylase) from *Lactobacillus lactis* or *Rhizobium etli* as the carboxylating step (Vemuri et al., 2002ab; Gokarn et al., 2000; Lin et al., 2005abc) rather than pursuing further work with the native repertoire of *E. coli* genes.

Rumen bacteria such as *Actinobacillus succinogenes* produce succinate as a primary product during glucose fermentation using the energy conserving phosphoenolpyruvate carboxykinase for carboxylation (Kim et al., 2004; McKinlay et al., 2005; McKinlay and Vieille, 2008). Reported activities for this organism are 5-fold those of KJ017 and half of that obtained by continued growth-based selection (metabolic evolution) of KJ073. Thus by using a combination of metabolic engineering (ldhA adhE ackA) and metabolic evolution (growth-based selection for increased efficiency of ATP production), the studies reported herein demonstrate the development of succinate-producing strains of *E. coli* that resemble a rumen organism such as *A. succinogenes* by using only the native repertoire of *E. coli* genes. Despite prior reports that over expression of the *E. coli* phosphoenolpyruvate carboxylase (ppc) is not helpful for succinate production in the absence of a mutation in phosphoenolpyruvate synthase (Chao and Liao, 1993; Kim et al., 2004; Gokarn et al., 2000; Millard et al., 1996), KJ017 and derivatives have been engineered to use phosphoenolpyruvate carboxykinase as the primary route for succinate and malate production.

Construction of KJ032 and KJ060

During growth with 10% (w/v) glucose, unwanted co-products (acetate, formate, and lactate) were abundant in fermentations with KJ017(ΔldhA::FRT ΔadhE::FRT ΔackA::FRT) despite the deletion of genes encoding the primary lactate dehydrogenase (ldhA) and acetate kinase (ackA) activities (Table 3). Production of lactate and acetate could also result in higher ATP yields, a basis for growth-based selection (FIG. 1A).

Figure 4C:
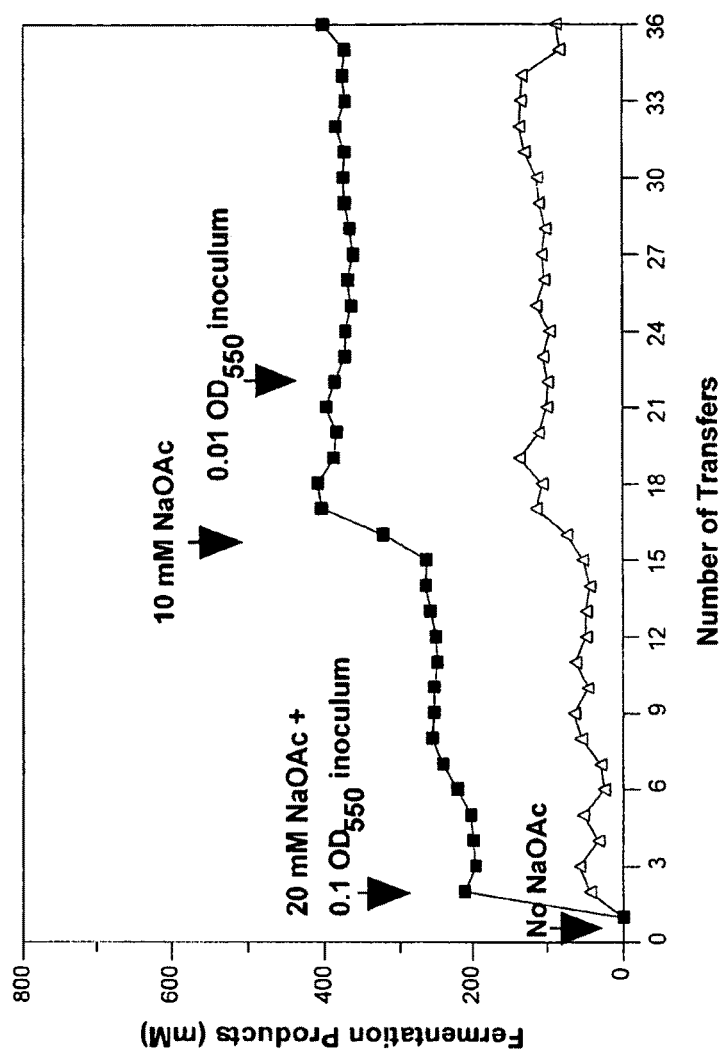
Figure 4D:
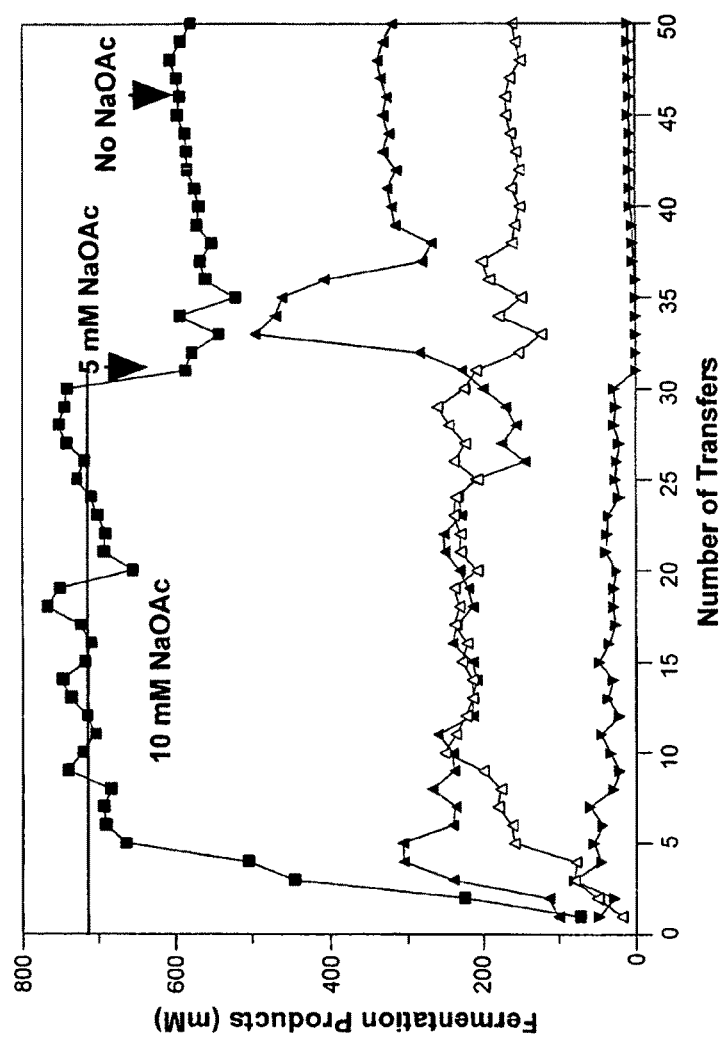

The gene encoding pyruvate formatelyase (pflB) was deleted from KJ017 to eliminate the loss of reductant as formate and an excess acetyl-CoA, a potential source of acetate. The upstream formate transporter (focA) in this operon was also deleted. As expected, this deleted strain (KJ032) did not grow without acetate confirming that this is the primary route for acetyl-CoA production in KJ017 (FIG. 3C). Deletion of pflB is well-known to cause acetate auxotrophy under anaerobic conditions (Sawers and Bock, 1988). Growth and succinate production by KJ032 were restored by the addition of 20 mM acetate (FIG. 3C, FIG. 4C, and FIG. 5). Production of formate and acetate were substantially reduced as a result of pflB (and focA) deletion. Although this strain required acetate for growth, additional acetate was also produced during fermentation. The same phenomenon was previously reported for pflB-deleted strains during the construction of *E. coli* K-12 biocatalysts for pyruvate production (Causey et al., 2004). Lactate levels were also reduced in KJ032 (Table 3; FIG. 4C). Subsequent transfers were accompanied by improvements in growth and succinate production. Added acetate was reduced, inocula size was reduced, and glucose concentration was doubled (10% w/v) during subsequent transfers (FIG. 4D). After reducing the amount of acetate to 5 mM, an unstable population emerged that produced elevated levels of malate at the expense of succinate. After further transfers, acetate was omitted and a strain was developed that was no longer auxotrophic for acetate, presumably due to increased expression of another gene. However, succinate yields declined upon elimination of added acetate while malate and acetate levels increased. The source of acetate and basis for the increase in malate are unknown. A small amount of pyruvate was also produced. A clone was isolated from the last transfer and designated, KJ060(ΔldhA:: FRT ΔadhE::FRT ΔackA::FRT ΔfocA-pflB::FRT). This strain produced 1 mole of succinate per mole of glucose metabolized in NBS mineral salts medium with 10% glucose.

Construction of KJ070 and KJ071 by Deletion of Methylglyoxal Synthase (mgsA)

Figure 4E:
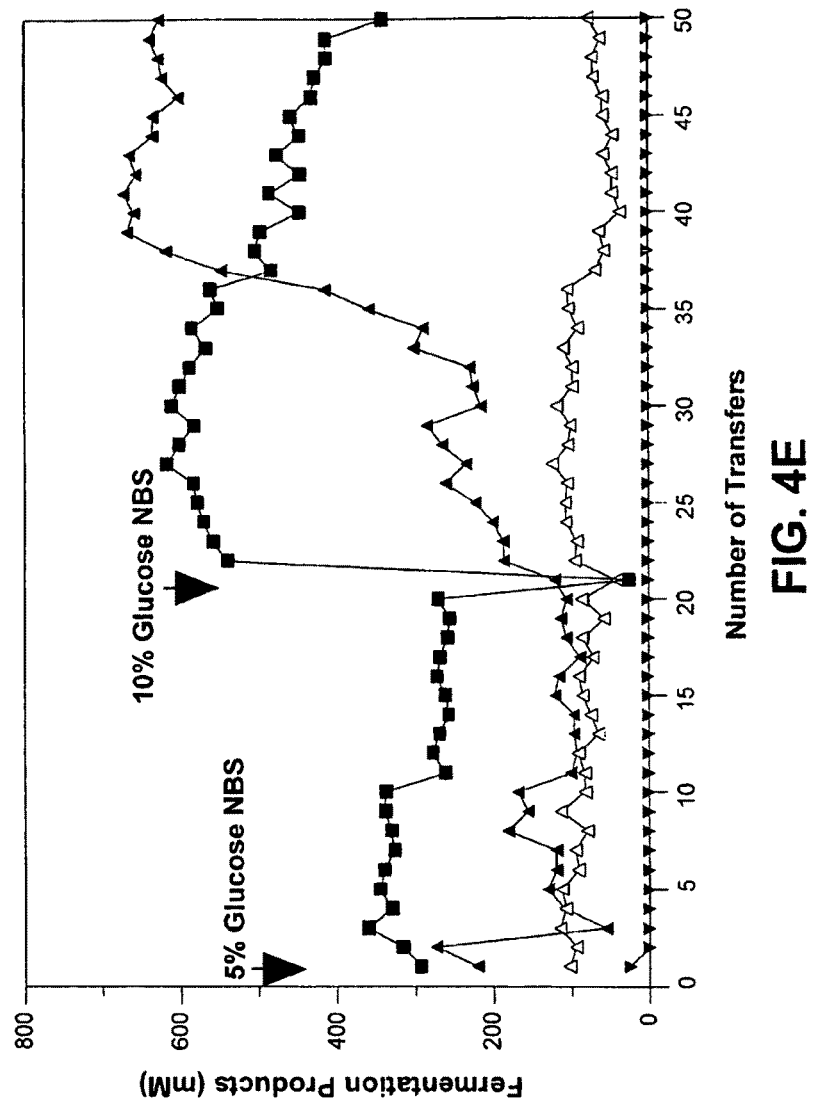

The small amount of lactate present in the fermentation broths of various strains is presumed to originate from the methylglyoxal synthase pathway (FIG. 6; Grabar et al. 2006). Although this represents a small loss of yield, lactate production by this pathway is indicative of methylglyoxal accumulation, an inhibitor of both growth and glycolysis (Egyud and Szent-Gyorgyi, 1966; Grabar et al., 2006; Hopper and Cooper, 1971). Production of methylglyoxal and lactate were eliminated by deleting the mgsA gene (methylglyoxal synthase) in KJ060 to produce KJ070(ΔldhA::FRT ΔadhE::FRT ΔackA::FRT ΔfocA-pflB::FRT ΔmgsA). Strain KJ070 was initially subcultured in 5% (w/v) glucose (FIG. 4E and FIG. 5). Deletion of mgsA is presumed to have increased glycolytic flux as evidenced by the accumulation of pyruvate in the medium (Table 3). This increase in glycolytic flux may also be responsible for the further decline in the succinate/malate ratio due to increased production of oxaloacetate, an allosteric inhibitor of fumarate reductase (Iverson et al., 2002; Sanwal, 1970c).

At transfer 21, glucose was doubled to 10% (w/v) and transfers continued. This higher level of glucose and subsequent transfers resulted in further increases in malate production, exceeding succinate in latter transfers (FIG. 4E). Increased production of malate versus succinate in 10% w/v glucose is also consistent with increased glycolytic flux and inhibition of fumarate reductase by oxaloacetate. At transfer 50, 1.3 moles of malate and 0.71 moles of succinate were produced per mole of glucose metabolized (Table 3). Significant amounts of acetate were also produced. A new strain was isolated from the final subculture and designated KJ071 (ΔldhA::FRT ΔadhE::FRT ΔackA::FRT ΔfocA-pflB::FRT ΔmgsA). This strain may be useful for malate production.

Construction of KJ072 and KJ073 by Deletion of poxB

Figure 4F:
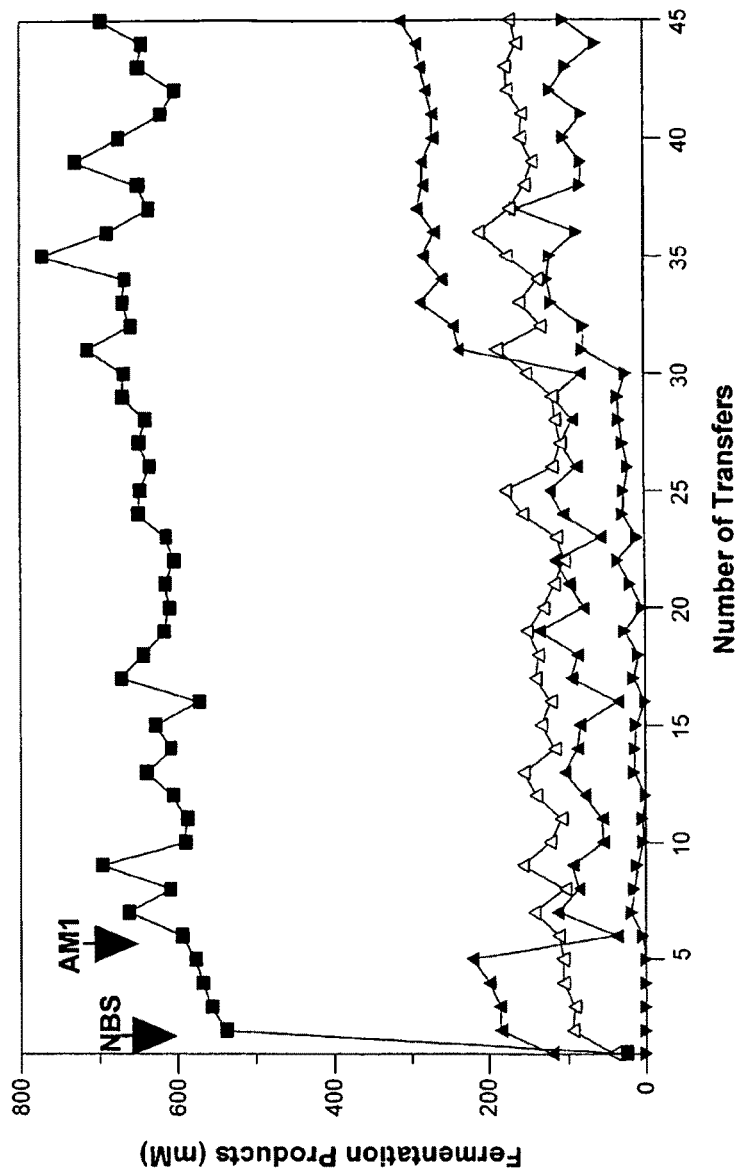

Although conversion of glucose to acetate is redox neutral, partitioning of carbon to acetate decreases the yield of succinate and malate. Pyruvate oxidase (poxB) represents a potential source of acetate and $CO_2$ during incubation under microaerophilic conditions (Causey et al., 2004). Although it should not function to oxidize pyruvate under anaerobic condition, poxB was targeted for gene deletion (FIG. 6). As expected, deletion of poxB to produce KJ072 (ΔldhA::FRT ΔadhE::FRT ΔackA::FRT ΔfocA-pflB::FRT ΔmgsA ΔpoxB) did not reduce acetate production indicating that alternative pathways are involved in acetate production. However, eliminating poxB resulted in unexpected changes in fermentation products, an increase in succinate and decrease in malate (Table 3; FIG. 4F). The mechanism for this improvement in succinate production is unknown but may be related to other activities of pyruvate oxidase such as acetoin production, decarboxylation, and carboligation (Ajl and Werkman, 1948; Chang and Cronan, 2000).

Strain KJ072 was subjected to 40 further rounds of metabolic evolution in AM1 medium, a lower salt medium, with 10% (w/v) glucose (Table 3; FIG. 4F, and FIG. 5). Improvements in growth, cell yield and succinate production were observed during these transfers. Malate, pyruvate and acetate levels also increased. A clone was isolated from the final transfer and designated KJ073(ΔldhA::FRT ΔadhE::FRT ΔackA::FRT ΔpflB::FRT ΔmgsA ΔpoxB). This strain retained the phosphenolpyruvate carboxykinase route for carboxylation (Table 4). In vitro activity of this strain was 45-fold higher than that of KJ012 and 10-fold higher than KJ017 providing further evidence for the tight coupling of energy conservation to succinate production and growth and further establishing the basis used for selection.

Fermentation of KJ060 and KJ073 in AM1 Medium Containing 10% (w/v) Glucose

Figure 7A:
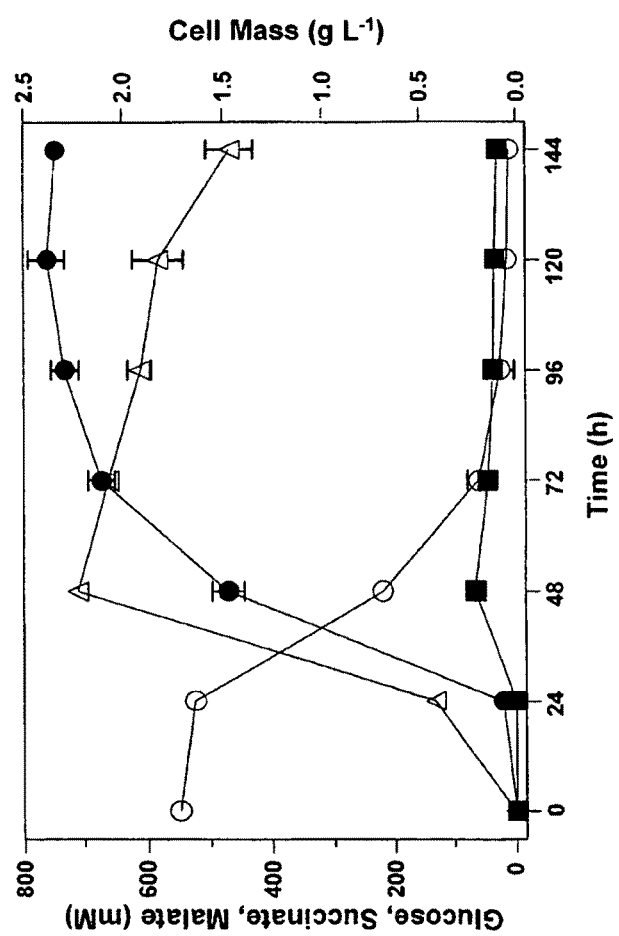
FIGS. 7A-7C. Production of succinate and malate in mineral salts media (10% glucose) by derivatives of *E. coli* C.
Figure 7B:
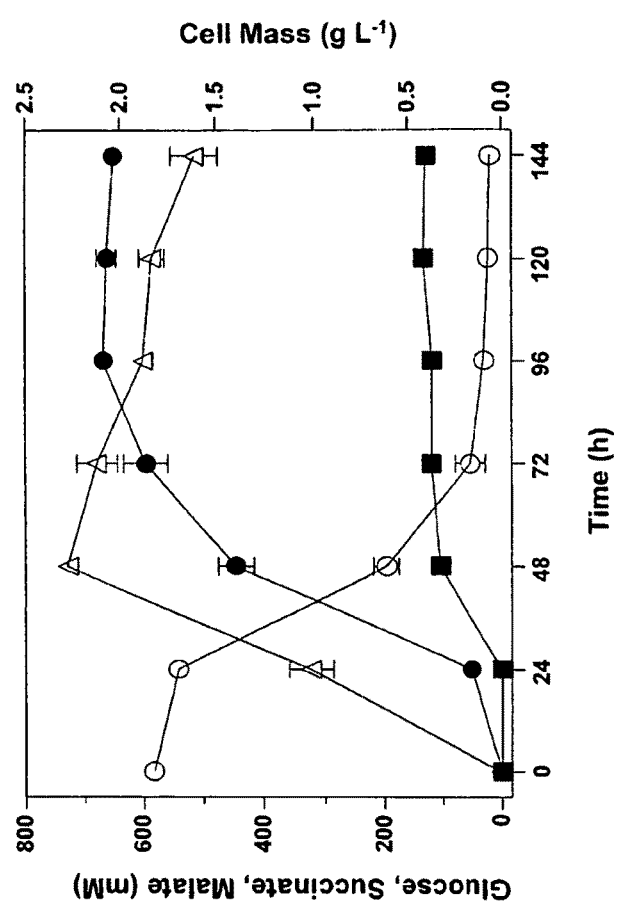
Figure 7C:
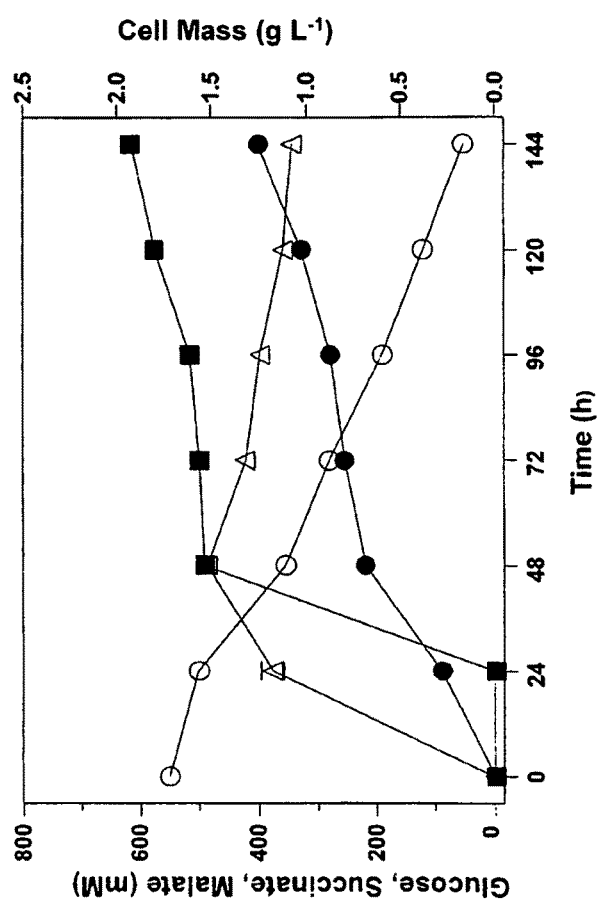
Figure 8:
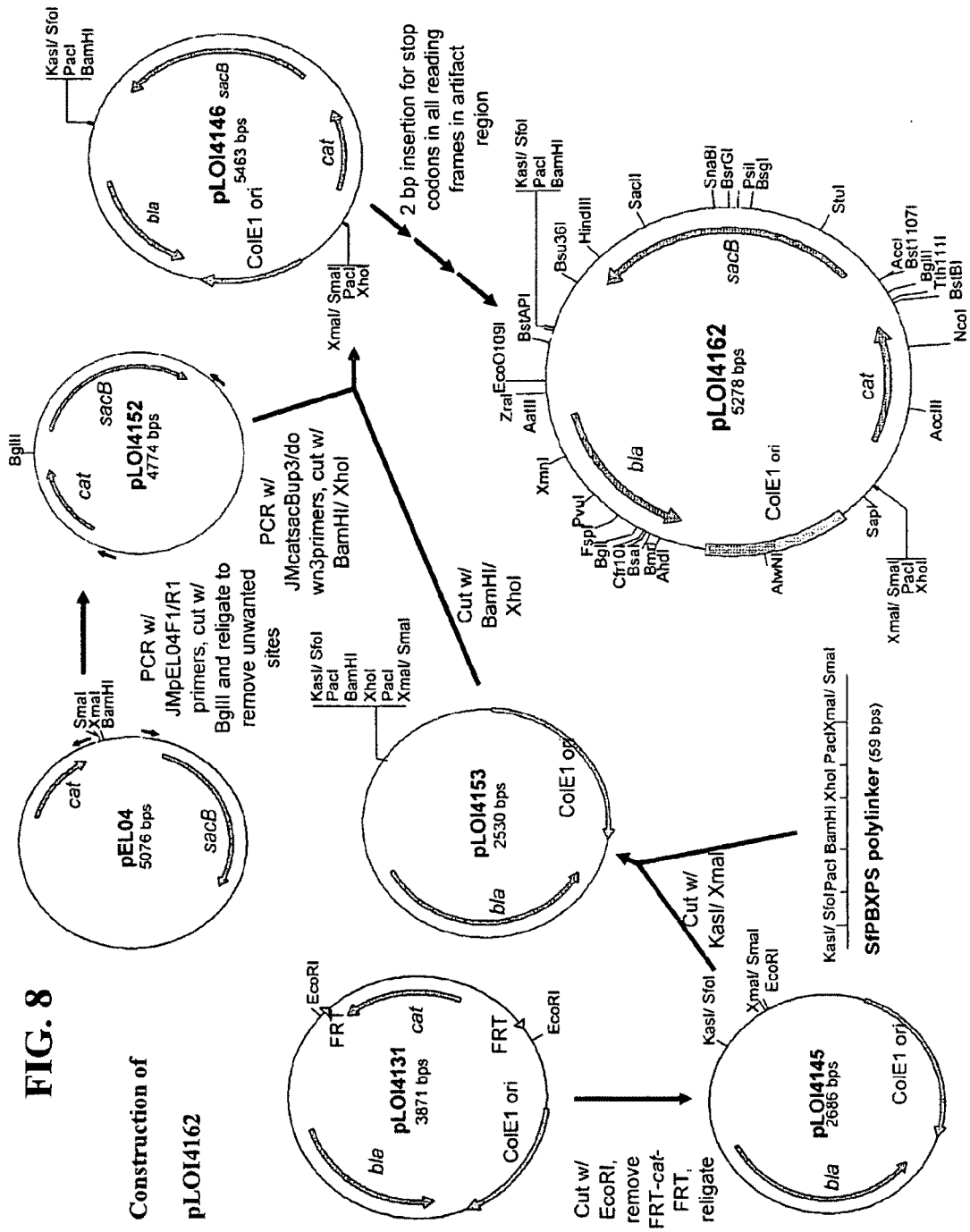
FIG. 8. Construction of pLOI4162. Short solid arrows associated with pEL04 and pLOI4152 represent primers used for DNA amplification.

FIG. 7 shows batch fermentations with KJ060 and KJ073, the two best biocatalysts for succinate production. Although growth was completed within the initial 48 h of incubation, succinate production continued for 96 h. One-third of succinate production occurred in the absence of cell growth. These strains produced succinate titers of 668-733 mM, with a molar yield of 1.2-1.6 based on glucose metabolized. With AM1 medium, yields were typically higher than with NBS mineral salts medium. Acetate, malate, and pyruvate accumulated as undesirable co-products and detracted from the potential yield of succinate (Table 3). The maximum theoretical yield of succinate from glucose and $CO_2$ (excess) is 1.71 mol per mole glucose based on the following equation:

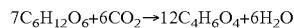

However, there is no direct succinate pathway in *E. coli* that achieves this yield (FIG. 6).

Conversion of Other Substrates to Succinate

Although this study primarily focused on the conversion of glucose to succinate. It is well known that *E. coli* has the native ability to metabolize all hexose and pentose sugars that are constituents of plant cell walls (Asghari et al., 1996; Underwood et al., 2004). Some strains of *E. coli* can also metabolize sucrose (Moniruzzaman et al., 1997). Strain KJ073 was tested for utilization of 2% sugars of hexoses and pentoses in serum tubes. In all cases, these sugars were converted primarily to succinate. Strain KJ073 also metabolized glycerol to succinate. During incubation with 2% glycerol, 143 mM glycerol was metabolized to produce 127 mM succinate with a molar yield of 0.89, 89% of the theoretical maximum.

Production of Malate in NBS Medium Containing 1 mM Betaine and 10% Glucose

During growth-based selections, cultures were observed to vary in their production of malate (Table 3), a potentially useful alternative product. Malate was the most abundant product from KJ071 with 10% glucose (Table 3; FIG. 4E), almost double that of succinate. This strain produced 516 mM malate with a molar yield of 1.44 based on metabolized glucose (Table 3).

Conclusions

Figure 1B:
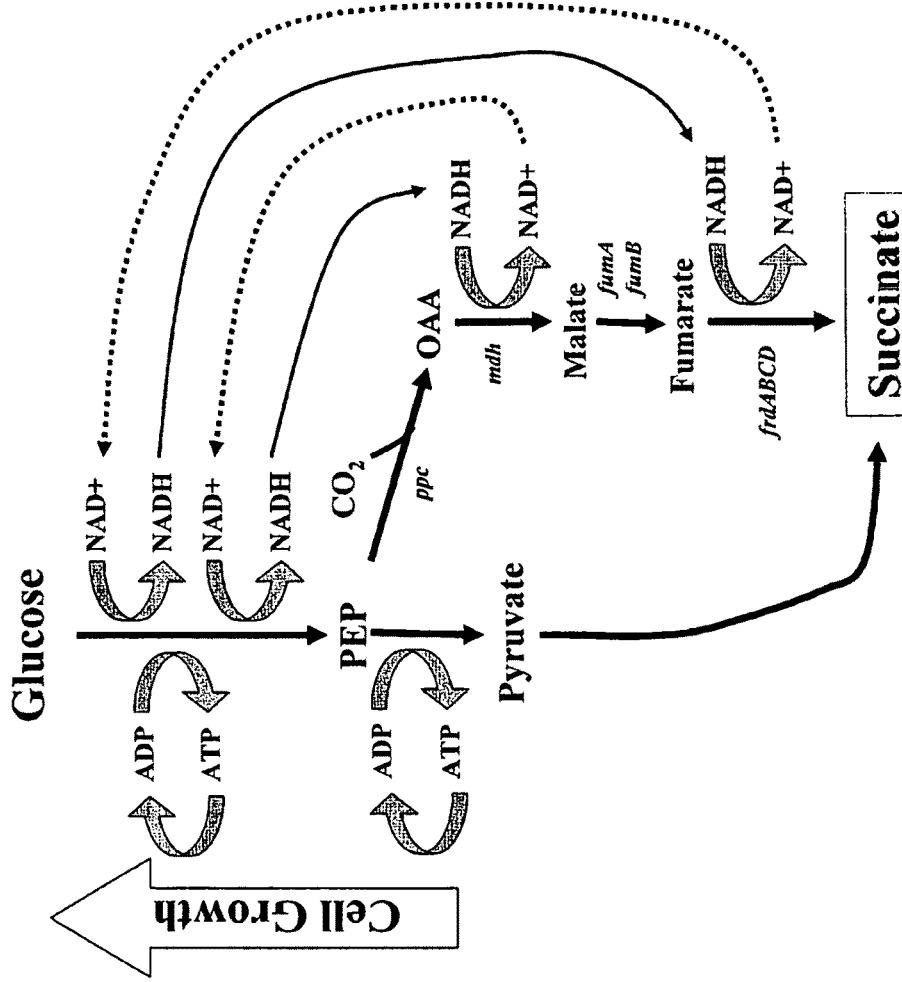

The fermentative metabolism of *E. coli* has been shown to be remarkably adaptable. Derivatives were engineered and evolved to circumvent numerous deletions of genes concerned with native fermentation pathways and increase fluxes through remaining enzymes to maintain redox balance, increase the efficiency of ATP production, and increase growth. Though much more challenging, cells can make such adaptive changes in mineral salts media while balancing carbon partitioning to provide all biosynthetic needs. After eliminating the primary routes for NADH oxidation (lactate dehydrogenase, alcohol dehydrogenase) and acetate production (acetate kinase), growth and ATP production remain linked to NADH oxidation and the production of malate or succinate for redox balance (FIG. 1B). Anaerobic growth-based selections ensure redox balance and select for increased efficiency and increased rates of ATP production, the basis for increased growth. This selection for redox balance and ATP production cannot readily distinguish between malate and succinate as end products, since the precursors of both serve as electron acceptors. During these investigations, one strain was developed in (KJ071) that produces more malate than succinate. This strain and further derivatives may be useful for malate production. Other strains such as KJ073 and KJ060 produce succinate as the primary product at yields of 1.2 to 1.6 moles per mole of glucose.

Deletion of pflB, the primary source of acetyl~CoA during anerobic growth, resulted in an auxotrophic requirement for acetate (Sawers and Bock, 1988). This requirement was eliminated through metabolic evolution, presumably due to increased production of acetyl~CoA by other routes such as pyruvate dehydrogenase (de Graef et al., 1999). The metabolic source of the acetate or acetyl~CoA that replaced this auxotrophic need is unknown. Many shifts in metabolic products were unanticipated. The increase in malate during selections after deletion of mgsA is unexplained. Methylglyoxal is a metabolic inhibitor that is produced in response to an imbalance in metabolism (Grabar et al., 2006). Elimination of methylglyoxal production may have provided a growth-related advantage such as increased growth rate, a shorter lag after inoculation, etc. The reduction in malate and shift to higher succinate production after a poxB deletion was also surprising. Little change in the acetate level was observed indicating that either this enzyme was a minor source of acetate or that it was functionally replaced by other routes for acetate production. After deletion of poxB, succinate was again produced as the dominant dicarboxylic acid. With the best strains for succinate production, KJ060 and KJ073, malate and acetate remained as abundant co-products (Table 3; FIGS. 4D and 4F). Elimination of these represents a further opportunity to increase yields.

All previously engineered *E. coli* developed for succinate production have used complex media and plasmids with antibiotics for maintenance. Most have achieved only low titers of succinate in simple batch fermentations, requiring more complex processes to achieve high titers (Table 1). A variety of genetic approaches have been reported that increase succinate production from glucose by recombinant *E. coli* in complex medium. In our initial construct, growth and sugar metabolism were very poor in mineral salts medium but were very robust in complex medium (Luria broth). Complex media containing vitamins, amino acids, and other macromolecular precursors may mask potential regulatory problems in metabolism and biosynthesis that were created by metabolic engineering.

Many other investigators have also used heterologous genes and complicated processes that include sparging with gas ($CO_2$, $H_2$, $O_2$ or air) and dual aerobic and anaerobic process steps. This complexity of process and nutrients would be expected to increase the cost of construction, materials, purification, and waste disposal. In contrast, strains KJ060 and KJ073 produced high titers of succinate (600-700 mM) in simple batch fermentations (10% sugar) using mineral salts medium without any complex nutrients or foreign genes.

EXAMPLE 2

Microorganisms were deposited with the ARS Culture Collection as follows:

| Culture | Strain Designations | Deposit Date |
|---|---|---|
| KJ073 | B-50029 | Mar. 15, 2007 |
| KJ091 | B-50110 | Feb. 20, 2008 |
| KJ098 | B-50111 | Feb. 20, 2008 |
| KJ104 | B-50112 | Feb. 20, 2008 |
| KJ110 | B-50113 | Feb. 20, 2008 |
| KJ119 | B-50114 | Feb. 20, 2008 |
| KJ122 | B-50115 | Feb. 20, 2008 |
| KJ134 | B-50116 | Feb. 20, 2008 |

Materials and Methods
Strains, Media and Growth Conditions

New derivatives of *E. coli* C (ATCC 8739) were developed for succinate production using a unique combination of gene deletions coupled with growth-based selection. Strains, plasmids, and primers used in this study are summarized in Table 1. During strain construction, cultures were grown at 37° C. in modified Luria-Bertani (LB) broth (per liter: 10 g Difco tryptone, 5 g Difco yeast extract, 5 g sodium chloride) (Miller, 1992) and supplemented with antibiotics as appropriate (Jantama et al., 2008; Zhang et al., 2007). No genes encoding antibiotic resistance, plasmids, or foreign genes are present in the final strains developed for succinate production. After construction, strains were grown and maintained in AM1 medium (Martinez et al., 2007). This medium was supplemented with 100 mM $KHCO_3$ and glucose (as indicated). Betaine (1 mM) was also added when the initial glucose concentrations was 5% (w/v) or higher.

Deletion of FRT Markers in the adhE, ldhA, and focA-pflB Regions

The strategy used to make sequential gene deletions and remove the FRT markers from the adhE, ldhA and focA-pflB loci has been described previously (Datsenko and Wanner, 2000; Grabar et al., 2006; Jantama et al., 2008; Zhang et al., 2007). Plasmid pLOI4151 was used as a source of a cat-sacB cassette and Red recombinase (pKD46) was used to facilitate double-crossover, homologous recombination events. Chloramphenicol resistance was used to select for integration. Growth with sucrose was used to select for loss of sacB. With this approach, successive deletions were constructed to produce derivatives of KJ079 that eliminated all FRT sites. Primers and plasmids are listed in Table 1.

To remove the FRT site in the ΔadhE region, hybrid primers (WMadhEA/C) for ΔadhE::FRT target region were designed to contain approximately 50 by of homology to the 5' and 3' regions of ΔadhE::FRT site and 20 by corresponding to cat-sacB gene from pLOI4151. These primers were used for PCR amplification of the cat-sacB cassette using pLOI4151 as a template. The resulting PCR product was used to replace the FRT site in ΔadhE region with a cat-sacB cassette by a double-crossover, homologous recombination event with selection for resistance to chloramphenicol, to produce TG200.

The adhE gene and surrounding sequence were amplified from *E. coli* C using up/downadhE primers. The PCR product containing ychE'-adhE-ychG' (3.44 kb) was cloned into pCR2.1-TOPO, yielding pLOI4413. A second set of primers (IO-adhEup/down) was used to amplify the inside-out product with pLOI4413 as a template and Pfu polymerase to yield a blunt-ended product in which a 2.6 kb internal segment of adhE sequence was deleted. This inside-out PCR product was kinase-treated and self-ligated, resulting in pLOI4419. The PCR product amplified from pLOI4419 (up/downadhE primers) was used to replace the cat-sacB cassette in TG200 with the desired chromosomal sequence by another double, homologous recombination event, with sucrose selection for loss of sacB. The resulting strain was designated TG201 (KJ079 with the FRT removed from ΔadhE region).

The FRT sites in the ΔldhA and Δ(focA-pflB) regions were removed in a manner analogous to that used to delete the adhE::FRT site. Additional primer sets (ldhAA/C and IO-ldhAup/down) used to remove the FRT site in ΔldhA are included in Table 1 together with the corresponding plasmids (pLOI4430 and pLOI4432). Strain TG202 was produced by replacing this region in TG201 with the PCR product from pLOI4151 (WMldhAA/C primers). The cat-sacB cassette in TG202 was replaced with the PCR product from pLOI4432 (ldhAA/C primers) with sucrose selection for loss of sacB to produce TG203.

Primer sets (upfocA/MidpflA and IO-ycaOup/IO-midpflAdown) and corresponding plasmids (pLOI4415 and pLOI4421) used to remove the FRT site in Δ(focA-pflB) are included in Table 1. Strain TG204 was produced by replacing this region in TG203 with the PCR product from pLOI4151 (WMpflBA/C primers). The cat-sacB cassette in TG204 was replaced with the PCR product from pLOI4421 (upfocA/MidpflA primers) with sucrose selection for loss of sacB to produce KJ091. KJ091 is a derivative of KJ073 in which all FRT sites have been removed from the ΔadhE, ΔldhA and ΔfocA-pflB regions of the chromosome.

Construction of pLOI4162 Containing a cat-sacB Cassette for Markerless Gene Deletions To facilitate the sequential deletion of chromosomal DNA, plasmid pLOI4162 (FIG. 1) was constructed with a removable cat-sacB cassette and the option to include an 18-bp segment of synthetic DNA with stop codons in all reading frames. This plasmid is composed of synthetic sequences and parts of plasmids pLOI2228 (Martinez-Morales et al., 1999), pLOI2511 (Underwood et al., 2002), and pEL04 (Lee et al., 2001; Thomason et al., 2005). Using pEL04 as a template, inside-out PCR was performed with the JMpEL04F1/R1 primers to eliminate unwanted SmaI and BamHI sites between the cat and sacB genes. The amplified product was digested with BglII (within both primers) and self-ligated to produce pLOI4152. Plasmid pLOI4131 was constructed by ligation of the FRT-cat-FRT fragment (Klenow-treated BanI, ClaI) from pLOI2228 into compatible sites of pLOI2511 (Klenow-treated NheI, ClaI). Plasmid pLOI4131 was subsequently digested with EcoRI and self-ligated to remove the FRT-cat-FRT fragment to produce pLOI4145, retaining single KasI and XmaI sites. A polylinker segment (SfPBXPS) was prepared by annealing complementary oligonucleotides (SfPBXPSsense and StPBXPScomp). After digestion with KasI and XmaI, this segment was ligated into corresponding sites of pLOI4145 to produce pLOI4153. The modified cat-sacB cassette in pLOI4152 was amplified by PCR using the JMcatsacBup3/down3 primer set. After digestion with BamHI and XhoI, this cassette was ligated into corresponding sites of pLOI4153 to produce pLOI4146. To create an 18-bp region (5'GCCTAATTAATTAATCCC3') (SEQ ID NO: 1) with stop codons in all six reading frames, pLOI4146 was digested with PacI and self-ligated to produce pLOI4154 (not shown), removing the cat-sacB cassette. Two additional bases (T and A) were inserted between the SfoI and PacI sites of pLOI4154 using mutagenic primers (JM4161sense/comp) and linear plasmid amplification to produce pLOI4161. Finally, the PacI digested fragment from pLOI4146 containing the cat-sacB cassette was ligated into the PacI-digested site of pLOI4161 to produce pLOI4162 (GenBank accession EU531506).

Construction of Gene Deletions in tdcDE, and aspC

The tdcDE gene and neighboring 1000 by regions (tdcG'-tdcFED-tdcC', 5325 bp) were amplified using tdcDEup/down primers and cloned into the pCR2.1-TOPO vector to produce plasmid pLOI4515. A 1000-fold diluted preparation of this plasmid DNA served as a template for inside-out amplification using the tdcDEF7/R7 primers (both primers within the tdcDE gene and facing outward). The resulting 6861 by fragment containing the replicon was ligated to the amplified, SmaI/SfoI-digested cat-sacB cassette from pLOI4162 (JMcatsacBup3/down3 primers) to produce pLOI4516. This 6861 by fragment was also used to construct a second plasmid, pLOI4517 (kinase treated, self-ligation) containing a deletion of tcdD and tdcE. The PCR fragments amplified from pLOI4516 and pLOI4517 (tdcDEup/down primers) were used to replace tdcDE region in KJ091. The resulting clones were tested for loss of ampicillin and chloramphenicol resistance and designated KJ098.

The aspC gene was deleted from KJ104 in a manner analogous to that used to delete the tdcDE gene. Additional primer sets (aspCup/down and aspC1/2) used to construct the aspC deletion are included in Table 1 together with the corresponding plasmids (pLOI4280, pLOI4281, and pLOI4282). The resulting strain was designated KJ110. Neither KJ098, nor KJ110 contain any intervening sequence within the respective deleted regions (tdcDE and aspC).

Removal of FRT Site in ackA Region and Construction of citF, sfcA, and pta-ackA Gene Deletions To eliminate the FRT site in the ackA region of KJ073, plasmids containing sequences of the desired mutation were constructed as follows. E. coli C genomic DNA was used as the template for PCR amplification of ackA with the JMackAF1/R1 primers that bind approximately 200 by upstream and downstream of the ackA gene. The linear product was cloned into pCR23.1-TOPO (Invitrogen, Carlsbad, Calif.) to produce pLOI4158. Plasmid pLOI4158 was then used as a template for inside-out PCR with JMackAup1/down1 primers and Pfu polymerase to yield a blunt-ended product that lacks an 808-bp internal segment of ackA. The PacI-flanked cat-sacB cassette (SmaI/SfoI fragment from pLOI4162) was then ligated into the blunt PCR product to produce pLOI4159. Plasmid pLOI4159 served as a template for PCR amplification (JMackAF1/R1 primers). This PCR product was used to replace the FRT site in the ackA region of KJ073 by double-crossover homologous recombination, with selection for chroramphenicol resistance. The resulting clone was designated KJ076.

Plasmid pLOI4159 was also digested with PacI to remove the cat-sacB cassette and self-ligated to produce pLOI4160, retaining the 18-bp translational stop sequence. Plasmid pLOI4160 served as a PCR template (JMackAF1/R1 primers). This amplified fragment was used to replace the cat-sacB cassette in KJ076 by double-crossover homologous recombination with selection for loss of sacB. After removal of pKD46 by growth at elevated temperature, the resulting strain was designated KJ079. In this strain, the deleted region has been replaced by the 18-bp translational stop sequence.

The strategy used above to remove the FRT site from the ackA region was employed to make sequential deletions of citF, sfcA and pta-ackA and to replace the deleted regions with the 18-bp translational stop sequence. Additional primer sets (citFup/down and citF2/3) used to construct the citF deletion are included in Table 1 together with the corresponding plasmids (pLOI4629, pLOI4630, and pLOI4631). The resulting strain was designated KJ104.

The sfcA gene was deleted from strains KJ104 and KJ110, resulting in strains designated KJ119 and KJ122, respectively. Additional primer sets (sfcAup/down and sfcA1/2) used to construct the sfcA deletions are included in Table 1 together with the corresponding plasmids (pLOI4283, pLOI4284, and pLOI4285).

The ackA-pta operon (including the synthetic translational stop sequence) was deleted from KJ122 to produce strain KJ134. Additional primer sets (ackAup/ptadown and ackA21/pta2) used to construct this deletion are included in Table 1 together with the corresponding plasmids (pLOI4710, pLOI4711, and pLOI4712). Strain KJ134 does not contain any FRT sites or foreign genes.

Fermentations

Seed cultures and fermentations were incubated at 37° C. (100 rpm) in AM1 mineral salts medium (Martinez et al., 2007) containing 10% (w/v) glucose (555 mM), 100 mM $KHCO_3$, and 1 mM betaine HCl. A mixture of 3M $K_2CO_3$ and 6N KOH was added to maintain pH and supply $CO_2$. Differences in base composition (mixtures of 1:1, 4:1, 6:1) had little effect on fermentation. Fermentations were carried out in small vessels with a working volume of 350 ml. Fermentations were inoculated at an initial $OD_{550}$ of 0.01 (3.3 mg CDW $1^{-1}$) unless indicated otherwise. Fermentation vessels were sealed except for a 16-gauge needle that served as a vent and a port for sample removal. Anaerobiosis was rapidly achieved during growth. Added bicarbonate served to ensure an atmosphere of $CO_2$.

Analyses

Cell mass was estimated from the optical density at 550 nm (OD 1.0=333 mg of cell dry weight $l^{-1}$) by using a Bausch & Lomb Spectronic 70 spectrophotometer. Organic acids and sugars were determined by using high performance liquid chromatography (Grabar et al., 2006).

Results and Discussion

Construction of Markerless Strains for Succinate Production

Figure 9:
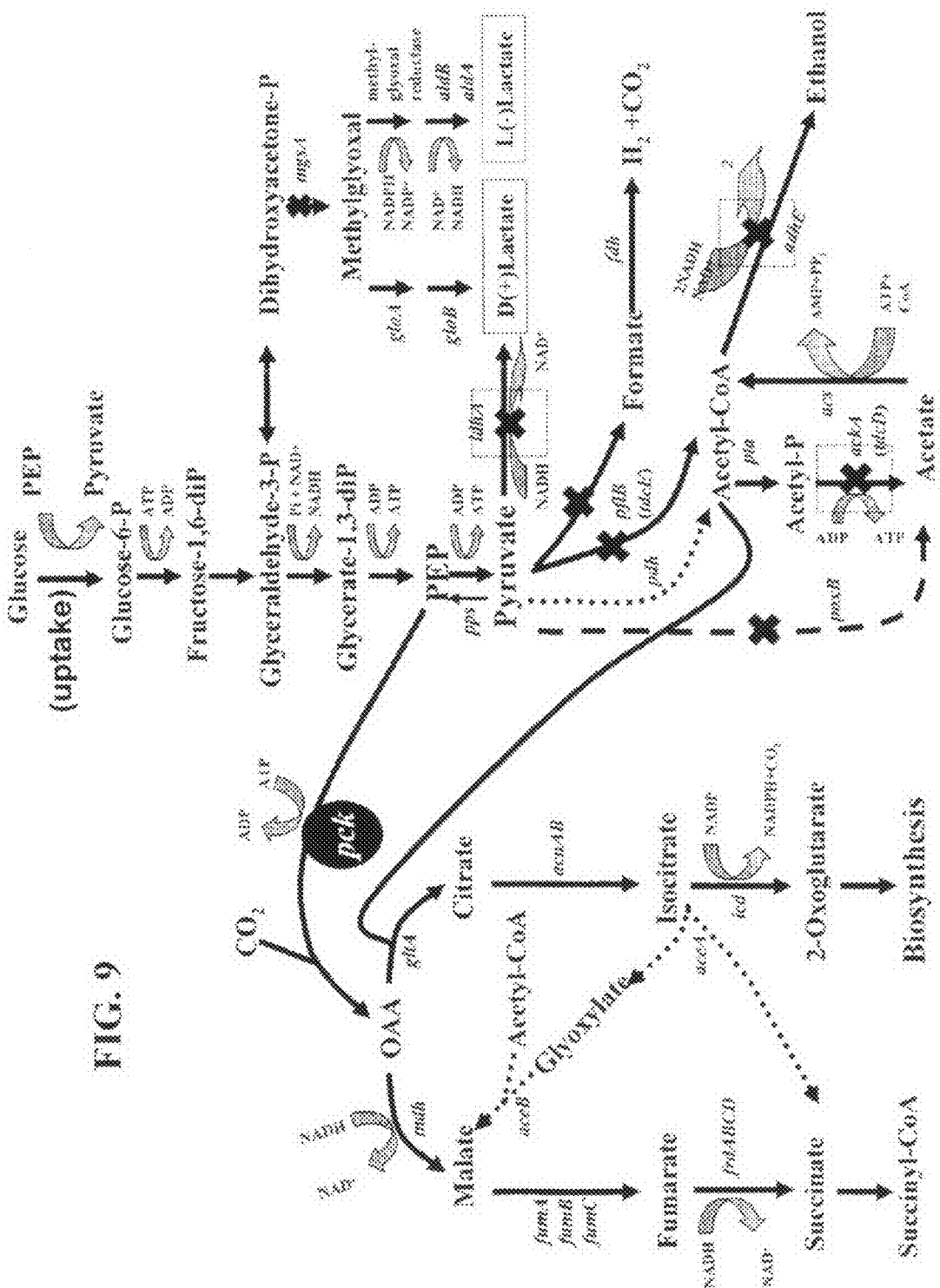
FIG. 9. Succinate production pathway in KJ073. The pck gene encoding phosphoenolpyruvate carboxykinase, the primary carboxylating enzyme involved in succinate production in this study, is shown in reverse type. Solid arrows indicate reactions expected to be functional during anaerobic fermentation of glucose. Solid crosses indicate deleted genes. Boxed crosses represent key deletions used to construct initial strain for succinate production, KJ017 (ldhA, adhE, ackA). The dashed line represents oxidation of pyruvate to acetate by PoxB, a process that is typically functional only under microaerophilic conditions. The dotted lines indicate reactions that are primarily associated with aerobic metabolism. Genes and enzymes: ldhA, lactate dehydrogenase; pflB, pyruvate-formate lyase; focA, formate transporter; pta, phosphate acetyltransferase; ackA, acetate kinase; adhE, alcohol dehydrogenase; ppc, phosphoenolpyruvate carboxylase; pdh, pyruvate dehydrogenase complex; gltA, citrate synthase; mdh, malate dehydrogenase; fumA, fumB, and fumC, fumarase isozymes; frdABCD, fumarate reductase; fdh, formate dehydrogenase; icd, isocitrate dehydrogenase; acs, acetyl-CoA synthetase; mgsA, methylglyoxal synthase; poxB, pyruvate oxidase; aldA, aldehyde dehydrogenase; and aldB, aldehyde dehydrogenase. The tdcE gene (pyruvate formate-lyase, homologous to pflB) and tcdD gene (propionate kinase, homologous to ackA) are shown in parenthesis and are typically expressed during threonine degradation.

The central anaerobic fermentation genes in *E. coli* C wild type were sequentially deleted by the strategy of Datsenko & Wanner (2000) with PCR products and removable antibiotic markers (by using FRT recognition sites and FLP recombinase). These constructions in combination with metabolic evolution (growth-based selection for increased efficiency of ATP production) were used to select for a mutant strain that recruited the energy-conserving, phosphoenylpyruvate carboxykinase (pck) to increase growth and succinate production (FIG. 9). The resulting strain, KJ073, produced 1.2 moles of succinate per mole of metabolized glucose (Jantama et al., 2008) and now uses a succinate pathway quite analogous to the rumen bacterium, *Actinobacillus succinogenes* (van der Werf et al., 1997) and *Mannheimia succiniciproducens* (Song et al., 2007). However, methods used to construct these gene deletions left a single 82- to 85-nt genetic scar or FRT site in the region of each deleted gene (ackA, ldhA, adhE, ackA, focA-pflB). These FRT sites served as recognition sites for FLP recombinase (Storici et al., 1999) during removal of the antibiotic genes. All of these extraneous sequences were sequentially removed from KJ073 and replaced with native DNA with only the desired gene deletion using methods that have been described previously (Grabar et al., 2006; Zhang et al., 2007; Jantama et al., 2008). The resulting strain, KJ091, contains specific deletions in ackA, ldhA, adhE, focA-pflB, ackA, mgsA, and poxB and lacks all FRT sites. This strain is devoid of all foreign and synthetic DNA except for an 18-bp translational stop sequence within ackA. Succinate production by strain KJ091 was equivalent to that of KJ073 (Table 7). This strain was used as the parent for further improvements in succinate production.

Reduction of Acetate During Succinate Production by Deletion of tdcD and tdcE

During the anaerobic fermentation of glucose by *E. coli*, pyruvate formate-lyase (pflB) serves as the primary source of acetyl~CoA, the precursor of acetyl~P, and acetate kinase (ackA) serves as the primary route for acetate production from acetyl~P (Karp et al. 2007; Kessler & Knappe, 1996). The abundance of acetate as a fermentation product in strains KJ073 and KJ091 was surprising since these strains contain deletions in both ackA and pflB (FIG. 9). This residual acetate at the end of fermentation represents a potential opportunity to further redirect metabolism for improved succinate yield.

Figure 10:
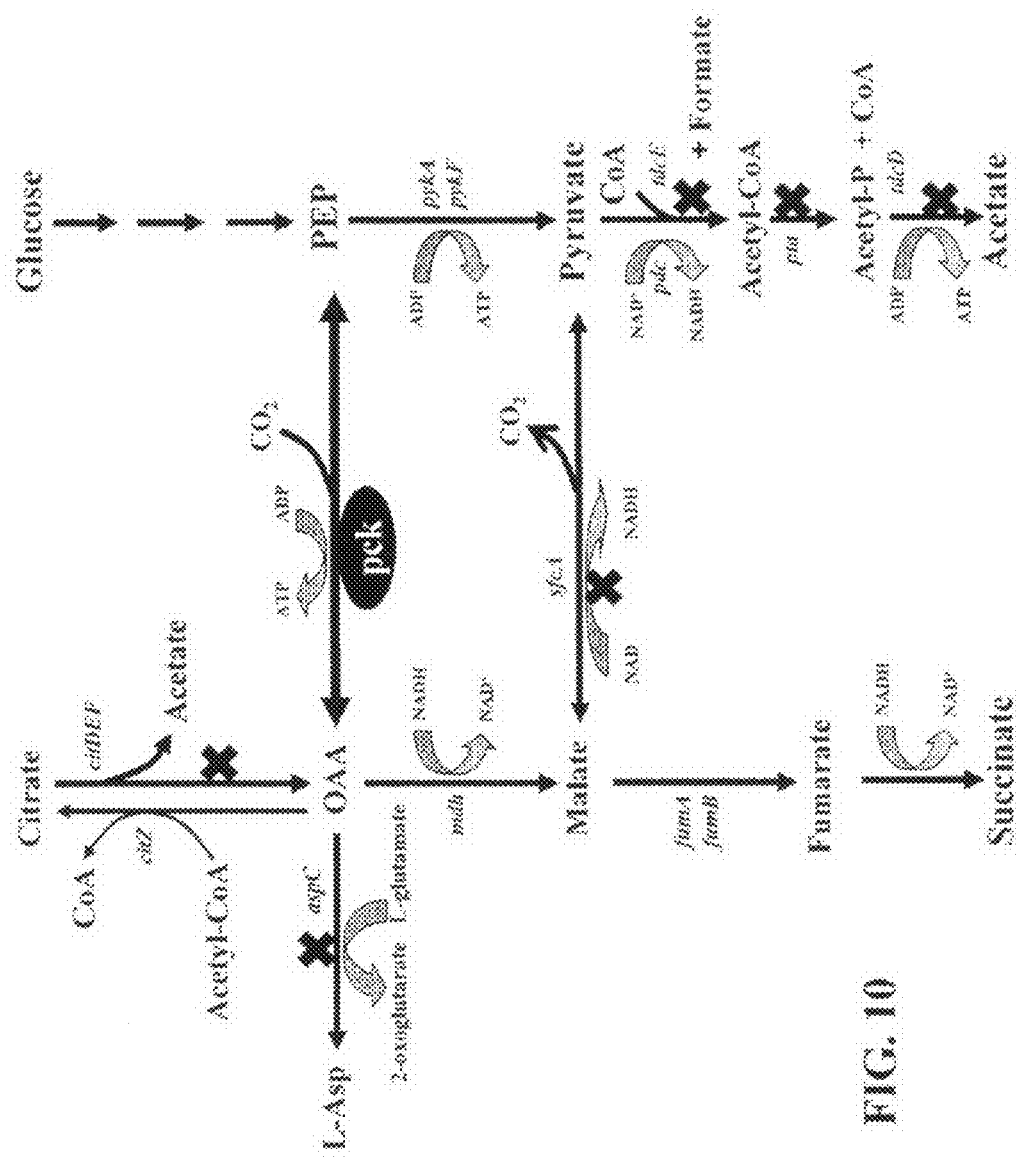
FIG. 10. Expanded portion of metabolism illustrating the pathways of additional genes that have been deleted (solid crosses). Succinate and acetate are principal products (boxed) from KJ073 fermentations. Genes and enzymes: citDEF, citrate lyase; gltA, citrate synthase; aspC, aspartate aminotransferase; pck, phosphoenolpyruvate carboxykinase; sfcA, NAD+-linked malic enzyme; fumA & fumB, fumarase; frdABCD, fumarate reductase; pykA & pykF, pyruvate kinase; tdcE, pyruvate formate-lyase (homologue pflB); pta, phosphate transacetylase; tcdD, acetate kinase (homologue of ackA).

A related enzyme with acetate kinase (and proprionate kinase) activity is encoded by tdcD but is typically produced only for the degradation of threonine (Hesslinger et al., 1998; Reed et al., 2003). It is possible that mutations occurring during selection have increased expression of tdcD as illustrated in FIG. 10. During anaerobic growth with 10% (w/v) glucose, expression of tdcD could functionally replace ackA, increasing the production of acetate from acetyl~P. The adjacent tdcE gene in the same operon is similar to pflB and encodes a pyruvate (and α-ketobutyrate) formatelyase activity that is co-expressed during threonine degradation (Hesslinger et al., 1998). It is possible that increased expression of this gene during anaerobic growth with 10% (w/v) glucose could increase the production of acetyl~CoA, the immediate precursor of acetyl~P, and waste reductant as formate (FIG. 10). Both tdcD and tdcE (adjacent) were simultaneously deleted from KJ091 to produce KJ098. Deletion of these two genes reduced acetate production by half and increased succinate yield by 10% in KJ098 in comparison to KJ091, establishing the importance of this unexpected pathway in diverting carbon flow away from succinate. Surprisingly, the production of malate by KJ091 was also eliminated as a result of the new deletions in KJ098. The level of pyruvate produced by KJ098 also declined by 40%, an intermediate that would be predicted to increase upon elimination of two alternative routes for pyruvate metabolism, pyruvate formate-lyase activity (tdcD) and acetate kinase activity (tdcE). The mechanisms responsible for the elimination of malate (a problem contaminant during succinate purification), the reduction in pyruvate, and the increase in succinate which resulted from the simultaneous deletion of tdcD and tdcE are unknown.

Effect of Citrate Lyase (citDEF) Deletion on Acetate Yield During Succinate Production Although KJ098 represents a significant improvement over KJ091, further reduction in acetate levels and further increases in succinate yields may be possible. Under anaerobic conditions, oxaloacetate is partitioned into the reduced product (malate) and oxidized intermediate (citrate) (FIG. 9). Citrate can be converted back to oxaloacetate and acetate by citrate lyase (citDEF) to recycle the intracellular OAA pool for other metabolic functions (Nilekani et al., 1983). Expression of significant amounts of citrate lyase is associated with growth on citrate (Lutgens and Gottschalk, 1980; Kulla and Gottschalk, 1977). Citrate lyase is a multi-enzyme complex made up of three different polypeptide chains. The α or large subunit is a citrate-ACP transferase that catalyzes the first step. The β or medium subunit is a citryl-ACP lyase that catalyzes the second step. The γ or small subunit acts as an acyl-carrier protein and also carries the prosthetic group components. All three subunits are required for the reaction to take place (Quentmeier et al., 1987). The deletion of genes encoding one or more of these subunits would eliminate citrate lyase activity and may further reduce the level of acetate during succinate production. The citF gene was deleted from KJ098 to produce KJ104. This deletion, however, had no effect on acetate production or other succinate yield (Table 7). Since deletion of citF did not cause any reduction in acetate, this intermediate is presumed to arise form other pathways. For unknown reasons, deletion of citF adversely affected the growth of KJ104 (reduced cell yield by 22%) and increased the level of pyruvate at the end of fermentation by almost 50% in comparison to KJ098. However, the succinate yield, titer, average productivity, and acetate levels with KJ104 were comparable to those with KJ098 (Table 7).

Effect of aspC and sfcA Deletions on Succinate Yield

Aspartate aminotransferase (aspC) is a multifunctional enzyme that catalyzes the synthesis of aspartate, phenylalanine and other compounds by transamination. In the reaction, L-aspartate is synthesized from oxaloacetate, an intermediate from PEP carboxylation, by a transamination reaction with L-glutamate. Aspartate is a constituent of proteins and participates in several other biosynthetic pathways. About 27 percent of the cellular nitrogen has been estimated to flow through aspartate (Reitzer, 2004). Aspartate biosynthesis and succinate production share a common intracellular pool of oxaloacetate. Deletion of aspC could lead to increased succinate production but may also create an auxotrophic requirements that prevent anaerobic growth in minimal salts medium such as AM1.

This aspartate aminotransferase gene (aspC) was deleted from KJ104 to produce KJ110. Unexpectedly, the deletion of aspC had no effect on succinate yield or cell yield in KJ110 as compared to KJ104 (Table 7). Thus aspartase does not appear to divert significant levels of oxaloacetate away from succinate production in our strain. Alternative enzymes appear to be available that replace the biosynthetic needs formerly catalysed by aspartate aminotransferase.

Significant amounts of pyruvate are present at the end of fermentation with KJ104 and other strains of *E. coli* engineered for succinate production (Table 7). This pyruvate represents an unwanted product and a further opportunity to increase succinate yield. This high level of pyruvate in fermentation broth could result from the decarboxylation of malate to pyruvate by malic enzyme (sfcA) as illustrated in FIG. 10. This enzyme is thought to function primarily during gluconeogenesis (Unden and Kleefeld, 2004; Stols and Donnelly, 1997; Oh et al., 2002) rather than during the anaerobic catabolism of glucose. Although reductive carboxylation of pyruvate to form malate is thermodynamically favored, the kinetic parameters of this enzyme favor the dehydrogenation and decarboxylation under physiological conditions (Stols and Donnelly, 1997). Over-expression of this enzyme to carboxylate pyruvate has been previously used as a basis to construct strains for succinate production of *E. coli* (Stols and Donnelly 1997).

If malic enzyme (sfcA) is carboxylating in KJ104 (and related strains) and contributing to succinate production, deletion of this gene would be expected to reduce succinate yields and increase the levels of other products such as pyruvate. Alternatively, if malic enzyme (scfA) is decarboxylating in KJ104 and diverting malate to pyruvate, deleting the gene encoding this enzyme would be expected to increase succinate yields and decrease the levels of pyruvate. Unexpectedly, deletion of the sfcA gene from KJ104 to produce KJ119 had no measurable effect on succinate production, growth, pyruvate levels, etc (Table 7) in comparison to KJ104. These results clearly demonstrated that malic enzyme (sfcA) is unimportant for succinate production in KJ104 and related strains. This result is in sharp contrast to the succinate-producing strains developed by Stols et al. (1997) in which increased production of malic enzyme was used as the primary route for succinate production.

Although no significant benefits were observed from either an sfcA deletion or an aspC deletion in KJ104, studies were carried out to test the effect of deleting both genes in combination. This was done by deleting the sfcA gene in KJ110 to produce KJ122 and expected to see no benefit. However, the combined deletion of both sfcA and aspC (strain KJ122) resulted in an unexpected increase in succinate yield and titer with a small reduction in acetate (Table 7), in comparison to the parent strain KJ110 and related strains (KJ104 and KJ119). The combined deletion (aspC and sfcA) in KJ122 resulted in significant increases in succinate yield, succinate titer, and average productivity of 18%, 24%, and 24%, respectively as compared to KJ104. Although the mechanism is unknown, it is possible that single mutations were ineffective because they were compensated in part by increased flow through the remaining activity, malic enzyme or aspartate aminotransferase (FIG. 10), dampening any potential benefit. The increase in succinate yield and titer are presumed to result from an increase in the availability of oxaloacetate allowing a larger fraction to proceed to succinate. Malate levels also remained extremely low.

Strain KJ122 (Table 7) produced 1.5 mol succinate per mole of glucose, 88% of the maximum theoretical yield (1.71 mol per mol glucose). To produce this high level of succinate and fully reduce malate, additional reductant was required. Although the source of this additional reductant is unknown, these results are consistent with an increase in pyruvate flow through pyruvate dehydrogenase. This enzyme is thought to function primarily during aerobic metabolism (Guest et al., 1989) but has also been reported to function at low levels during fermentation (de Graef et al., 1999).

Reduction in Pyruvate and Acetate by Deletion of pta

KJ122 produced excellent succinate yields (1.5 mol mol$^{-1}$ glucose) plus smaller amounts of acetate and pyruvate. The maximum theoretical yield for succinate is 1.71 mol mol$^{-1}$ glucose and these 3-carbon intermediates represent an opportunity to further increase yield. Pyruvate is presumed to accumulate from glycolysis as a metabolic overflow and may be related to acetate accumulation. Acetyl~CoA is an allosteric regulator of many enzymes. The source of acetate and acetate kinase activity is unknown since genes encoding the two primary activities for acetate kinase (tdcD and ackA) have been deleted (FIG. 9 and FIG. 10). Assuming that the acetate is produced from acetyl~P, the product of phosphotransacetylase, a further deletion was constructed in KJ122 to inactivate the pta gene. The resulting strain, KJ134, produced near theoretical level of succinate (Table 7). In this strain, pyruvate and acetate levels were substantially reduced. Volumetric productivity was also reduced by 17%. Succinate yields with strain KJ134 are equal or better than all other strains regardless of the complexity of fermentation processes, media, or growth conditions.

TABLE 1

Comparison of succinate production by microbial biocatalysts[a]

| Organism | Medium/Condition | Succinate Titer (mM)[b] | Succinate Yield (mol/mol) | Reference |
|---|---|---|---|---|
| *E. coli* KJ060 (ldhA adhE ackA focA pflB) | 100 g/l glucose AM1 with 10 g/l NaHCO$_3$, simple batch fermentation, 120 h incubation, pH maintained with 1:1 mixture of 6M KOH + 3M K$_2$CO$_3$ | 733 [0.90] | 1.41 | This paper |
| *E. coli* KJ073 (ldhA adhE ackA focA pflB mgsA poxB) | 100 g/l glucose AM1 with 10 g/l NaHCO$_3$, simple batch fermentation, 96 h incubation, pH maintained with 1:1 mixture of 6M KOH + 3M K$_2$CO$_3$ | 668 [0.82] | 1.20 | This paper |
| *E. coli* KJ060 (ldhA adhE ackA focA pflB) high inoculum (200 mg CDW l$^{-1}$) | 100 g/l glucose AM1 with 10 g/l NaHCO$_3$, simple batch fermentation, 120 h incubation, pH maintained with 1:1 mixture of 6M KOH + 3M K$_2$CO$_3$ | 622 [0.61] | 1.61 | This paper |
| *Actinobacillus succinogenes* FZ53 | 130 g/l glucose supplemented with 15 g/l CSL and 5 g/l YE, 80 g/l MgCO$_3$, anaerobic batch fermentation, 78 h incubation | 898 [1.36] | 1.25 | Guettler et al., 1996a |

TABLE 1-continued

Comparison of succinate production by microbial biocatalysts[a]

| Organism | Medium/Condition | Succinate Titer (mM)[b] | Succinate Yield (mol/mol) | Reference |
|---|---|---|---|---|
| *E. coli* AFP111 (pflAB, ldhA, ptsG) *Rhizobium etli* pyc overexpressed | 40 g/l glucose (90 g total glucose) in medium supplemented with 20 g/l tryptone, 10 g/l YE and 40 g/l MgCO$_3$, dual phase-fed batch fermentation, 76 h incubation | 841 [1.31] | 1.68 | Vemuri et al., 2002ab |
| *Anaerobiospirillum succiniciproducens* ATCC 53488 | 120 g/l glucose in peptone/YE based medium, integrated membrane-bioreactor-electrodialysis with CO$_2$ sparging, 150 h incubation | 703 [0.55] | 1.35 | Meynial-Salles et al., 2007 |
| *Actinobacillus succinogenes* 130Z | 100 g/l glucose supplemented with 15 g/l CSL and YE, 80 g/l MgCO$_3$, anaerobic batch fermentation, CO$_2$ sparging, 39 h incubation | 678 [2.05] | 1.37 | Guettler et al., 1996b |
| *E. coli* HL27659k/pKK313 (iclR sdhAB ackA-pta poxB, pstG) *Sorghum vulgare* pepc overexpressed | 106 g/l glucose in medium supplemented with 20 g/l tryptone, 32 g/l YE and 2 g/l NaHCO$_3$, fed batch fermentation under complete aerobic condition, 59 h incubation | 499 [1.00] | 0.85 | Lin et al., 2005d |
| *Anaerobiospirillum succiniciproducens* ATCC 53488 | 50 g/l glucose and 10 g/l CSL, CO$_2$ sparging and 300 mM Na$_2$CO$_3$, batch fermentation, 24 h incubation | 426 [2.09] | 1.37 | Glassner and Datta, 1992 |
| *Mannheimia succiniciproducens* (ldhA pflB pta-ackA) | 63 g/L glucose in MMH3 (yeast extract based medium), fed batch fermentation, 0.25 vol/vol/min CO$_2$ sparging, 30 h incubation | 444 [1.75] | 1.16 | Lee et al., 2006 |
| Bacterial Isolate 130Z ATCC 55618 | 50 g/l glucose supplemented with 1% CSL, 0.6% YE, and 2 g/l MgCO$_3$ neutralized with 10 N NaOH, 0.3 atm of CO$_2$, 29.5 h incubation | 388 [1.55] | 1.40 | Guettler et al., 1998 |
| *E. coli* SBS550MG (ldhA adhE iclR ackA-pta), *L. lactis* pyc *Bacillus subtilis* citZ | 20 g/l glucose (100 g total glucose) LB supplemented with 1 g/l NaHCO$_3$, 200 mg/l ampicillin, and 1 mM IPTG. 100% CO$_2$ at 1 L/min STP headspace, repeated fed-batch fermentation, 95 h incubation | 339 [0.42] | 1.61[c] | Sanchez et al., 2005a; Cox et al., 2006 |
| *E. coli* AFP184 (pflB ldhA pts) | 102 g/l glucose supplemented with 15 g/l CSL, dual phase aerobic growth and anaerobic production, sparging with air followed by CO$_2$, 32 h incubation | 339 [1.27] | 0.72[c] | Andersson et al., 2007 |
| *Actinobacillus succinogenes* ATCC 55618 | 70 g/l glucose with flour hydrolysate and 5 g/l YE, anaerobic batch fermentation with 4% inoculum, 65 h incubation | 302 [0.55] | 1.18 | Du et al., 2007 |
| *Anaerobiospirillum succiniciproducens* ATCC 53488 | 50 g/l glucose, 2% CSL, and 25 ppm tryptophan, neutralized with 5.5 M NaCO$_3$, saturated medium of 0.3 atm partial pressure of CO$_2$, 29.5 h incubation | 289 [1.16] | 1.04 | Guettler et al., 1998 |
| *Succinivibrio dextrinosolvens* ATCC 19716 | 15 g/l of each CSL and YE, 100 g/l glucose, and 80 g/l MgCO$_3$, batch fermentation, 36 h. | 226 [0.74] | NR | Guettler et al., 1998 |
| *Corynebacterium glutanicum* R | 40 g/l glucose (121 g total glucose) in Defined mineral salt medium with 400 mM NaHCO$_3$, fed batch fermentation, 6 h incubation | 195 [3.83] | 0.29 | Okino et al., 2005 |
| *Prevotella ruminocola* ATCC 19188 | 15 g/l of each CSL and YE, 100 g/l glucose, and 80 g/l MgCO$_3$, batch fermentation, 36 h incubation | 160 [0.52] | NR | Guettler et al., 1998 |
| *E. coli* SBS550MG (ldhA adhE iclR ackA-pta), *L. lactis* pyc *Bacillus subtilis* citZ | 20 g/l glucose LB supplemented with 1 g/l NaHCO$_3$, 200 mg/l ampicillin, and 1 mM IPTG. 100% CO$_2$ at 1 L/min STP headspace, batch fermentation, 24 h. incubation | 162.6 [0.80] | 1.61[c] | Sanchez et al., 2005a; Cox et al., 2006 |
| *Mannheimia succiniciproducens* MBEL55E KCTC 0769BP | 18 g/L glucose in MH4 (YE based medium) supplemented with 119 mM NaHCO$_3$, a continuous-cell-recycle membrane reactor with the CO$_2$ partial pressure of 101.3 kPa gas (100% CO$_2$), 6 h incubation | 144 [2.83] | 1.44 | Song et al., 2007 |

TABLE 1-continued

Comparison of succinate production by microbial biocatalysts[a]

| Organism | Medium/Condition | Succinate Titer (mM)[b] | Succinate Yield (mol/mol) | Reference |
|---|---|---|---|---|
| E. coli SBS110MG (ldhA adhE), Lactococcus lactis pyc | 20 g/l glucose LB supplemented with 1.5 g/l NaHCO$_3$ and 0.5 g MgCO$_3$, 200 mg/l ampicillin, and 1 mM IPTG. Dual phase with 100% CO$_2$ at 1 L/min STP headspace, 168 h incubation | 130 [0.09] | 1.24[c] | Sanchez et al., 2005a; Sanchez et al., 2006 |
| E. coli NZN111 (W1485 pflB ldhA), E. coli sfcA overexpressed | 20 g/l glucose LB supplemented with 0.5 g MgCO$_3$, 1.5 g/l NaOAc, 0.1 g/l ampicillin, and 10 μM IPTG, 44 h incubation, sealed serum tube. | 108 [0.22] | 0.98[c] | Stols et al., 1997 |
| E. coli JCL1208, E. coli ppc overexpressed | 11 g/l glucose LB supplemented with 0.15 g MgCO$_3$, 0.1 g/l carbenicillin, and 0.1 mM IPTG, 44 h incubation, anoxic CO$_2$ charging at 1 atm headspace, 18 h incubation | 91 [0.60] | 0.44[c] | Millard et al., 1996 |
| E. coli GJT-Sorghum pepC | 40 g/l glucose LB supplemented with 27.78 g/l MgCO$_3$, simple batch fermentation in sealed airtight flask | 80 [no data] | 0.42[c] | Lin et al., 2005c |
| E. coli HL51276k (iclR icd sdhAB ack4-pta poxB, pstG), Sorghum sp. pepC S8D mutation | 10.8 g/l glucose LB supplemented with 2 g/l NaHCO$_3$, 50 mg/l kanamycin, 1 mM IPTG, aerobic batch reactor, 50 h incubation | 68 [0.16] | 1.09[c] | Lin et al., 2005b |
| E. coli SBS880MG (ldhA adhE ΔfdhF), L. lactis pyc | 20 g/l glucose LB supplemented with 1.5 g/l NaHCO$_3$ and 0.5 g MgCO$_3$, 200 mg/l ampicillin, and 1 mM IPTG. Dual phase with 100% CO$_2$ headspace, 168 h incubation | 60 [0.04] | 0.94[c] | Sanchez et al., 2005b |

[a]Abbreviations: CSL, corn steep liquor; YE, yeast extract; NR, not reported.
[b]Average volumetric productivity is shown in brackets [g l$^{-1}$ h$^{-1}$] beneath succinate titer.
[c]The molar yield was calculated based on the production of succinate from metabolized sugar during both aerobic and anaerobic conditions. Biomass was generated predominantly during aerobic growth. Succinate was produced primarily during anaerobic incubation with CO$_2$, H$_2$, or a mixture of both.

TABLE 2

Escherichia coli strains, plasmids, and primers used in this study

| | Relevant Characteristics | Sources |
|---|---|---|
| *Escherichia coli* Strains | | |
| Strain C | Wild type (ATCC 8739) | ATCC |
| KJ012 | strain C, ΔldhA::FRT ΔadhE::FRT ΔackA::FRT | This study |
| KJ017 | KJ012, improved strain selected from 10% glucose, NBS | This study |
| KJ032 | KJ017, ΔldhA::FRT ΔadhE::FRT ΔackA::FRT Δ(focA-pflB)::FRT | This study |
| KJ060 | KJ032, improved strain selected from 10% glucose without initial acetate, NBS | This study |
| KJ070 | KJ060, ΔmgsA | This study |
| KJ071 | KJ070, improved strain selected from 10% glucose, NBS | This study |
| KJ072 | KJ071, ΔpoxB | This study |
| KJ073 | KJ072, improved strain selected from 10% glucose, AM1 | This study |
| SZ204 | Δ(focA-pflB)::FRT-kan-FRT | Zhou, 2003 |
| Plasmids | | |
| pKD4 | bla FRT-kan-FRT | Datsenko, 2000 |
| pKD46 | bla γ β exo (Red recombinase), temperature-conditional replicon | Datsenko, 2000 |
| pFT-A | bla flp temperature-conditional replicon and FLP recombinase | Posfai, 1997 |

TABLE 2-continued

*Escherichia coli* strains, plasmids, and primers used in this study

| | Relevant Characteristics | Sources |
|---|---|---|
| pEL04 | cat-sacB targeting cassette | Lee, 2001<br>Thomason, 2005 |
| pLOI3421 | 1.8 kbp SmaI fragment containing aac | Wood, 2005 |
| pLOI4151 | bla cat; cat-sacB cassette | This study |
| pCR2.1-TOPO | bla kan; TOPO TA cloning vector | Invitrogen |
| pLOI4228 | bla kan; ycc'-mgsA-helD' (PCR) from *E.coli* C cloned into pCR2.1-TOPO vector | This study |
| pLOI4229 | cat-sacB cassette PCR amplified from pLOI4151 (EcoRV digested) cloned into mgsA in pLOI4228 | This study |
| pLOI4230 | PCR fragment amplified from pLOI4228 (using mgsA-1/2 primers), kinase treated, then self-ligation | This study |
| pLOI4274 | bla kan; poxB (PCR) from *E.coli* C cloned into pCR2.1-TOPO vector | This study |
| pLOI4275 | cat-sacB cassette PCR amplified from pLOI4151 (EcoRV digested) cloned into poxB of pLOI4274 | This study |
| pLOI4276 | PCR fragment amplified from pLOI4274 (using poxB-1/2 primers), kinase treated, then self-ligation | This study |

Primer sets

| | | |
|---|---|---|
| ldhA | 5'ATGAACTCGCCGTTTTATAGCACAAAACAGTACG ACAAGAAGTACGTGTAGGCTGGAGCTGCTTC3'<br>(SEQ ID NO: 2)<br>5'TTAAACCAGTTCGTTCGGGCAGGTTTCGCCTTTT TCCAGATTGCTCATATGAATATCCTCCTTAG3'<br>(SEQ ID NO: 3) | This study |
| adhE | 5'ATGGCTGTTACTAATGTCGCTGAACTTAACGCAC TCGTAGAGCGTGTGTAGGCTGGAGCTGCTTC3'<br>(SEQ ID NO: 4)<br>5'TTAAGCGGATTTTTTCGCTTTTTTCTCAGCTTTAG CCGGAGCAGCCATATGAATATCCTCCTTAG3'<br>(SEQ ID NO: 5) | Zhou, 2003 |
| ackA | 5'ATGTCGAGTAAGTTAGTACTGGTTCTGAACTGCG GTAGTTCTTCAGTGTAGGCTGGAGCTGCTTC3'<br>(SEQ ID NO: 6)<br>5'TCAGGCAGTCAGGCGGCTCGCGTCTTGCGCGATA ACCAGTTCTTCCATATGAATATCCTCCTTAG3'<br>(SEQ ID NO: 7) | Zhou, 2003 |
| focA-pflB | 5'TTACTCCGTATTTGCATAAAAACCATGCGAGTTA CGGGGCCTATAAGTGTAGGCTGGAGCTGCTTC3'<br>(SEQ ID NO: 8)<br>5'ATAGATTGAGTGAAGGTACGAGTAATAACGTCCT GCTGCTGTTCTCATATGAATATCCTCCTTAG3'<br>(SEQ ID NO: 9) | This study |
| JMcatsacB | 5'TTAGCTAGCATGTGACCGAAGATCACTTCG3'<br>(SEQ ID NO: 10)<br>5'CCGCTAGCATCAAAGGGAAAACTGTCCATAT3'<br>(SEQ ID NO: 11) | This study |
| cat-up2/sacB-down2 | 5'AGAGAGGATATCTGTGACGGAAGATCACTTCG3'<br>(SEQ ID NO: 12)<br>5'AGAGAGGATATCGAATTGATCCGGTGGATGAC3'<br>(SEQ ID NO: 13) | This study |
| mgsA-up/down | 5'CAGCTCATCAACCAGGTCAA3'<br>(SEQ ID NO: 14)<br>5'AAAAGCCGTCACGTTATTGG3'<br>(SEQ ID NO: 15) | This study |

TABLE 2-continued

Escherichia coli strains, plasmids, and primers used in this study

| | Relevant Characteristics | Sources |
|---|---|---|
| mgsA-1/2 | 5'AGCGTTATCTCGCGGACCGT3' (SEQ ID NO: 16)<br>5'AAGTGCGAGTCGTCAGTTCC3' (SEQ ID NO: 17) | This study |
| poxB-up/down | 5'AAGCAATAACGTTCCGGTTG3' (SEQ ID NO: 18)<br>5'CCACTTTATCCAGCGGTAGC3' (SEQ ID NO: 19) | This study |
| poxB-1/2 | 5'GACGCGGTGATGAAGTGAT3' (SEQ ID NO: 20)<br>5'TTTGGCGATATAAGCTGCAA3' (SEQ ID NO: 21) | This study |
| pck-F/R | 5'TTGGCTAAGG AGCAGTGAAA TGCGCGTTA3' (SEQ ID NO: 22)<br>5'CACGACAAAA GAAGGGTAAA TAAAC3' (SEQ ID NO: 23) | This study |
| pck-2/3 | 5'TTGTTAACGCGCATTTCACT3' (SEQ ID NO: 24)<br>5'GCGATAGCGGCTACTGTCAT3' (SEQ ID NO: 25) | This study |
| pck (RT-PCR) | 5'GACGATACCACTCGCGAT3' (SEQ ID NO: 26)<br>5'GTCGACAACGAACAGACGT3' (SEQ ID NO: 27) | This study |
| birA (RT-PCR) | 5'ATCGTGATGGCGCAAGT3' (SEQ ID NO: 28)<br>5'CTTGCGATCCTGCAGATAG3' (SEQ ID NO: 29) | This study |

TABLE 3

Fermentation of glucose in mineral salts medium by mutant strains of E. coli

| Strain[a] | Culture Conditions | Media, Gluc (w/v) | Cell Yield[b] (g/L) | Succinate Yield[c] | | Av. Vol. Prod[d] (g/L/h) |
|---|---|---|---|---|---|---|
| | | | | mol/mol | g/g | |
| E. coli C wild type[f] | 0.1 OD$_{550}$, 0.1 mM 0.2 betaine | 5%, NBS | 2.0 ± 0.2 | 0.19 ± 0.02 | 0.12 | 0.12 ± 0.01 |
| KJ012[f] | 0.1 OD$_{550}$, 0.1 mM betaine | 5% NBS | 0.3 ± 0.1 | 0.20 ± 0.01 | 0.13 | 0.04 ± 0.01 |
| KJ012 | 0.1 OD$_{550}$, 0.1 mM betaine shaken flask[h] | 5% NBS + MOPS | 1.5 | 0.10 | 0.06 | 0.02 |
| KJ012 | 0.1 OD$_{550}$ Luria Broth | 5% LB | 1.5 | 0.70 | 0.50 | 0.09 |
| KJ012 (ldhA, ackA, adhE) (KJ017) | 1$^{st}$ TF: No betaine, 0.1 OD$_{550}$, 120 h transfers | 5%, NBS | 0.3 | 0.13 | 0.09 | 0.072 |
| | 3$^{rd}$ TF: 2 mM betaine, 0.1 OD$_{550}$, 96 h transfers | 5%, NBS | 0.7 | 0.28 | 0.18 | 0.128 |
| | 40$^{th}$ TF: 1 mM betaine, 0.1 OD$_{550}$, 24 h transfers, 3M K$_2$CO$_3$ + 6N KOH | 5%, NBS | 2.3 | 0.73 | 0.48 | 0.251 |
| | 40$^{th}$ TF: 1 mM betaine, 0.1 OD$_{550}$, 24 h transfers, 3M K$_2$CO$_3$ + 6N KOH | 10%, NBS | 1.7 | 0.74 | 0.49 | 0.354 |

TABLE 3-continued

Fermentation of glucose in mineral salts medium by mutant strains of *E. coli*

| | | | | | | |
|---|---|---|---|---|---|---|
| KJ032 (ldhA, ackA, adhE, focA, pflB) | $2^{nd}$ TF: 1 mM betaine, 0.1 OD$_{550}$, 48 h transfers, 20 mM NaOAc, 3M K$_2$CO$_3$ + 6N KOH | 5%, NBS | 1.0 | 1.47 | 0.97 | 0.260 |
| (KJ060) | $15^{th}$ TF: 1 mM betaine, 0.01 OD$_{550}$, 24 h transfers, 5 mM NaOAc, 3M K$_2$CO$_3$ + 6N KOH | 10%, NBS | 1.4 | 1.07 | 0.71 | 0.736 |
| | $5^{th}$ TF: 1 mM betaine, 0.01 OD$_{550}$, 24 h transfers, No NaOAc, 3M K$_2$CO$_3$ + 6N KOH | 10%, NBS | 1.4 | 1.04 | 0.69 | 0.711 |
| KJ070 (ldhA, ackA, adhE, focA, pflB, mgsA) | $1^{st}$ TF: 1 mM betaine, 0.01 OD$_{550}$, 24 h TF, 3M K$_2$CO$_3$ + 6N KOH, | 5%, NBS | 1.0 | 1.06 | 0.70 | 0.361 |
| (KJ071) | $50^{th}$ TF: 1 mM betaine, 0.01 OD$_{550}$, 24 h transfers, 3M K$_2$CO$_3$ + 6N KOH | 10%, NBS | 1.1 | 0.71 | 0.47 | 0.419 |
| KJ072 (ldhA, ackA, adhE, focA pflB, mgsA, puxB) | $2^{nd}$ TF: 1 mM betaine, 0.01 OD$_{550}$, 24 h transfers, 3M K$_2$CO$_3$ + 6N KOH | 10%, NBS | 1.3 | 0.97 | 0.64 | 0.663 |
| (KJ073) | $6^{th}$ TF: 1 mM betaine, 0.01 OD$_{550}$, 24 h transfers, 3M K$_2$CO$_3$ + 6N KOH | 10%, AM1 | 1.2 | 1.34 | 0.88 | 0.733 |
| | $45^{th}$ TF: 1 mM betaine, 0.01 OD$_{550}$, 24 h transfers, 3M K$_2$CO$_3$ + 6N KOH | 10%, AM1 | 1.5 | 1.26 | 0.83 | 0.858 |
| KJ073[f] | 1 mM betaine, 3M K$_2$CO$_3$ + 6N KOH 0.01 OD$_{550}$ inoculum | 10%, AM1 | 2.3 ± 0.1 | 1.20 ± 0.09 | 0.77 ± 0.03 | 0.82 ± 0.01 |
| KJ060[f] | 1 mM betaine, 3M K$_2$CO$_3$ + 6N KOH 0.01 OD$_{550}$ inoculum | 10%, AM1 | 2.2 ± 0.1 | 1.41 ± 0.07 | 0.92 ± 0.05 | 0.90 ± 0.04 |
| KJ060[f] | 1 mM betaine, 3M K$_2$CO$_3$ + 6N KOH 0.60 OD$_{550}$ inoculum | 10%, AM1 | 2.2 ± 0.1 | 1.61 ± 0.12 | 1.05 ± 0.09 | 0.77 ± 0.04 |
| KJ071[f] | 1 mM betaine, 3M K$_2$CO$_3$ + 6N KOH 0.01 OD$_{550}$ inoculum | 10%, NBS | 1.5 ± 0.0 | 0.78 ± 0.02 | 0.53 ± 0.01 | 0.33 ± 0.04 |

| | | Fermentation Products (mM)[e] | | | | | |
|---|---|---|---|---|---|---|---|
| Strain[a] | Culture Conditions | Suc | Mal | Pyr | Ace | Lac | For |
| *E. coli* C wild type[f] | 0.1 OD$_{550}$, 0.1 mM 0.2 betaine | 49 ± 3 | —[g] | 33 ± 10 | 152 ± 30 | 98 ± 24 | 262 ± 19 |
| KJ012 | 0.1 OD$_{550}$, 0.1 mM betaine | 6 ± 0.4 | — | — | 26 ± 1 | — | — |
| KJ012 | 0.1 OD$_{550}$, 0.1 mM betaine shaken flask[h] | 10 | — | — | 226 | — | 16 |
| KJ012 | 0.1 OD$_{550}$ Luria Broth | 108 | — | — | 61 | <2 | 14 |
| KJ012 (ldhA, ackA, adhE) (KJ017) | $1^{st}$ TF: No betaine, 0.1 OD$_{550}$, 120 h transfers | 6 | — | — | 26 | <2 | — |
| | $3^{rd}$ TF: 2 mM betaine, 0.1 OD$_{550}$, 96 h transfers | 26 | — | — | 71 | <2 | — |
| | $40^{th}$ TF: 1 mM betaine, 0.1 OD$_{550}$, 24 h transfers, 3M K$_2$CO$_3$ + 6N KOH | 204 | — | — | 179 | <2 | 151 |
| | $40^{th}$ TF: 1 mM betaine, 0.1 OD$_{550}$, 24 h transfers, 3M K$_2$CO$_3$ + 6N KOH | 288 | — | — | 181 | 38 | 199 |

TABLE 3-continued

Fermentation of glucose in mineral salts medium by mutant strains of E. coli

| | | | | | | | |
|---|---|---|---|---|---|---|---|
| KJ032 (ldhA, ackA, adhE, focA, pflB) | $2^{nd}$ TF: 1 mM betaine, 0.1 OD$_{550}$, 48 h transfers, 20 mM NaOAc, 3M K$_2$CO$_3$ + 6N KOH | 212 | — | — | 44 | — | — |
| (KJ060) | $15^{th}$ TF: 1 mM betaine, 0.01 OD$_{550}$, 24 h transfers, 5 mM NaOAc, 3M K$_2$CO$_3$ + 6N KOH | 596 | 331 | 9 | 170 | <2 | — |
| | $5^{th}$ TF: 1 mM betaine, 0.01 OD$_{550}$, 24 h transfers, No NaOAc, 3M K$_2$CO$_3$ + 6N KOH | 579 | 318 | 9 | 161 | <2 | — |
| KJ070 (ldhA, ackA, adhE, focA, pflB, mgsA) | $1^{st}$ TF: 1 mM betaine, 0.01 OD$_{550}$, 24 h TF, 3M K$_2$CO$_3$ + 6N KOH, | 294 | 219 | 25 | 102 | — | — |
| (KJ071) | $50^{th}$ TF: 1 mM betaine, 0.01 OD$_{550}$, 24 h transfers, 3M K$_2$CO$_3$ + 6N KOH | 341 | 626 | <2 | 76 | — | — |
| KJ072 (ldhA, ackA, adhE, focA pflB, mgsA, puxB) | $2^{nd}$ TF: 1 mM betaine, 0.01 OD$_{550}$, 24 h transfers, 3M K$_2$CO$_3$ + 6N KOH | 539 | 186 | <2 | 95 | — | — |
| (KJ073) | $6^{th}$ TF: 1 mM betaine, 0.01 OD$_{550}$, 24 h transfers, 3M K$_2$CO$_3$ + 6N KOH | 596 | 38 | 4 | 112 | — | — |
| | $45^{th}$ TF: 1 mM betaine, 0.01 OD$_{550}$, 24 h transfers, 3M K$_2$CO$_3$ + 6N KOH | 699 | 313 | 103 | 172 | — | — |
| KJ073$^f$ | 1 mM betaine, 3M K$_2$CO$_3$ + 6N KOH 0.01 OD$_{550}$ inoculum | 668 ± 8 | 118 ± 13 | 55 ± 22 | 183 ± 27 | — | — |
| KJ060$^f$ | 1 mM betaine, 3M K$_2$CO$_3$ + 6N KOH 0.01 OD$_{550}$ inoculum | 733 ± 39 | 39 ± 17 | — | 250 ± 36 | 2 ± 1 | — |
| KJ060$^f$ | 1 mM betaine, 3M K$_2$CO$_3$ + 6N KOH 0.60 OD$_{550}$ inoculum | 622 ± 8 | 17 ± 5 | 1.5 ± 1 | 180 ± 13 | 2 ± 1 | — |
| KJ071$^f$ | 1 mM betaine, 3M K$_2$CO$_3$ + 6N KOH 0.01 OD$_{550}$ inoculum | 280 ± 7 | 516 ± 14 | 58 ± 15 | 64 ± 9 | — | — |

$^a$Clones were isolated from the fermentation broth at various points and assigned strain numbers, indicated by numbers in parenthesis.
$^b$Cell yield estimated from optical density (3 OD$_{550\,nm}$ = 1 g l$^{-1}$ CDW).
$^c$Succinate yields were calculated based on glucose metabolized.
$^d$Average volumetric productivity was calculated for total incubation time.
$^e$Abbreviations: suc, succinate; mal, malate; pyr, pyruvate; ace, acetate; lac, lacate; for, formate.
$^f$Average of 3 or more fermentations with standard deviations.
$^g$Dash indicates absence of product.
$^h$Aerobic shaken flask (100 rpm; 100 ml NBS, 250-ml flask).

TABLE 4

Comparison of carboxylation enzyme activities in different strains

| | Specific activity [nmol min$^{-1}$ (mg protein)$^{-1}$] | | | | | |
|---|---|---|---|---|---|---|
| Enzyme | E. coli C | E. coli KJ012 | E. coli KJ017 | E. coli KJ073 | E. coli K12$^a$ | Actinobacillus succinogenes$^a$ |
| PEP carboxylase | 20 ± 2 | 25 ± 2 | 17 ± 1 | 27 ± 2 | 140 | 10 |
| PEP carboxykinase | 295 ± 23 | 162 ± 11 | 700 ± 68 | 7341 ± 462 | 140 | 4,700 |
| Malic enzyme (NADH, carboxylation) | ND$^b$ | 5 ± 2 | 12 ± 4 | 12 ± 3 | Unknown | Unknown |
| Malic enzyme (NADPH carboxylation) | <1 | <1 | <1 | <1 | Unknown | Unknown |

$^a$data was from van der Werf et al., 1997
$^b$Unable to measure in wild type E. coli C due to presence of lactate dehydrogenase.

TABLE 5

Composition of media (excluding carbon source).

| Component | Concentration (mmol L$^{-1}$) | |
|---|---|---|
| | $^a$NBS + 1 mM betaine | AM1 1 mM betaine |
| KH$_2$PO$_4$ | 25.72 | 0 |
| K$_2$HPO$_4$ | 28.71 | 0 |
| (NH$_4$)$_2$HPO$_4$ | 26.50 | 19.92 |
| NH$_4$H$_2$PO$_4$ | 0 | 7.56 |
| Total PO$_4$ | 80.93 | 27.48 |
| Total N | 53.01 | 47.39 |
| $^b$Total K | 84.13 | 1.00 |
| MgSO$_4$ 7H$_2$O | 1.00 | 1.50 |
| CaCl$_2$ 2H$_2$O | 0.10 | 0 |
| Thiamine HCl | 0.015 | 0 |
| Betaine-KCl | 1.00 | 1.00 |

TABLE 5-continued

Composition of media (excluding carbon source).

| Component | Concentration (mmol L$^{-1}$) | |
|---|---|---|
| | $^a$NBS + 1 mM betaine | AM1 1 mM betaine |
| | (μmol L$^{-1}$)$^c$ | |
| FeCl$_3$ 6H$_2$O | 5.92 | 8.88 |
| CoCl$_2$ 6H$_2$O | 0.84 | 1.26 |
| CuCl$_2$ 2H$_2$O | 0.59 | 0.88 |
| ZnCl$_2$ | 1.47 | 2.20 |
| Na$_2$MoO$_4$ 2H$_2$O | 0.83 | 1.24 |
| H$_3$BO$_3$ | 0.81 | 1.21 |
| MnCl$_2$ 4H$_2$O$_2$ | 0 | 2.50 |
| Total Salts | 12.5 g L$^{-1}$ | 4.1 g L$^{-1}$ |

$^a$NBS + 1 mM betaine: NBS media amended with betaine (1 mM).
$^b$Calculation includes KOH used to neutralize betaine-HCl stock.
$^c$Trace metal stock (1000X) was prepared in 120 mM HCl.

TABLE 6

Escherichia coli strains, plasmids, and primers used in herein

| | Relevant Characteristics | Sources |
|---|---|---|
| | *Escherichia coli* Strains | |
| Strain B | | |
| KJ073 | ΔldhA::FRT ΔadhE::FRT Δ(focA-pflB)::FRT ΔackA::FRT ΔmgsA ΔpoxB | Jantama et al., 2008 |
| KJ076 | KJ073, Δack4::cat-sacB, translational stop sequence | Disclosed herein |
| KJ079 | KJ073, Δack4::translational stop sequence | Disclosed herein |
| TG200 | KJ079, ΔadhE::cat-sacB | Disclosed herein |
| TG201 | TG200, ΔadhE | Disclosed herein |
| TG202 | TG201, ΔldhA::cat-sacB | Disclosed herein |
| TG203 | TG202, ΔldhA | Disclosed herein |
| TG204 | TG203, Δ(focA-pflB)::cat-sacB | Disclosed herein |
| KJ091 | TG204, Δ(focA-pflB) | Disclosed herein |
| KJ098 | KJ091, ΔtdcDE | Disclosed herein |
| KJ104 | KJ098, ΔcitF | Disclosed herein |
| KJ110 | KJ104, ΔaspC | Disclosed herein |
| KJ119 | KJ104, ΔsfcA | Disclosed herein |
| KJ122 | KJ110, ΔsfcA | Disclosed herein |
| KJ134 | KJ122. ΔackA-pta | Disclosed herein |

TABLE 6-continued

*Escherichia coli* strains, plasmids, and primers used in herein

| | Relevant Characteristics | Sources |
|---|---|---|
| | Plasmids | |
| pKD46 | Bla γ β exo (red recombinase), temperature-conditional replicon | Datsenko, 2000 |
| pEL04 | cat-sacB cassette | Lee, 2001 Thomason, 2005 |
| pLOI2228 | cat; FRT-cat-FRT cassette | Martinez-Morales et al., 1999 |
| pLOI2511 | bla kan; FRT-kan-FRT cassette | Underwood et al., 2002 |
| pLOI4131 | bla; ligation of pLOI2228 (BanI digested, Klenow treated, ClaI digested FRT-cat-FRT cassette) and pLOI2511 (NheI digested, Klenow treated, ClaI digested) | Disclosed herein |
| pLOI4145 | bla; EcoRI digested pLOI4131, self-ligation | Disclosed herein |
| pLOI4146 | bla cat; ligation of cat-sacB cassette PCR amplified (using JMcatsacBup3/down3 primers) from pLOI4152, BamHI/XhoI digested and BamHI/XhoI digested pLOI4153 | Disclosed herein |
| pLOI4151 | bla cat; cat-sacB cassette | Jantama et al., 2008 |
| pLOI4152 | cat-sacB cassette; PCR amplified cassette from pEL04 (using JMpEL04F1/R1 primers), BglII digestion and self-ligation | Disclosed herein |
| pLOI4153 | bla; ligation of pLOI4145 (KasI/XmaI digested) and KasI/XmaI digested SfPBXPS polylinker (annealing of complementary oligonucleotides SfPBXPSsense/SfPBX PScomp) | Disclosed herein |
| pLOI4154 | PacI digested pLOI4146, self ligation | Disclosed herein |
| pLOI4161 | bla cat; cat-sacB cassette | Disclosed herein |
| pLOI4162 | bla cat; ligation of cat-sacB cassette (PacI digested) from pLOI4146 and PacI digested pLOI4161 | Disclosed herein |
| pCR2.1-TOPO | bla kan; TOPO TA cloning vector | Invitrogen |
| pLOI4158 | bla kan; ackA (PCR) from *E.coli* C (using JMackA-F1/R1 primers) cloned into pCR2.1-TOPO vector | Disclosed herein |
| pLOI4159 | SmaI/SfoI digested cat-sacB cassette from pLOI4162 cloned into the PCR amplified inside-out product from pLOI4158 (using JMackAup1/down1) | Disclosed herein |
| pLOI4160 | PacI digestion of pLOI4159, then self-ligated | Disclosed herein |
| pLOI4515 | bla kan; tdcG'-tdcFED-tdcC' (PCR) from *E.coli* C (using tdcDE-up/down primers) cloned into pCR2.1-TOPO vector | Disclosed herein |
| pLOI4516 | SmaI/SfoI digested cat-sacB cassette from pLOI4162 cloned into the PCR amplified inside-out product from pLOI4515 (using tdcDE-F7/R7 primers) | Disclosed herein |
| pLOI4517 | PCR fragment amplified inside-out product from pLOI415 (using tdcDE-F7/R7 primers), kinase treated, then self-ligated | Disclosed herein |
| pLOI4629 | bla kan; citF (PCR) from *E.coli* C (using citF-up2/down2 primers) cloned into pCR2.1-TOPO vector | Disclosed herein |

TABLE 6-continued

*Escherichia coli* strains, plasmids, and primers used in herein

| | Relevant Characteristics | Sources |
|---|---|---|
| pLOI4630 | SmaI/SfoI digested cat-sacB cassette from pLOI4162 cloned into the PCR amplified inside-out product from pLOI4629 (using citF-2/3 primers) | Disclosed herein |
| pLOI4631 | PacI digestion of pLOI4630, then self-ligated | Disclosed herein |
| pLOI4280 | bla kan; aspC (PCR) from *E.coli* C (using aspC-up/down primers) cloned into pCR2.1-TOPO vector | Disclosed herein |
| pLOI4281 | SmaI/SfoI digested cat-sacB cassette from pLOI4162 cloned into the PCR amplified inside-out product from pLOI4280 (using aspC-1/2 primers) | Disclosed herein |
| pLOI4282 | PCR fragment amplified inside-out product from pLOI4280 (using aspC-1/2 primers), kinase treated, then self-ligated | Disclosed herein |
| pLOI4283 | bla kan; sfcA (PCR) from *E.coli* C (using sfrA-up/down primers) cloned into pCR2.1-TOPO vector | Disclosed herein |
| pLOI4284 | SmaI/SfoI digested cat-sacB cassette from pLOI4162 cloned into the PCR amplified inside-out product from pLOI4283 (using sfcA-1/2 primers) | Disclosed herein |
| pLOI4285 | PacI digestion of pLOI4284, then self-ligated | Disclosed herein |
| pLOI4710 | bla kan; ackA-pta (PCR) from *E.coli* C (using ackA-up/pta-down primers) cloned into pCR2.1-TOPO vector | Disclosed herein |
| pLOI4711 | SmaI/SfoI digested cat-sacB cassette from pLOI4162 cloned into the PCR amplified inside-out product from pLOI4710 (using ack4-2/pta-2 primers) | Disclosed herein |
| pLOI4712 | PacI digestion of pLOI4711, then self-ligated | Disclosed herein |
| pLOI4413 | bla kan; ychE'-adhE-ychG' (PCR) from *E.coli* C (using up/down-adhE primers) cloned into pCR2.1-TOPO vector | Disclosed herein |
| pLOI4419 | PCR fragment amplified inside-out product from pLOI4413 (IO-adhE-up/down using primers), kinase treated, then self-ligated | Disclosed herein |
| pLOI4415 | bla kan; ycaO '-focA-pflB-pflA' (PCR) from *E.coli* C (using up-focA/Mid-pflA primers) cloned into pCR2.1-TOPO vector | Disclosed herein |
| pLOI4421 | PCR fragment amplified inside-out product from pLOI4415 (using IO-ycaO-up/IO-midpflB-down primers), kinase treated, then self-ligated | Disclosed herein |
| pLOI4430 | bla kan; hslJ'-ldhA-ydbH' (PCR) from *E.coli* C (using ldhA-A/C primers) cloned into pCR2.1-TOPO vector | Disclosed herein |
| pLOI4432 | PCR fragment amplified inside-out product from pLOI4424 (using IO-ldk4-up/down primers), kinase treated, then self-ligated | Disclosed herein |

Primer sets

| | | |
|---|---|---|
| JM4161 sense/ comp | 5'ACCGCATCAGGCGCCTAATTAATTAATCCCGG3' (SEQ ID NO: 30) 5'CCGGGATTAATTAATTAGGCGCCTGATGCGGT3' (SEQ ID NO: 31) | Disclosed herein |
| JMpEL04F 1/R1 | 5'CAGCAGATCTAAGTAAATCGCGCGGGTTTG3' (SEQ ID NO: 32) 5'CAGCAGATCTAGCGGCTATTTAACGACCCT3' (SEQ ID NO: 33) | Disclosed herein |
| JMackA- F1/R1 | 5'GCCTGAAGGCCTAAGTAGTA3' (SEQ ID NO: 34) 5'GCACGATAGTCGTAGTCTGA3' (SEQ ID NO: 35) | Disclosed herein |

TABLE 6-continued

Escherichia coli strains, plasmids, and primers used in herein

| | Relevant Characteristics | Sources |
|---|---|---|
| JmackA up1/down1 | 5'GTTGAGCGCTTCGCTGTGAG3' (SEQ ID NO: 36) 5'GCCGCAATGGTTCGTGAACT3' (SEQ ID NO: 37) | Disclosed herein |
| JmcatsacB up3/down3 | 5'CTCACCTCGAGTGTGACGGAAGATCACTTCG3' (SEQ ID NO: 38) 5'GTGCAGGATCCATCAAAGGGAAAACTGTCCATAT3' (SEQ ID NO: 39) | Disclosed herein |
| SfPBXPS sense/comp | 5'ATGTAGGCGCCATTAATTAATGGATCCACTATCTCGAGATTAATTAATCCCGGGACTAT3' (SEQ ID NO: 40) 5'ATAGTCCCGGGATTAATTAATCTCGAGATAGTGGATCCATTAATTAATGGCGCCTACAT3' (SEQ ID NO: 41) | Disclosed herein |
| WMadhE A/C | 5'ATGGCTGTTACTAATGTCGCTGAACTTAACGCACTCGTAGAGCGTCGGCACGTAAGAGGTTCCAA3' (SEQ ID NO: 42) 5'TTAAGCGGATTTTTTCGCTTTTTTCTCAGCTTTAGCCGGAGCAGCACACTGCTTCCGGTAGTCAA3' (SEQ ID NO: 43) | Disclosed herein |
| WMldhA A/C | 5'ATGAAACTCGCCGTTTATAGCACAAAACAGTACGACAAGAAGTACGGCACGTAAGAGGTTCCAA3' (SEQ ID NO: 44) 5'TTAAACCAGTTCGTTCGGGCAGGTTTCGCCTTTTTCCAGATTGCTACACTGCTTCCGGTAGTCAA3' (SEQ ID NO: 45) | Disclosed herein |
| WMpflB A/C | 5'TTACTCCGTATTTGCATAAAAACCATGCGAGTTACGGGCCTATAACGGCACGTAAGAGGTTCCAA3' (SEQ ID NO: 46) 5'TTACATAGATTGAGTGAAGGTACGAGTAATAACGTCCTGCTGCTGTTCTACACTGCTTCCGGTAGTCAA3' (SEQ ID NO: 47) | Disclosed herein |
| tdcDE-up/down | 5'CGCCGACAGAGTAATAGGTT3' (SEQ ID NO: 48) 5'TGATGAGCTACCTGGTATGG3' (SEQ ID NO: 49) | Disclosed herein |
| tdcDE-F7/R7 | 5'CGATGCGGTGGCCAATTAAG3' (SEQ ID NO: 50) 5'GACGACGTGCTGGATTACGA3' (SEQ ID NO: 51) | Disclosed herein |
| citF-up2/down2 | 5'GGGTATTCAGGCGTTCGATA3' (SEQ ID NO: 52) 5'GCCCGAGAGGATGACTATGT3' (SEQ ID NO: 53) | Disclosed herein |
| citF-2/3 | 5'GGTGATCGATGTTGTGCATC3' (SEQ ID NO: 54) 5'CCCGTTCTTGTCGTTGAGAT3' (SEQ ID NO: 55) | Disclosed herein |
| IO-adhE-up/down | 5'GCTGCTCCGGCTAAAGCTGA3' (SEQ ID NO: 56) 5'ACGCTCTACGAGTGCGTTAA3' (SEQ ID NO: 57) | Disclosed herein |
| up-focA/Mid-pflB | 5'AGATCGCCAGCCGCTGCAAT3' (SEQ ID NO: 58) 5'AACCGTTGGTGTCCAGACAG3' (SEQ ID NO: 59) | Disclosed herein |
| IO-ycaO-up/IO-midpflB-down | 5'GCCTACATTGCGTAGGCTAT3' (SEQ ID NO: 60) 5'GCAGCAGGACGTTATTACTC3' (SEQ ID NO: 61) | Disclosed herein |

TABLE 6-continued

Escherichia coli strains, plasmids, and primers used in herein

| | Relevant Characteristics | Sources |
|---|---|---|
| ldhA-A/C | 5'ATGAAACTCGCCGTTTATAG3'<br>(SEQ ID NO: 62)<br>5'TTAAACCAGTTCGTTGCCC3'<br>(SEQ ID NO: 63) | Disclosed herein |
| IO-ldhA-up/down | 5'CGTTCGATCCGTATCCAAGT3'<br>(SEQ ID NO: 64)<br>5'AGGCTGGAACTCGGACTACT3'<br>(SEQ ID NO: 65) | Disclosed herein |
| aspC-up/down | 5'TCCATCGCTTACACCAAATC3'<br>(SEQ ID NO: 66)<br>5'TGGGGATGACGTGATATTT3'<br>(SEQ ID NO: 67) | Disclosed herein |
| aspC-1/2 | 5'AGATAACATGGCTCCGCTGT3'<br>(SEQ ID NO: 68)<br>5'AGGAGCGGCGGTAATGTTC3'<br>(SEQ ID NO: 69) | Disclosed herein |
| sfcA-up/down | 5'CTATGCTTGATCGGCAACCT3'<br>(SEQ ID NO: 70)<br>5'ACGATCGCCTGGTTTTAATG3'<br>(SEQ ID NO: 71) | Disclosed herein |
| sfcA-1/2 | 5'TACCGCCGTACCTCCATCTA3'<br>(SEQ ID NO: 72)<br>5'CGTAAGGGATATAAAGCAACG3'<br>(SEQ ID NO: 73) | Disclosed herein |
| ackA-up/pta-down | 5'CGGGACAACGTTCAAAACAT3'<br>(SEQ ID NO: 74)<br>5'ATTGCCCATCTTCTTGTTGG3'<br>(SEQ ID NO: 75) | Disclosed herein |
| ackA-2/pta-2 | 5'AACTACCGCAGTTCAGAACCA3'<br>(SEQ ID NO: 76)<br>5'TCTGAACACCGGTAACACCA3'<br>(SEQ ID NO: 77) | Disclosed herein |

TABLE 7

Fermentation of glucose in mineral salts AM1 medium by mutant strains of E. coli

| Strain | Culture Conditions | Media, Gluc (w/v) | Cell Yield$^a$ (g/L) | Succinate Yield$^b$ | | Av. Vol. Prod$^c$ (g/L/h) |
|---|---|---|---|---|---|---|
| | | | | mol/mol | g/g | |
| KJ073 | 1 mM betaine,<br>3M $K_2CO_3$ + 6N KOH (1:1)<br>0.01 $OD_{550}$ inoculum | 10%,<br>AM1 | 2.3 ± 0.1 | 1.20 ± 0.09 | 0.77 ± 0.03 | 0.82 ± 0.01 |
| KJ091 | 1 mM betaine,<br>3M $K_2CO_3$ + 6N KOH (1:1)<br>0.01 $OD_{550}$ inoculum | 10%,<br>AM1 | 2.2 ± 0.1 | 1.19 ± 0.02 | 0.78 ± 0.01 | 0.84 ± 0.01 |
| KJ098 | 1 mM betaine,<br>3M $K_2CO_3$ + 6N KOH (1:1)<br>0.01 $OD_{550}$ inoculum | 10%,<br>AM1 | 2.3 ± 0.1 | 1.30 ± 0.04 | 0.85 ± 0.02 | 0.79 ± 0.01 |
| KJ104 | 1 mM betaine,<br>3M $K_2CO_3$ + 6N KOH (4:1)<br>0.01 $OD_{550}$ inoculum | 10%,<br>AM1 | 1.8 ± 0.1 | 1.31 ± 0.01 | 0.86 ± 0.01 | 0.78 ± 0.03 |
| KJ104 | 1 mM betaine,<br>3M $K_2CO_3$ + 6N KOH (6:1)<br>0.01 $OD_{550}$ inoculum | 10%,<br>AM1 | 1.9 ± 0.1 | 1.30 ± 0.01 | 0.85 ± 0.01 | 0.77 ± 0.01 |
| KJ110 | 1 mM betaine,<br>3M $K_2CO_3$ + 6N KOH (4:1)<br>0.01 $OD_{550}$ inoculum | 10%,<br>AM1 | 2.0 ± 0.1 | 1.28 ± 0.02 | 0.84 ± 0.01 | 0.79 ± 0.01 |
| KJ119 | 1 mM betaine,<br>3M $K_2CO_3$ + 6N KOH (4:1)<br>0.01 $OD_{550}$ inoculum | 10%,<br>AM1 | 2.0 ± 0.1 | 1.33 ± 0.07 | 0.87 ± 0.01 | 0.82 ± 0.01 |
| KJ122 | 1 mM betaine,<br>3M $K_2CO_3$ + 6N KOH (4:1)<br>0.01 $OD_{550}$ inoculum | 10%,<br>AM1 | 2.3 ± 0.1 | 1.50 ± 0.02 | 0.98 ± 0.01 | 0.92 ± 0.01 |

TABLE 7-continued

Fermentation of glucose in mineral salts AM1 medium by mutant strains of E. coli

| | | | | | | | |
|---|---|---|---|---|---|---|---|
| KJ122 | 1 mM betaine, 3M $K_2CO_3$ + 6N KOH (6:1) 0.01 $OD_{550}$ inoculum | 10%, AM1 | 2.0 ± 0.2 | 1.54 ± 0.02 | 1.01 ± 0.01 | 0.97 ± 0.04 | |
| KJ122 | 1 mM betaine, 3M $K_2CO_3$ + 6N KOH (6:1) 0.15 $OD_{550}$ inoculum | 10%, AM1 | 2.1 ± 0.1 | 1.57 ± 0.09 | 1.03 ± 0.06 | 0.93 ± 0.06 | |
| KJ134 | 1 mM betaine, 3M $K_2CO_3$ + 6N KOH (6:1) 0.01 $OD_{550}$ inoculum | 10%, AM1 | 2.3 ± 0.1 | 1.70[g] ± 0.03 | 1.11 ± 0.02 | 0.83 ± 0.02 | |

| | Fermentation Products (mM)[d,e,f] | | | | | |
|---|---|---|---|---|---|---|
| Strain | Suc | Mal | Pyr | Ace | Lac | For |
| KJ073 | 668 ± 8 | 118 ± 13 | 55 ± 22 | 183 ± 27 | — | — |
| KJ091 | 687 ± 3 | 109 ± 3 | 72 ± 5 | 155 ± 6 | — | — |
| KJ098 | 644 ± 9 | — | 42 ± 8 | 88 ± 1 | — | — |
| KJ104 | 634 ± 25 | 5 ± 1 | 78 ± 5 | 90 ± 10 | — | — |
| KJ104 | 625 ± 4 | 3 ± 2 | 94 ± 5 | 81 ± 2 | — | — |
| KJ110 | 640 ± 10 | 4 ± 1 | 76 ± 6 | 106 ± 11 | — | — |
| KJ119 | 672 ± 10 | 4 ± 0 | 64 ± 18 | 95 ± 14 | — | — |
| KJ122 | 750 ± 1 | 0 ± 0 | 122 ± 21 | 94 ± 13 | — | — |
| KJ122 | 787 ± 35 | 6 ± 3 | 59 ± 6 | 110 ± 7 | — | — |
| KJ122 | 756 ± 49 | 0 ± 0 | 124 ± 13 | 122 ± 9 | — | — |
| KJ134 | 674 ± 15 | 13 ± 5 | 22 ± 9 | 37 ± 5 | — | — |

[a]Cell yield estimated from optical density (3 $OD_{550\,nm}$ = 1 g $l^{-1}$ CDW).
[b]Succinate yields were calculated based on glucose metabolized.
[c]Average volumetric productivity was calculated for total incubation time.
[d]Abbreviations: suc, succinate; mal, malate; pyr, pyruvate; ace, acetate; lac, lacate; for, formate.
[e]Ethanol (153 ± 39 mM) was present only in broth from E. coli C.
[f]All data represent an average of 3 or more fermentations with standard deviations.
[g]Additional products were also found despite near theoretical yields of succinate. Based on total products, coproducts represented 11%.

REFERENCES

U.S. Pat. No. 5,723,322
U.S. Pat. No. 5,869,301
U.S. Pat. No. 5,143,834, Glassner et al., 1992
U.S. Pat. No. 5,723,322, Guettler et al., 1998
U.S. Pat. No. 5,573,931, Guettler et al., 1996a
U.S. Pat. No. 5,505,004, Guettler et al., 1996b
Ajl, S. J., Werkman, C. H. (1948) "Enzymatic fixation of carbon dioxide in α-ketoglutaric acid" Proc. Natl. Acad. Sci. USA 34:491-498.
Andersson, C., Hodge, D., Berglund, K. A., Rova, U. (2007) "Effect of different carbon sources on the production of succinic acid using metabolically engineered Escherichia coli." Biotechnol Prog 23(2):381-388.
Asghari, A., Bothast, R. J., Doran, J. B., Ingram, L. O. (1996) "Ethanol production from hemicellulose hydrolysates of agricultural residues using genetically engineered Escherichia coli strain KO11" J. Industrial Microbiol. 16:42-47.
Causey, T. B., Shanmugan, K. T., Yomano, L. P, Ingram, L. O. (2004) "Engineering Escherichia coli for efficient conversion of glucose to pyruvate" Proc. Natl. Acad. Sci. USA 101:2235-2240.
Chao, Y and Liao, J. C. (1993) "Alteration of growth yield by overexpression of phosphoenol pyruvate carboxylase and phosphoenolpyruvate carboxykinase in Escherichia coli" Appl Environ Microbiol. 59:4261-4265.
Chang, Y.Y., Cronan, J. E., Jr. (2000) "Conversion of Escherichia coli pyruvate decarboxylase to an 'alpha-ketobutyrate oxidase'" Biochem. J. 352:717-724.
Chatterjee, R., Cynthia, S. M., Kathleen, C., David, P. C., Donnelly, M. I. (2001) "Mutation of the ptsG gene results in increased production of succinate in fermentation of glucose by Escherichia coli." Appl. Environ. Microbiol. 67:148-154.
Cox, S. J., Levanon, S. S., Sanchez, A. M., Lin, H., Peercy, B., Bennett, G. N., San, K. Y. (2006) "Development of a metabolic network design and optimization framework incorporating implement constraints: A succinate production case study" Metab. Engin. 8:46-57.
Datsenko, K. A., Wanner, B. L. (2000) "One-step inactivation of chromosomal genes in Escherichia coli K-12 using PCR products" Proc. Natl. Acad. Sci. USA 97:6640-6645.
de Graef, M. R., Alexeeva, S., Snoep, J. L., de Mattos, M. J. T. (1999) "The steady-state internal redox state (NADH/NAD) reflects the external redox state and is correlated with catabolic adaptation in Escherichia coli." J. Bacteriol. 181:2351-235.
Delbacre, L. T. J., Sudom, A. M., Prasad, L., Leduc, Y., Goldie, H. (2004) "Structure/function studies of phosphoryl transfer by phosphoenolpyruvate carboxykinase" Biochimica et Biophysica Acta. 1679:271-278.
Du, C., Lin, S. K., Koutinas, A., Wang, R., Webb, C. (2007) "Succinic acid production from wheat using a biorefining strategy" Appl Microbiol Biotechnol. 76(6):1263-1270.
Egyud, L. G., Szent-Gyorgyi, A. (1966) "On the regulation of cell division" Proc. Natl. Acad. Sci. USA 56:203-207.
Farmer, W. and Liao, J. C. (1997) "Reduction of aerobic acetate production by Escherichia coli" Appl. Environ. Microbiol. 63:3205-3210.
Fraenkel, D. G. (1996) Chapter 14, Glycolysis. In A. Böck, R. Curtiss III, J. B. Kaper, F. C. Neidhardt, T. Nyström, K. E. Rudd, and C. L. Squires (ed.), EcoSal—Escherichia coli and Salmonella: cellular and molecular biology. [Online.] http://www.ecosal.org. ASM Press, Washington, D.C.
Gokarn, R. R., Eiteman, M. A., Altman, E. (2000) "Metabolic analysis of Escherichia coli in the presence and absence of carboxylating enzymes phosphoenolpyruvate carboxylase and pyruvate carboxylase" Appl. Environ. Microbiol. 66:1844-1850.

Goldie, A. H. and Sanwal, B. D. (1980a) "Genetic and physiological characterization or *Escherichia coli* mutants deficient in phosphoenolpyruvate carboxykinase activity" *J Bacteriol,* 141(3):1115-1121.

Goldie, A. N. and Sanwal, B. D. (1980b) "Allosteric control by calcium and mechanism of desensitization of phosphoenolpyruvate carboxykinase of *Escherichia coli.*" *J Biol Chem.* 255(4):1399-1405.

Gottschalk, G. (1985) Bacterial metabolism. 2nd ed. Springer-Verlag, New York.

Grabar, T. B., Zhou, S., Shanmugam, K. T., Yomano, L. P., Ingram, L. O. (2006) "Methylglyoxal bypass identified as source of chiral contamination in L(+) and D(−) lactate fermentations by recombinant *Escherichia coli.*" *Biotechnol. Lett.* 28:1527-1535.

Guest, J. R., Angier, S. J., Russell (1989) "Structure, expression, and protein engineering in the pyruvate dehydrogenase complex of *Escherichia coli.*" *Ann. N.Y. Acad. Sci.* 573:76-99.

Hesslinger, C., Fairhurst, S. A., Sawers, G. (1998) "Novel keto acid formate-lyase and propionate kinase enzymes are components of an anaerobic pathway in *Escherichia coli* that degrades L threonine to propionate" *Mol Microbiol* 27(2):477-492.

Hopper, D. J., Cooper, R. A. (1971) "The regulation of *Escherichia coli* methylglyoxal synthase: a new control site in glycolysis" *FEBS Lett* 13:213-216.

Iverson, T. M., Luna-Chavez, C., Croal, L. R., Cecchini, G., Rees, D. C. (2002) "Crystallographic studies of the *Escherichia coli* quinol-fumarate reductase with inhibitors bound to the quinol-binding site. 2002" *J. Biol. Chem.* 277:16124-16130.

Jantama, K., Haupt, M. J., Svoronos, S. A., Zhang, X., Moore, J. C., Shanmugam, K. T., Ingram, L. O. (2008) "Combining metabolic engineering and metabolic evolution to develop nonrecombinant strains of *E. coli* C that produce succinate and malate" *Biotech. Bioeng.* 99(5):1140-1153.

Jarboe, L. R., Hyduke, D. R., Tran, L. M., Chou, K. J., Liao, J. C. (2008) "Determination of the *Escherichia coli* S-nitrosoglutathione response network using integrated biochemical and systems analysis" *J Biol Chem.* 283: 5148-5157.

Kao, K. C., Tran, L. M., Liao, J. C. (2005) "A global regulatory role of gluconeogenic genes in *Escherichia coli* revealed by transcriptome network analysis" *J Biol Chem* 280:36079-36087.

Karp, P. D., Keseler, I. M., Shearer, A., Latendresse, M., Krummenacker, M., Paley, S. M., Paulsen, I. T., Collado-Vides, J., Gamma-Castro, S., Peralta-Gil, M., Santos-Zavaleta, A., Penaloza-Spinola, M., Bonavides-Martinez, C., Ingraham, J. (2007) "Multidimensional annotation of *Escherichia coli* K-12 genome" *Nucl Acids Res.* 35(22): 7577-7590.

Keseler, I. M., Collado-Vides, J., Gamma-Castro, S., Ingraham, J., Paley, S., Paulsen, I. T., Peralta-Gil, M., Karp, P. D. (2005) "Ecocyc: A comprehensive database resource for *Escherichia coli*" *Nucl Acids Res* 33:D334-D337.

Kessler, D., and Knappe, J. (1996) Anaerobic dissimilation of pyruvate. In Neidhardt F C, Curtiss III R, Ingraham J L, Lin E C C, Low K B, Magasanik B, Reznikoff W S, Riley M, Schaechter M, Umbarger H E, editors. *Escherichia coli* and *Salmonella*: cellular and molecular biology. ASM Press, Washington, D.C. p. 199-205.

Kim, P., Laivebieks, M., Vieille, C., Zeikus, J. G. (2004) "Effect of overexpression of *Actinobacillus succinogenes* phosphoenolpyruvate carboxykinase on succinate production in *Escherichia coli*" *Appl Environ Microbiol.* 70(2): 1238-41.

Krebs, A., Bridger, W. A. (1980) "The kinetic properties of phosphoenolpyruvate carboxykinase of *Escherichia coli*" *Can J Biochem* 58(4): 309-318.

Kulla, H., and Gottschalk, G. (1977) "Energy-dependent inactivation of citrate lyase in *Enterobacter aerogenes*" *J. Bacteriol.* 132(3): 764-770.

Laivenieks, M., Vieille, C., Zeikus, J. G. (1997) "Cloning, sequencing, and overexpression of the *Anaerobiospirillum succiniciproducens* phosphoenolpyruvate carboxykinase (pckA) gene" *Appl Environ Microbiol* 63(6): 2273-2280.

Lee, E.-C., Yu, K., Martinez de Velasco, J., Tessarollo, L., Swing, D. A., Court, D. L., Jenkins, N. A., and Copeland, N. G. (2001) "A highly efficient *Escherichia coli*-based chromosome engineering system adapted for recombinogenic targeting and subcloning of BAC DNA" *Genomics* 73: 56-65.

Lee, S. Y., Hong, S. H., Lee, S. H., Park, S. J. (2004) "Fermentative production of chemicals that can be used for polymer synthesis" *Macromol. Biosci.* 4:157-164.

Lee, S. J, Lee, D. Y., Kim, T. Y., Kim, B. H., Lee, J., Lee, S. Y. (2005) "Metabolic engineering of *Escherichia coli* for enhanced production of succinic acid, based on genome comparison and in silico gene knockout simulation" *Appl Environ Microbiol* 71:7880-7887.

Lee, S. J., Song, H., Lee, S. Y. (2006) "Genome-based metabolic engineering of *Mannheimia succiniciproducens* for succic acid production" *Appl Environ Microbiol* 72(3): 1939 1948.

Lin, H., Bennett, G. N., San, K. Y. (2005a) "Chemostat culture characterization of *Escherichia coli* mutant strains metabolically engineered for aerobic succinate production: A study of the modified metabolic network based on metabolite profile, enzyme activity, and gene expression profile" *Metab. Engin.* 7:337-352.

Lin, H., Bennett, G. N., San, K. Y. (2005b) "Metabolic engineering of aerobic succinate production systems in *Escherichia coli* to improve process productivity and achieve the maximum theoretical succinate yield" *Metab. Engin.* 7:116-127.

Lin, H., Bennett, G. N., San, K. Y. (2005c) "Effect of carbon sources differing in oxidation state and transport route on succinate production in metabolically engineered *Escherichia coli*" *J. Ind. Microbial. Biotechnol.* 32:87-93.

Lin, H., Bennett, G. N., San, K. Y. (2005d) "Fed-batch culture of a metabolically engineered *Escherichia coli* strain designed for high-level succinate production and yield under aerobic conditions" *Biotechnol Bioeng* 90:775-779.

Lutgens, M., and Gottschalk, G. (1980) "Why a co-substrate is required for the anaerobic growth of *Escherichia coli* on citrate" *J. Gen Microbiol.* 119: 63-70.

Martinez, A., Grabar, T. B., Shanmugam, K. T., Yomano, L. P., York, S. W., Ingram, L. O. (2007) "Low salt medium for lactate and ethanol production by recombinant *Escherichia coli*" *Biotechnol. Lett.* 29:397-404.

Martinez-Morales, F., Borges, A. C., Martinez, A., Shanmugam, K. T., Ingram, L. O. (1999) "Chromosomal integration of heterologous DNA in *Escherichia coli* with precise removal of markers and replicons used during construction" *J Bacteriol.* 181:7143-7148.

McKinlay, J. B., Zeikus, J. G., Vieille, C. (2005) "Insights into *Actinobacillus succinogenes* fermentative metabolism in a chemically defined growth medium" *Appl Environ Microbiol.* 71(11):6651-6656.

McKinlay, J. B., Vieille, C. (2008) "$^{13}$C-metabolic flux analysis of *Actinobacillus* succinogenes fermentative metabolism at different NaHCO$_3$ and H$_2$ concentrations" *Metab. Eng.* 10:55-68.

McKinlay, J. B., Vieille, C., Zeikus, J. G. (2007) "Prospects for a bio-based succinate industry" *Appl Microbiol Biotechnol.* 76(4):727-740.

Meynial-Salles, I., Dorotyn, S., Soucaille, P. (2007) "A new process for the continuous production of succinic acid from glucose at high yield, titer and productivity" *Biotechnol Bioeng.* 99(1):129-135.

Miller, J. H. (1992) A short course in bacterial genetics: A laboratory manual and handbook for *Escherichia coli* and related bacteria, Cold Spring Harbor Press.

Millard, C. S., Chao, Y. P., Liao, J. C., Donnelly, M. I. (1996) "Enhanced production of succinic acid by overexpression of phosphoenolpyruvate carboxylase in *Escherichia coli*" *Appl. Environ. Microbiol.* 62:1808-1810.

Morikawa, M., K. Izui, et al. (1980) "Regulation of *Escherichia coli* phosphoenolpyruvate carboxylase by multiple effectors in vivo. Estimation of the activities in the cells grown on various compounds" *J Biochem* (Tokyo) 87(2): 441-449.

Moniruzzaman, M. et al. (1997) "Isolation and molecular characterization of high-performance cellobiose-fermenting spontaneous mutants of ethanologenic *Escherichia coli* K011 containing the *Klebsiella oxytoca* casAB operon" *Appl. Environ. Microbiol.* 63:4633-4637.

Nilekani, S., Sivaraman, C. (1983) "Purification and properties of citrate lyase from *Escherichia coli*" *Biochemistry* 22(20); 4657-63.

Oh, M. K., Rohlin, L., Kao, K. C., Liao, J. C. (2002) "Global expression profiling of acetate-grown *Escherichia coli*" *J Biol Chem* 277: 13175-13183.

Okino, S., Inui, M., Yukawa, H. (2005) "Production of organic acids by *Corynebacterium glutanicum* under oxygen deprivation" *Appl Microbiol Biotechnol* 68:475-480.

Posfai, G., Koob, M. D., Kirkpatrick, H. A., Blattner, F. C. (1997) "Versatile insertion plasmids for targeted genome manipulations in bacteria: Isolation, deletion, and rescue of the pathogenicity island LEE of the *Escherichia coli* O157: H7 genome" *J. Bacteriol.* 179:4426-4428.

Quentmeier, A., Holzenburg, A., Mayer, F., Antranikian, G. (1987) "Reevaluation of citrate lyase from *Escherichia coli*" *Biochim Biophys Acta* 913(1): 60-5.

Reed, J. L., Vo, T. D., Schilling, C. H., Palsson, B. O. (2003) "An expanded genome-scale model of *Escherichia coli* K-12 (iJR904 GSM/GPR)" *Genome Biol.* 4(9):R54.

Reitzer, L. 2004. 6 Jul. 2004, posting date. Chapter 3.6.1.3, Biosynthesis of Glutamate, Aspartate, Asparagine, L-Alanine, and D-Alanine. In A. Böck, R. Curtiss III, J. B. Kaper, F. C. Neidhardt, T. Nyström, K. E. Rudd, and C. L. Squires (ed.), EcoSal—*Escherichia coli* and *Salmonella*: cellular and molecular biology. [Online.] http://www.ecosal.org. ASM Press, Washington, D.C.

Samuelov, N. S., Lamed, R., Lowe, S., Zeikus, J. G. (1991) "Influence of CO$_2$—HCO$_3$ levels and pH on growth, succinate production, and enzyme-activities of *Anaerobiospirillum succiniproducens*" *Appl. Environ. Microbiol.* 57: 3013-3019.

Sanchez, A. M., Bennett, G. N., San, K. Y. (2005a) "Novel pathway engineering design of the anaerobic central metabolic pathway in *Escherichia coli* to increase succinate yield and productivity" *Metabolic Engineering* 7:229-239.

Sanchez, A. M., Bennett, G. N., San, K. Y. (2005b) "Efficient succinic acid production from glucose through overexpression of pyruvate carboxylase in an *Escherichia coli* alcohol dehydrogenase and lactate dehydrogenase mutant" *Biotechnol. Prog.* 21: 358-365.

Sanchez, A. M., Bennett, G. N., San, K. Y. (2006) "Batch culture characterization and metabolic flux analysis of succinate-producing *Escherichia coli* strains" *Metabolic Engineering* 8: 209-226.

Sanwal, B. D. and Smando, R. (1969a) "Malic enzyme of *Escherichia coli*: Possible mechanism for allosteric effects" *J Biol Chem.* 244(7):1824-1830.

Sanwal, B. D. and Smando, R. (1969b) "Malic enzyme of *Escherichia coli*: Diversity of the effectors controlling enzyme activity" *J Biol Chem.* 244(7):1817-1823.

Sanwal, B. D. (1970a) "Allosteric controls of amphibolic pathways in bacteria" *Bacteriol. Rev.* 34:20-39.

Sanwal, B. D. (1970b) "Regulatory characteristics of the diphosphopyridine nucleotide-specific malic enzyme of *Escherichia coli*" *J Biol Chem.* 245(5):1212-1216.

Sanwal, B. D. (1970c) "Regulatory mechanisms involving nicotinamide adenine nucleotide as allosteric effectors: A control of glucose 6-phosphate dehydrogenase" *J Biol Chem* 245(7):1625-1631.

Sawers, G., Bock, A. (1988) "Anaerobic regulation of pyruvate formate-lyase from *Escherichia coli* K-12" *J. Bacteriology.* 170:5330-5336.

Song, H., Lee, J. W., Choi, S., You, J. K., Hong, W. H., Lee, S. Y. (2007) "Effects of dissolved CO2 levels on the growth of *Mannheimia succiniciproducens* and succinic acid production" *Biotechnol Bioeng.* 98(6):1296-1304.

Storici, F., Coglievina, M., Bruschi, C. V. (1999) "A 2-μm DNA-based maker recycling system for multiple gene disruption in the yeast *Saccharomyces cerevisiae*" *Yeast* 15:271-283.

Stols, L., Donnelly, M. I. (1997) "Production of succinic acid through overexpression of NAD dependent malic enzyme in an *Escherichia coli* mutant" *Appl. Environ. Microbiol.* 63:2695-2701.

Thomason, L., Court, D. L., Bubunenko, M., Constantino, N., Wilson, H., Datta, S., Oppenheim, A. (2005) "Recombineering: Genetic Engineering in Bacteria Using Homologous Recombination", sections 1.16.1-1.16.21. In F. M. Ausubel, R. Brent, R. E. Klingston, D. D. Moore, J. G. Deidman, J. A. Smith, and K. Struhl (Eds.), Current Protocols in Molecular Biology. John Wiley & Sons Inc., New York.

Underwood, S. A., Buszko, M. L., Shanmugam, K. T., Ingram, L. O. (2004) "Lack of protective osmolytes limits final cell density and volumetric productivity of ethanologenic *Escherichia coli* KO11 during xylose fermentation" *Appl. Environ. Microbiol.* 70(5): 2734-40.

Underwood, S. A., Buszko, M. L., Shanmugam, K. T., Ingram, L. O. (2002) "Genetic changes to optimize carbon partitioning between ethanol and biosynthesis in ethanologenic *Escherichia coli*" *Appl Environ Microbiol.* 68(12): 6263-6272.

Unden, G. and Kleefeld, A. 30 Jul. 2004, posting date. Chapter 3.4.5, C$_4$-Dicarboxylate Degradation in Aerobic and Anaerobic Growth. In A. Böck, R. Curtiss III, J. B. Kaper, F. C. Neidhardt, T. Nyström, K. E. Rudd, and C. L. Squires (ed.), EcoSal—*Escherichia coli* and *Salmonella*: cellular and molecular biology. [Online.] http://www.ecosal.org. ASM Press, Washington, D.C.

van der Werf, M. J., M. V. Guettler, M. K. Jain, and J. G. Zeikus (1997) "Environmental and physiological factors affecting the succinate product ratio during carbohydrate fermentation by *Actinobacillus* sp. 130Z" *Arch. Microbiol.* 167:332-342.

Vemuri, G. N., Eiteman, M. A., Altman, E. (2002a) "Effects of growth mode and pyruvate carboxylase on succinic acid production by metabolically engineered strains of *Escherichia coli.*" *Appl. Environ. Microbiol.* 68:1715-1727.

Vemuri, G. N., Eiteman, M. A., Altman, E. (2002b) "Succinate production in dual-phase *Escherichia coli* fermentations depends on the time of transition from aerobic to anaerobic conditions" *J. Ind. Microbiol. Biotechnol.* 28, 325-332.

Wang, Q., Chen, X., Yang, Y., Zhao, X. (2006) "Genome-scale in silico aided metabolic analysis and flux comparisons of *Escherichia coli* to improve succinate production" *Appl Microbiol Biotechnol* 73:887-894.

Wendisch, V. F., Bott, M., Eikmanns, B. J. (2006) "Metabolic engineering of *Escherichia coli* and *Corynebacterium glutamicum* for biotechnological production of organic acids and amino acids" *Curr Opin Microbiol* 9:1-7.

Wood, B. E., Yomano, L. P., York, S. W., Ingram, L. O. (2005) "Development of industrial medium required elimination of the 2,3-butanediol fermentation pathway to maintain ethanol yield in an ethanologenic strain of *Klebsiella oxytoca*" *Biotechnol. Prog.* 21:1366-1372.

Wright, J. A. and Sanwal, B. D. (1969) "Regulatory mechanisms involving nicotinamide adenine nucleotide as allosteric effectors: Control of phosphoenolpyruvate carboxykinase" *J Biol Chem.* 244(7): 1838-1845.

Yun, N. R., San, K. Y., Bennett, G. N. (2005) "Enhancement of lactate and succinate formation in adhE or pta-ackA mutants of NADH dehydrogenase-deficient *Escherichia coli*" *J. Appl. Microbiol.* 99:1404-1412.

Zhang, X., Jantama, K., Moore, J. C., Shanmugam, K. T., Ingram, L. O. (2007) "Production of L-alanine by metabolically engineered *Escherichia coli*" *Appl. Microbial. Biotechnol.* 77: 355-366.

Zhou, S., Shanmugam, K. T., Ingram, L. O. (2003) "Functional replacement of the *Escherichia coli* D-(−)-lactate dehydrogenase gene (ldhA) with the L-(+)-lactate dehydrogenase gene (ldhL) from *Pediococcus acidilactici*" *Appl. Environ. Microbiol.* 69:2237-2244.

Zhou, S., Grabar, T. B., Shanmugam, K. T., Ingram, L. O. (2006) "Betaine tripled the volumetric productivity of D-(−)-lactate by *Escherichia coli* strain SZ132 in mineral salts medium" *Biotechnol. Lett.* 28:671-676.

---

We claim:

1. A genetically modified bacterial strain that comprises genetic modifications to target genes encoding: a) acetate kinase, b) lactate dehydrogenase, c) alcohol dehydrogenase, d) pyruvate formatelyase, e) methylglyoxal synthase, f) pyruvate oxidase, g) citrate lyase, h) aspartate aminotransferase, i) formate transporter, j) phosphate acetyltransferase, k) malic enzyme, and l) propionate kinase/α-ketobutyrate formatelyase, said genetic modifications inactivating the enzymatic activity of the polypeptide produced by said target gene and which produces at least 200 mM succinic acid.

2. The genetically modified bacterial strain of claim 1 wherein said genetically modified bacterial strain is *Escherichia coli, Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Brevibacterium ammoniagenes, Brevibacterium divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceurn, Brevibacterium roseum, Brevibacterium immariophilium, Brevibacterium linens, Brevibacterium protopharmiae, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Micrococcus sp. CCM825, Morganella morganii, Nocardia opaca, Nocardia rugosa, Planococcus eucinatus, Proteus rettgeri, Propionibacterium shermanii, Pseudomonas synxantha, Pseudomonas azotoformans, Pseudomonas fluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus sp. ATCC 15592, Rhodococcus sp. ATCC 19070, Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromo-* nas salmonicida, Bacillus pumilus, Bacillus circulans, Bacillus thiaminolyticus, Escherichia freundii, Microbacterium ammoniaphilum, Serratia marcescens, Salmonella typhimurium, Salmonella Schottmulleri, or Xanthomonas citri.

3. The genetically modified bacterial strain of claim 2, wherein said genetically modified bacterial strain is *Escherichia coli*.

4. A genetically modified bacterial strain that comprises:
(a) genetic modification to a citrate lyase gene and one or more of the target genes encoding: a) acetate kinase, b) lactate dehydrogenase, c) alcohol dehydrogenase, d) pyruvate formatelyase, e) methylglyoxal synthase, f) pyruvate oxidase, g) aspartate aminotransferase, h) formate transporter, i) phosphate acetyltransferase, j) malic enzyme, and/or k) propionate kinase/α-ketobutyrate formatelyase; or
(b) genetic modification to a citrate lyase gene, lactate dehydrogenase gene, alcohol dehydrogenase gene, acetate kinase gene, formate transporter gene, pyruvate formatelyase gene, methylglyoxal synthase gene, pyruvate oxidase gene, and one or more of the following target genes: a) aspartate aminotransferase, b) phosphate acetyltransferase, c) malic enzyme, and/or d) propionate kinase/α-ketobutyrate formatelyase;
said genetic modification inactivating the enzymatic activity of the polypeptide produced by said gene or said target gene and said genetically modified bacterial strain produces at least 200 mM succinic acid.

5. The genetically modified bacterial strain of claim 4, wherein said genetically modified bacterial strain is *Escherichia coli, Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Brevibacterium ammoniagenes, Brevibacterium divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Micrococcus* sp. CCM825, *Morganella morganii, Nocardia opaca, Nocardia rugosa, Planococcus eucinatus, Proteus rettgeri, Propionibacterium shermanii, Pseudomonas synxantha, Pseudomonas azotoformans, Pseudomonas fluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus* sp. ATCC 15592, *Rhodococcus* sp. ATCC 19070, *Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Escherichia freundii, Microbacterium ammoniaphilum, Serratia marcescens, Salmonella typhimurium, Salmonella Schottmulleri,* or *Xanthomonas citri*.

6. The genetically modified bacterial strain of claim 5, wherein said genetically modified bacterial strain is *Escherichia coli*.

7. The genetically modified bacterial strain of claim 1, wherein said genetically modified bacterial strain is metabolically evolved and selected for improved succinic acid production.

8. The genetically modified bacterial strain of claim 1, wherein the gene, or portions thereof, or target genes, or portions thereof, are inactivated by deletion, frameshift mutations, point mutations, the insertion of stop codons or combinations thereof.

9. The genetically modified bacterial strain of claim 1, wherein said genetically modified bacterial strain does not contain an exogenous gene or fragment thereof or only contains native genes.

10. The genetically modified bacterial strain of claim 1, with the proviso that: 1) said genetically modified bacterial strain has not had one or more of the following enzymes inactivated: a) fumarate reductase; b) ATP synthase; c) 2-ketoglutarate dehydrogenase; d) succinate dehydrogenase; e) glucose transporter; f) isocitrate lyase repressor; and/or 2) said genetically modified strain does not contain a plasmid or multicopy plasmid encoding and/or over-expressing genes for malate dehydrogenase, phosphoenolpyruvate carboxylase, pyruvate carboxylase and/or citrate synthase.

11. The genetically modified bacterial strain of claim 8 wherein said genetically modified bacterial strain is metabolically evolved and selected for increased succinic acid production.

12. The genetically modified bacterial strain of claim 1, wherein said genetically modified bacterial strain produces:
a) succinic acid concentrations of at least 250 mM, 300 mM, 350 mM, 400 mM, 450 mM, 500 mM, 550 mM, 600 mM, 650 mM, or 700 mM;
b) fumarate concentrations of at least 200 mM, 250 mM, 300 mM, 350 mM, 400 mM, 450 mM, 500 mM, 550 mM, 600 mM, 650 mM, or 700 mM; or
c) malate concentrations of at least 200 mM, 250 mM, 300 mM, 350 mM, 400 mM, 450 mM or 500 mM.

13. A genetically modified bacterial strain, wherein said genetically modified bacterial strain is KJ012 (NRRL B-50022), KJ017 (NRRL B-50023), KJ032 (NRRL B-50024), KJ060 (NRRL B-50025), KJ070 (NRRL B-50026), KJ071 (NRRL B-50027), KJ072 (NRRL B-50028), KJ073 (NRRL B-50029), KJ091 (NRRL B-50110), KJ098 (NRRL B-50111), KJ104 (NRRL B-50112), KJ110 (NRRL B-50113), KJ119 (NRRL B-50114), KJ122 (NRRL B-50115), or KJ134 (NRRL B-50116).

14. A method of culturing or growing a genetically modified bacterial strain comprising inoculating a culture medium with one or more genetically modified bacterial strains of claim 1 and culturing or growing said a genetically modified bacterial strain.

15. A method of producing succinate, fumarate or malate comprising culturing one or more genetically modified bacterial strains of claim 1 under conditions that allow for the production of succinate or malate or fumarate.

16. The method of claim 15, wherein said one or more genetically modified bacterial strain is KJ012 (NRRL B-50022), KJ017 (NRRL B-50023), KJ032 (NRRL B-50024), KJ060 (NRRL, B-50025), KJ070 (NRRL B-50026), KJ071 (NRRL B-50027), KJ072 (NRRL B-50028), KJ073 (NRRL B-50029), KJ091 (NRRL B-50110), KJ098 (NRRL B-50111), KJ104 (NRRL B-50112), KJ110 (NRRL B-50113), KJ119 (NRRL B-50114), KJ122 (NRRL B-50115), or KJ134 (NRRL B-50116).

17. The method of claim 14, wherein said genetically modified bacterial strain is cultured in a mineral salts medium.

18. The method of claim 17, wherein the mineral salts medium comprises between 2% and 20% (w/v) carbohydrate.

19. The method of claim 18, wherein the mineral salts medium contains 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5% or 20% (w/v) of a sugar.

20. The method of claim 18, wherein the carbohydrate is glucose, fructose, xylose, arabinose, galactose, mannose, rhamnose, sucrose, cellobiose, hemicellulose or combinations thereof.

21. The method of claim 15, wherein the yield of succinate or malate is greater than or equal to 90%.

22. The method of claim 21, wherein the yield is at least 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, or 99%.

23. The method of claim 15, wherein said genetically modified bacterial strain produces succinic acid concentrations of at least 250 mM, 300 mM, 350 mM, 400 mM, 450 mM, 500 mM, 550 mM, 600 mM, 650 mM, or 700 mM.

24. The method of claim 15, wherein said genetically modified bacterial strain produces malate concentrations of at least 200 mM, 250 mM, 300 mM, 350 mM, 400 mM, 450 mM or 500 mM.

25. The method of claim 15, wherein said genetically modified bacterial strain produces fumarate concentrations of at least 200 mM, 250 mM, 300 mM, 350 mM, 400 mM, 450 mM, 500 mM, 550 mM, 600 mM, 650 mM, or 700 mM.

26. The method of claim 14, wherein the growth medium comprises glycerol as a substrate for the production of succinate, malate or fumarate.

27. The method of claim 18, wherein said medium further comprises glycerol as a substrate for the production of succinate, malate or fumarate.

28. A composition comprising one or more genetically modified bacterial strains of claim 1 and medium.

29. A genetically modified bacterial cell wherein said bacterial cell produces at least 200 mM succinic acid and comprises the genetic modification of the following target genes: (a) ldhA; (b) ack; (c) adhE; and (d) focA-pflB, said genetic modification inactivating the enzymatic activity of the polypeptide encoded by said target genes.

30. The genetically modified bacterial cell of claim 29, wherein said bacterial cell further comprises the genetic modification of one or more genes selected from a group consisting of poxB, pta, tdcD, tdcE, mdh, sdh, iclR, icl, pdh, sfcA, aspC, aceAB, and citDEF, said one or more genetic modification(s) inactivating the enzymatic activity of the polypeptide encoded by said one or more genes.

31. The genetically modified bacterial cell of claim 29, wherein said bacterial cell further comprises the genetic modification of poxB, said genetic modification inactivating the enzymatic activity of the polypeptide encoded by poxB.

32. The genetically modified bacterial cell of claim 29, wherein said bacterial cell further comprises the genetic modification of: (a) poxB; (b) tdcD; and (c) tdcE, said genetic modifications inactivating the enzymatic activity of the polypeptides encoded by poxB, tdcD and tdcE.

33. The genetically modified bacterial cell of claim 29, wherein said bacterial cell further comprises the genetic modification of: (a) poxB; and (b) sfcA, said genetic modifications inactivating the enzymatic activity of the polypeptides encoded by poxB and sfcA.

34. The genetically modified bacterial cell of claim 29, wherein said bacterial cell further comprises the genetic modification of: (a) poxB; (b) sfcA; (c) tdcD; and (d) tdcE, said genetic modifications inactivating the enzymatic activity of the polypeptides encoded by poxB, sfcA, tdcD and tdcE.

35. The genetically modified bacterial cell of claim 29, wherein said bacterial cell further comprises genetic modifications of (a) tdcD; (b) tdcE (c) aspC; (d) sfcA (e) poxB; (f) citF; and (g) pta, said genetic modifications inactivating the enzymatic activity of the polypeptides encoded by tdcD, tdcE, aspC, sfcA, poxB, citF and pta.

36. The genetically modified bacterial cell of claim 29, wherein said bacterial cell is *Escherichia coli, Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Brevibacterium ammoniagenes, Brevibacterium divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fircatum, Flavobacterium aurantinum, Flavobacterium rhenanum, Flavobacterium sewanense, Flavobacterium breve, Flavobacterium meningosepticum, Micrococcus sp. CCM825, Morganella morganii, Nocardia opaca, Nocardia rugosa, Planococcus eucinatus, Proteus rettgeri, Propionibacterium shermanii, Pseudomonas synxantha, Pseudomonas azotoformans, Pseudomonas fluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus sp. ATCC 15592, Rhodococcus sp. ATCC 19070, Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Bacillus licheniformis, Bacillus subtilis, Bacillus amyloliquifaciens, Bacillus coagulans, Escherichia freundii, Microbacterium ammoniaphilum, Serratia marcescens, Salmonella typhimurium, Salmonella schottmulleri,* or *Xanthomonas citri.*

37. The genetically modified bacterial cell of claim 29, wherein said bacterial cell is *Escherichia coli*.

38. The genetically modified bacterial cell of claim 29, wherein said bacterial cell does not have any exogenous nucleotide sequence.

39. The genetically modified bacterial strain of claim 29, wherein said genetically modified bacterial strain is metabolically evolved and selected for increased succinic acid production.

40. The genetically modified bacterial cell of claim 29, wherein said bacterial cell produces at least 250 mM succinic acid.

41. A genetically modified bacterial cell, wherein said bacterial cell comprises the genetic modification of the following target genes: (a) ldhA; (b) ackA; (c) adhE; (d) focA-pflb; and (e) mgsA and produces at least 200 mM succinic acid, wherein said genetic modification inactivates the enzymatic activity of the polypeptide encoded by said target genes.

42. The genetically modified bacterial cell of claim 41, wherein said bacterial cell further comprises the genetic modification of one or more genes selected from a group consisting of poxB, pta, tdcD, tdcE, mdh, sdh, iclR, icl, pdh, sfcA, aspC, aceAB, and citDEF, said one or more genetic modification(s) inactivating the enzymatic activity of the polypeptide encoded by said one or more genes.

43. The genetically modified bacterial cell of claim 41, wherein said bacterial cell further comprises the genetic modification of poxB, said genetic modification inactivating the enzymatic activity of the polypeptide encoded by poxB.

44. The genetically modified bacterial cell of claim 41, wherein said bacterial cell further comprises the genetic modification of: (a) poxB; (b) tdcD; and (c) tdcE, said genetic modification inactivating the enzymatic activity of the polypeptides encoded by poxB, tdcD and tdcE.

45. The genetically modified bacterial cell of claim 41, wherein said bacterial cell further comprises the genetic modification of: (a) poxB; and (b) sfcA, said genetic modification inactivating the enzymatic activity of the polypeptides encoded by poxB and sfcA.

46. The genetically modified bacterial cell of claim 41, wherein said bacterial cell further comprises the genetic modification of: (a) poxB; (b) sfcA; (c) tdcD; and (d) tdcE, said genetic modification inactivating the enzymatic activity of the polypeptides encoded by poxB, sfcA, tdcD and tdcE.

47. The genetically modified bacterial cell of claim 41, wherein said bacterial cell further comprises the genetic modification of: (a) tdcD; (b) tdcE (c) aspC; (d) sfcA (e) poxB; (f) citF; and (g) pta, said genetic modification inactivating the enzymatic activity of the polypeptides encoded by tdcD, tdcE, aspC, sfcA, poxB, citF, and pta.

48. The genetically modified bacterial cell of claim 41, wherein said bacterial cell is *Escherichia coli, Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Brevibacterium ammoniagenes, Brevibacterium divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Corynebacterium acetophilum, Corynebacterium glutamicum, Corynebacterium callunae, Corynebacterium acetoacidophilum, Corynebacterium acetoglutamicum, Enterobacter aerogenes. Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Micrococcus* sp. CCM825, *Morganella morganii, Nocardia opaca, Nocardia rugosa, Planococcus eucinatus, Proteus rettgeri, Propionibacterium shermanii, Pseudomonas synxantha, Pseudomonas azotoformans, Pseudomonas fluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus* sp. ATCC 15592, *Rhodococcus* sp. ATCC 19070, *Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulars, Bacillus thiaminolyticus, Bacillus licheniformis, Bacillus subtilis, Bacillus amyloliquifaciens, Bacillus coagulans, Escherichia freundii, Microbacterium ammoniaphilum, Serratia marcescens, Salmonella typhimurium, Salmonella schottmulleri,* or *Xanthomonas citri*.

49. The genetically modified bacterial cell of claim 41, wherein said bacterial cell is *Escherichia coli*.

50. The genetically modified bacterial cell of claim 41, wherein said bacterial cell does not have any exogenous nucleotide sequence.

51. The genetically modified bacterial strain of claim 41, wherein said genetically modified bacterial strain is metabolically evolved and selected for increased succinic acid production.

52. The microorganism of claim 1, wherein said microorganism overexpresses phosphoenolpyruvate carboxykinase (pck).

53. The microorganism of claim 29, wherein said microorganism overexpresses phosphoenolpyruvate carboxykinase (pck).

54. The microorganism of claim 41, wherein said microorganism overexpresses phosphoenolpyruvate carboxykinase (pck).

\* \* \* \* \*

UNITED STATES PATENT AND TRADEMARK OFFICE
CERTIFICATE OF CORRECTION

| | |
|---|---|
| PATENT NO. | : 8,691,539 B2 |
| APPLICATION NO. | : 12/529826 |
| DATED | : April 8, 2014 |
| INVENTOR(S) | : Kaemwich Jantama et al. |

It is certified that error appears in the above-identified patent and that said Letters Patent is hereby corrected as shown below:

In the Specification,

Column 8,
Line 16, "said a genetically" should read --said genetically--.

Column 11,
Line 34, "strain one according" should read --strain according--.

Column 12,
Line 29, "docs not" should read --does not--.

Column 13,
Line 61, "cat-sac)" should read --*cat-sacB*--.

Column 14,
Line 5, "500 by" should read --500 bp--.
Line 10, "mgsA-112" should read --*mgsA*-1/2--.
Line 12, "4958 by" should read --4958 bp--.
Line 14, "4958 by" should read --4958 bp--.
Line 36, "clones' were" should read --clones were--.

Column 15,
Line 40, "800 by" should read --800 bp--.

Column 17,
Line 2, "rationale" should read --rational--.

Column 18,
Line 48, "at -64 by" should read --at -64 bp--.

Signed and Sealed this
Thirtieth Day of December, 2014

Michelle K. Lee
*Deputy Director of the United States Patent and Trademark Office*

Lines 49-50, "is -139 by" should read --is -139 bp--.

Column 21,
Line 45, "phosphenolpyruvate" should read --phosphoenolpyruvate--.

Column 24,
Line 2, "concentrations was" should read --concentrations were--.
Line 20, "50 by" should read --50 bp--.
Line 21, "20 by" should read --20 bp--.

Column 25,
Line 15, "BG1II" should read --*Bgl*II--.
Line 24, "StPBXPScomp)" should read --SfPBXPScomp)--.
Line 33, "with Pad" should read --with *Pac*I--.
Line 38, "the Pad" should read --the *Pac*I--.
Line 43, "1000 by" should read --1000 bp--.
Line 49, "6861 by" should read --6861 bp--.
Line 53, "6861 by" should read --6861 bp--.

Column 26,
Line 7, "200 by" should read --200 bp--.
Line 20, "chroramphenicol" should read --chloramphenicol--.
Line 22, "with Pad" should read --with *Pac*I--.
Line 49, "ackA21/pta2)" should read --*ackA2/pta2*--.

Column 27,
Line 16, "phosphoenylpyruvate" should read --phosphoenolpyruvate--.

Column 28,
Line 30, "The a" should read --The α--.
Line 43, "arise form" should read --arise from--.
Lines 62-63, "create an auxotrophic requirements" should read
    --create auxotrophic requirements--.

Column 31,
Lines 51-52, Organisms "*Succinivibrio dextrinosolvens* ATCC 19716 and *Corynebacterium glutanicum* R"
    "ATCC 19716         fermentation, 36 h. 40 g/l glucose
        *Corynebacterium*    (121 g total glucose) in Defined"
should read --ATCC 19716    fermentation, 36 h.
        *Corynebacterium*    40 g/l glucose (121 g total glucose) in Defined--.

Column 33, Column "Organism",
Line 23, "ack4-pta poxB," should read --*ackA-pta poxB,*--.

CERTIFICATE OF CORRECTION (continued)
U.S. Pat. No. 8,691,539 B2

Column 35,
Row "pLOI4228",
        "ycc'-mgsA-helD' (PCR)" should read --*yccT'-mgsA-helD'* (PCR)--.
Row "JMcatsacB",
        "5'TTAGCTAGCATGTGACCGAAGATCACTTCG3' (SEQ ID NO: 10)" should read --5'TTAGCTAGCATGTGACGGAAGATCACTTCG3' (SEQ ID NO: 10).--.

Column 37,
Row "birA (RT-PCR)",
        "5'ATCGTGATGGCGCAAGT3' (SEQ ID NO: 28)" should read
        --5'ATCGTGATGGCGGAAGT3' (SEQ ID NO: 28)--.

Column 39,
Column "Strain$^a$", "KJ072          should read --KJ072
    (*ldhA, ackA, adhE, focA*          (*ldhA, ackA, adhE, focA*
    *pflB, mgsA, puxB*)"              *pflB, mgsA, poxB*)--.

Column 41,
Column "Strain$^a$", "KJ072          should read --KJ072
    (*ldhA, ackA, adhE, focA*          (*ldhA, ackA, adhE, focA*
    *pflB, mgsA, puxB*)"              *pflB, mgsA, poxB*)--.

Column 43,
Table 6, Row "KJ076", "Δack4" should read --Δ*ackA*--.
Table 6, Row "KJ079", "Δack4" should read --Δ*ackA*--.
Table 6, Row "KJ110", "kJ104," should read --KJ104,--.

Column 45,
Table 6, Row "pLOI4151", "BGlII digestion" should read --*Bgl*II digestion--.

Column 47,
Table 6, Row "pLOI4283", "(using sfrA-up/down" should read --(using *sfcA*-up/down--.
Table 6, Row "pLOI4711", "(using ack4-2/pta-2" should read --(using *ackA-2/pta*-2--.

Column 53,
Table 7, Column "Strain", Row "KJ134", "13 ± 5" should read --13 ± 2--.
Line 52, "Shanmugan," should read --Shanmugam,--.

Column 54,
Line 46, "Delbacre," should read --Delbaere,--.

Column 55,
Line 5, "Goldie, A. N." should read --Goldie, A. H.--.

CERTIFICATE OF CORRECTION (continued)
U.S. Pat. No. 8,691,539 B2

In the Claims,

Column 90,
Line 57, "(pek)." should read --(pck).--.

UNITED STATES PATENT AND TRADEMARK OFFICE
CERTIFICATE OF CORRECTION

PATENT NO. : 8,691,539 B2
APPLICATION NO. : 12/529826
DATED : April 8, 2014
INVENTOR(S) : Jantama et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 667 days.

Signed and Sealed this
Twenty-ninth Day of September, 2015

Michelle K. Lee
*Director of the United States Patent and Trademark Office*